(12) United States Patent
Suzuki et al.

(10) Patent No.: US 7,704,206 B2
(45) Date of Patent: Apr. 27, 2010

(54) ENDOSCOPE THAT PROVIDES SELECTION OF EACH ILLUMINATION MODE OF FOUR DIFFERENT ILLUMINATION MODES

(75) Inventors: Takayuki Suzuki, Hachioji (JP); Akira Hasegawa, Musashino (JP); Shinya Matsumoto, Machida (JP)

(73) Assignee: Olympus Corporation, Tokyo (JP)

( * ) Notice: Subject to any disclaimer, the term of this patent is extended or adjusted under 35 U.S.C. 154(b) by 709 days.

(21) Appl. No.: 10/453,745

(22) Filed: Jun. 4, 2003

(65) Prior Publication Data
US 2003/0229270 A1 Dec. 11, 2003

(30) Foreign Application Priority Data
Jun. 5, 2002 (JP) .............................. 2002-164875

(51) Int. Cl.
*A61B 1/06* (2006.01)
*A61B 1/04* (2006.01)
*H04N 7/18* (2006.01)

(52) U.S. Cl. ........................................ 600/178; 348/70
(58) Field of Classification Search ................. 600/178, 600/181, 476; 348/68, 70
See application file for complete search history.

(56) References Cited

U.S. PATENT DOCUMENTS

| | | | | |
|---|---|---|---|---|
| 4,807,026 A | * | 2/1989 | Nishioka et al. ............. | 348/70 |
| 4,959,710 A | | 9/1990 | Uehara et al. | |
| 4,983,019 A | * | 1/1991 | Ikuno et al. ................. | 600/181 |
| 5,001,556 A | * | 3/1991 | Nakamura et al. ............ | 348/70 |
| 5,512,940 A | * | 4/1996 | Takasugi et al. .............. | 348/71 |
| 5,748,371 A | | 5/1998 | Cathey, Jr. et al. | |
| 6,061,374 A | * | 5/2000 | Nightingale et al. ...... | 372/50.21 |
| 6,126,593 A | * | 10/2000 | Honda et al. ................ | 600/180 |
| 6,241,656 B1 | | 6/2001 | Suga | |
| 6,464,633 B1 | | 10/2002 | Hosoda et al. | |
| 2003/0139650 A1 | * | 7/2003 | Homma ...................... | 600/181 |
| 2003/0176768 A1 | * | 9/2003 | Gono et al. ................. | 600/109 |

FOREIGN PATENT DOCUMENTS

| | | |
|---|---|---|
| JP | 08-140929 | 6/1996 |
| JP | 2000-41942 | 2/2000 |
| JP | 2001-170009 | 6/2001 |

* cited by examiner

*Primary Examiner*—John P Leubecker
*Assistant Examiner*—Philip R Smith
(74) *Attorney, Agent, or Firm*—Arnold International; Bruce Y. Arnold

(57) ABSTRACT

An endoscope is disclosed that provide selection of each illumination mode of four different illumination modes, with one of the four different illumination modes being a mode which sequentially transmits very narrow wavelength ranges at three different wavelength regions within the visible spectrum.

4 Claims, 39 Drawing Sheets

ENDOSCOPE THAT PROVIDES SELECTION OF EACH ILLUMINATION MODE OF FOUR DIFFERENT ILLUMINATION MODES

CROSS REFERENCE TO RELATED APPLICATION

This application is related in subject matter to that of commonly assigned U.S. application Ser. No. 10/320,502, entitled "Endoscope", filed Dec. 12, 2002. Also, this application claims the benefit of foreign priority from Japanese Patent Application No. 2002-164875, filed Jun. 5, 2002, the contents of which are hereby incorporated by reference.

BACKGROUND OF THE INVENTION

Endoscope apparatuses wherein a scope is inserted into a coelom in order to observe portions of the alimentary canal such as the esophagus, the stomach, the small intestine, and the large intestine, or into the trachea and the lungs for observing images on a TV monitor screen are commonly utilized. Recently, the use of illumination light of specific wavelength ranges for observing in vivo tissue has started to become popular. For example, an endoscope apparatus has been proposed for more easily identifying lesions that are difficult to discern with normal observation light which utilizes the phenomenon that in vivo tissue emits fluorescence when illuminated by light of specific wavelengths. Furthermore, attempts have been made to gather detailed information of lesions by utilizing the light absorbance properties and the light scattering properties of in vivo tissues to light of different wavelength ranges. For example, Japanese Laid Open Patent Application H08-140929 discloses an apparatus which can switch between providing an ordinary color image observation and a fluorescent image observation of a lesion. At the tip of the endoscope are installed one image sensing chip that detects ordinary color images and a separate image sensing chip that detects fluorescent light images.

As another example, Japanese Laid Open Patent Application 2001-170009 discloses an apparatus which can switch between providing an ordinary color image observation and the observation of blood vessel structure at various depths from the surface of a lesion. In this apparatus, a light source unit is used which provides different illumination light for the two kinds of observations.

As another example, Japanese Laid Open Patent Application 2000-41942 discloses an apparatus which can switch between providing ordinary color image observation verses infrared image observation of a lesion. In this apparatus as well, a light source unit is used which provides different illumination light for the different kinds of observations. This endoscope apparatus can provide two kinds of observations using different specialized infrared illuminations as well as provide an ordinary color image observation. However, when performing a precise diagnosis or treatment of a lesion by combining three kinds of observations, three kinds of endoscope apparatuses have to be prepared. Because of this, there is a shortcoming in that it is troublesome to have to change the endoscope apparatus every time the kind of special light observation is changed, and such a procedure increases the time required for such an endoscopic examination. Also disclosed in this prior art example is a device for performing individual special light observations effectively and efficiently. However, there is no mention of a method and apparatus for diagnosing a lesion state correctly within a short period of time by combining special light observations. Namely, there is no disclosure of a device which allows the state of a lesion to be immediately determined without taking a pathological sample and having it examined in detail, after which a decision may be made for treatment.

BRIEF SUMMARY OF THE INVENTION

The present invention relates to an endoscope for observing the interior of a coelom. More specifically, the present invention provides an endoscope and an endoscope diagnosing method which can efficiently perform the work of precisely diagnosing and treating a lesion by combining an ordinary color image observation and multiple special light observations.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

Figure 1:
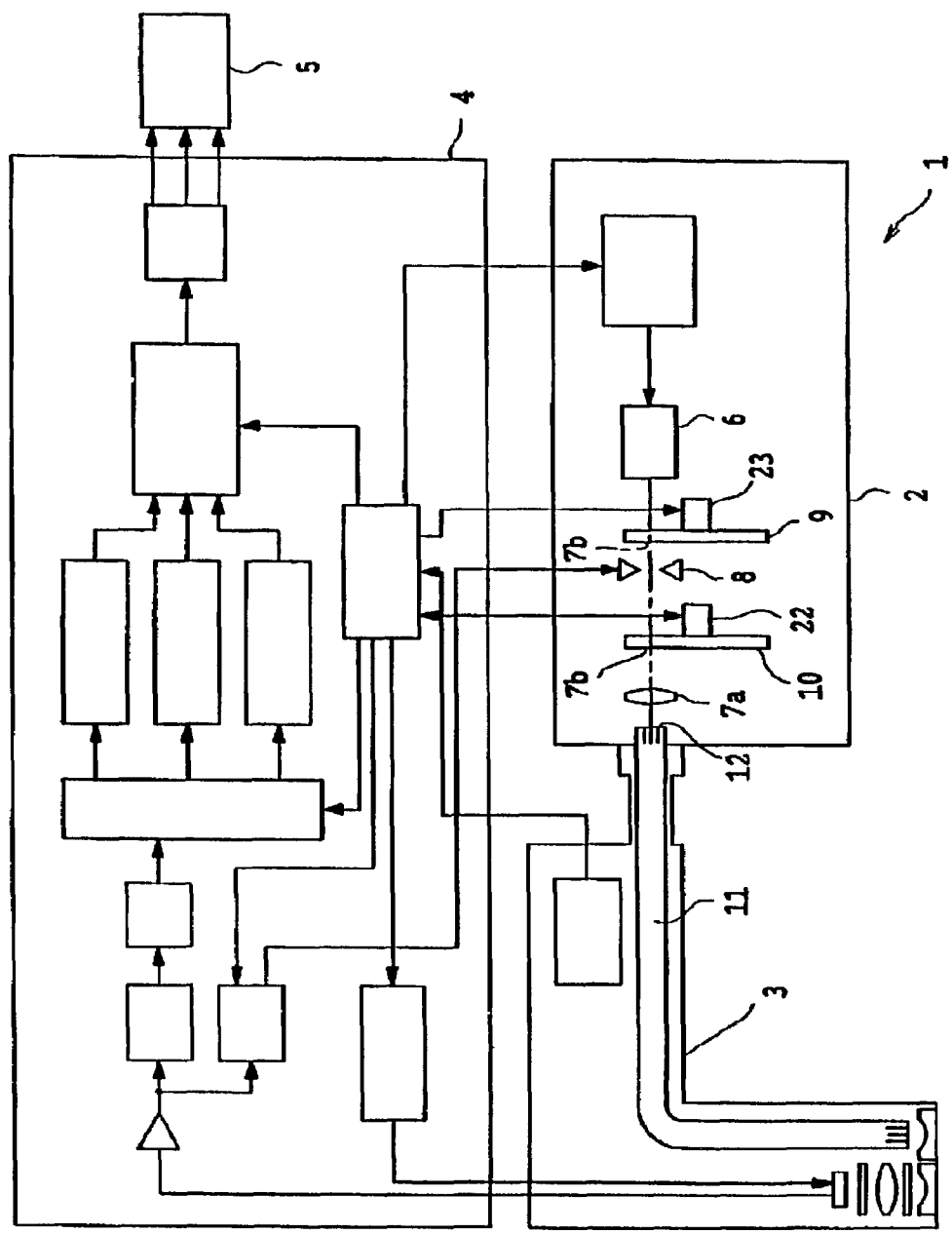
FIG. 1 shows the configuration of an endoscope apparatus according to Embodiment 1.

The present invention relates to diagnosing and/or treating a lesion correctly by combining ordinary color image observation and multiple special light observations to accomplish diagnosis while observing the lesion in vivo, and involves a series of procedures discussed below so as to provide an adequate treatment of the lesion.

First, an observation using a fluorescent image is performed in order to discern a lesion such as may occur in the early stages of cancer. Such lesions are otherwise difficult to distinguish from normal tissue of a living body using ordinary observations. Thus, in this manner the location of the lesion is determined.

Next, the lesion is magnified and imaged utilizing light in the visible region that has been divided into multiple, very narrow wavelength ranges, thereby enabling the structure of blood vessels at various depths from the surface of the lesion to be discerned. This helps determine the boundary between the lesion versus normal living tissue, and thus the range of the lesion is specified.

Next, an observation with infrared light is performed in order to observe the state of the lower layer of the mucosa (sub-mucosa) under the lesion. Thus, the degree of infiltration of the lesion into the mucosal layer is precisely determined. This is of great importance in deciding whether it will be possible to remove the lesion using endoscopic procedures.

If it is decided that it is possible to remove the lesion endoscopically, the lesion is removed through an endoscopic mucosal resection. Alternatively, the lesion may be burned using light from a laser.

The endoscope apparatus of the present invention is constructed so that different combinations of optical filters are placed in a light path in order to perform observation and treatment procedures of an in vivo lesion using a single endoscope.

More specifically, a light source unit is equipped with at least a lamp, a condensing lens, and multiple filters that may be selectively inserted into and removed from an illumination light path so that at least three of the following four illumination modes can be selected:

illumination mode 1—a mode that sequentially transmits excitation light for obtaining fluorescence from in vivo tissue and light having wavelength components different from the excitation light so as to obtain information from in vivo tissue other than by using fluorescence of the in vivo tissue;

illumination mode 2—a mode that sequentially transmits red, green, and blue wavelength ranges of light for obtaining color images of in vivo tissue with good color reproducibility;

illumination mode 3—a mode which sequentially transmits very narrow wavelength ranges at different wavelength regions within the visible spectrum for enhancing the resolution of blood vessel structures at selected depths from the surface of in vivo tissue; and illumination mode 4—a mode which sequentially transmits infrared region light of at least two different wavelength ranges for obtaining infrared images having good contrast of in vivo tissue.

In the preferred embodiments of the invention, any of the above four illumination modes can be selected. A turret is placed in the light path of the light source unit and serves to insert/withdraw from the light path multiple filters having different spectral transmittance. In addition, a rotary filter wheel is also placed in the light path of the light source unit which serves to sequentially insert/withdraw optical filters in the light path within a rotation cycle of the rotary filter wheel equipped with filters having different spectral transmittance. By combining filters of the turret and the rotary filter wheel, any of the above four different illumination modes can be selected.

On the rotary filter wheel are placed a concentric configuration of single bandpass filters, herein termed filter set A, which transmits visible light in three different wavelength ranges, and another concentric configuration of double bandpass filters, herein termed filter set B, which transmits visible light in the blue, green and red wavelength ranges and simultaneously transmits near-infrared region light in two narrow wavelength ranges. One of the filter sets A or B is inserted into the light path according to which of the four illumination modes, discussed above, is selected so that the light source unit successively provides the desired illumination as the filter wheel is rotated. In the light source unit which sequentially irradiates light of different wavelength ranges, one of multiple intensity adjustment filters may be placed on the turret so that the relative intensity of the light of different wavelength ranges changes according to the selected illumination mode.

In addition, the turret and the rotary filter wheel are placed in the light path of the light source unit so that the following condition is satisfied:

$$\theta \leq 13°$$ Condition (1)

where θ is the angle of incidence of the light beam onto the filters placed within the turret and the rotary filter wheel.

Also, on the surface of the condensing lens of the light source unit, a multilayer film coating is provided having the following spectral reflectance properties:

$$R(410\ nm) \leq 2.7\%$$ Condition (2)

$$R(420\text{-}750\ nm) \leq 0.5\%$$ Condition (3)

$$R(750\text{-}850\ nm) \leq 1.5\%$$ Condition (4)

$$R(850\text{-}950\,nm) \leq 4\% \quad \text{Condition (5)}$$

where

R (410 nm) is the reflectance at a wavelength λ=410 nm,

R (420-750 nm) is the average reflectance in the wavelength range λ=420-750 nm,

R (750-850 nm) is the average reflectance in the wavelength range λ=750-850 nm, and R (850-950 nm) is the average reflectance in the wavelength range λ=850-950 nm.

Furthermore, the endoscope apparatus of the present invention performs illumination and imaging of an object by combining a scope with an image processing device with a light source unit, wherein multiple optical elements are placed in the light path of the light source unit. On the surfaces of these multiple optical elements are provided coatings having different spectral transmittance. The light source unit optical elements that are placed in series in the light path are partially selectable by translation of the rotary filter wheel so that the outer ring, the inner ring, or none of the optical elements are in the light path, and thus the overall transmittance of the coatings on the optical elements placed in the light path of the light source unit can be modified. When observing an object, multiple different image information is obtained by observing the object while changing the overall transmittance of the light source unit and by changing the overall transmittance properties of the optical elements in the imaging system of the scope. This image information is then processed by an image processing device and displayed on a monitor.

There are at least three kinds of combinations for obtaining an overall spectral transmittance of the optical elements in the light source unit and an overall spectral transmittance of the optical elements in the scope imaging system. Each of the light source unit and scope imaging system has bandpass properties in different wavelength regions between 330nm and 1100 nm. Also, the light source unit optical elements and the scope imaging system optical elements each include an optical filter wherein a multilayer film coating is provided on a parallel-plate-shaped optical element. The optical filter of the light source unit functions as an excitation light passing filter for observing fluorescent images of in vivo tissues, and the optical filter of the imaging optical system functions as an excitation light blocking filter. As is well known in the art, the light blocking property of a filter is expressed in terms of optical density. For example, the term "OD4" indicates that the optical density, which is defined as $\log_{10}$ (I/I'), equals 4, with I being the intensity of light incident onto the filter and I' being the intensity of light transmitted by the filter. In this case, the light blocking property of the optical filter is OD4 or higher at a wavelength λ2 which is shifted in a direction of decreasing intensity by an amount Δλ that equals 20 nm from a wavelength λ1, where λ1 is a wavelength where the transmittance becomes 50% for light having an angle of incidence η equal to 0°, and the light blocking property of the optical filter is OD4 or higher at the wavelength λ2 to light having an angle of incidence η equal to 25°.

When the optical filter in the imaging optical system blocks excitation light by overlapping two or more optical filters in series, the light blocking property of the optical filter is OD4 or higher for wavelengths in the excitation light wavelength range.

As mentioned above, the optical filter that is placed in the light source unit is positioned so that Condition (1) above is satisfied. Also, the excitation light blocking filter is positioned so that the following Condition (6) is satisfied:

$$\eta \leq 25° \quad \text{Condition (6)}$$

where η is the maximum incidence angle of light rays onto the excitation light blocking filter.

The light source unit optical elements and the scope imaging optical system optical elements each include a lens having a curved surface at least on one side. On the surface of this lens, a multilayer film coating is provided which satisfies the above Conditions (2)-(5).

Also, in an endoscope apparatus where ordinary color image observations and fluorescent image observations of in vivo tissues can be made, the optical elements placed in the imaging optical system of the scope have an overall transmittance property that transmits the optical components utilized for ordinary color image observation and blocks the light components that cause a problem to the observation of the fluorescent image observation.

Furthermore, the endoscope apparatus of the present invention performs illumination and imaging of an object by combining a scope with an image processing device and a light source unit, wherein multiple optical elements are placed in the light path of the light source unit and the imaging optical system, and coatings with different transmittance properties are provided on the surfaces of multiple optical elements placed in the light path of the light source unit and imaging optical system of the scope. By making the light source unit optical elements partially replaceable in the light path, the total transmittance property of the coatings on the optical elements placed in the light path of the light source unit can be modified. When observing an object, multiple different image types can be obtained by observing the object while changing the combination of the total transmittance property of the light source unit optical elements and the total transmittance property of the imaging optical system optical elements, and the image information is then processed by the image processing device and displayed on the monitor. Then, observation and treatment of a lesion of a living body may be accomplished by performing the following four procedures.

Procedure 1—By performing fluorescent image observations of a lesion such as early cancer, which is difficult to distinguish from normal tissue when observed in normal light, the lesion location is specified.

Procedure 2—Once the location and rough range of the lesion becomes clear by Procedure 1, the lesion is magnified and imaged. Then, by utilizing the visible region light divided into multiple, very narrow wavelength ranges, blood vessel structure at various depths from the surface of the lesion is examined, and the boundary between the lesion tissue and normal tissue is clarified. Thus, the range of the lesion is specified.

Procedure 3—By performing observations with infrared-region light of the lesion confirmed by Procedure 2 and by examining the state of the lower layer of the mucosa at the lesion, infiltration of the lesion into the tissue is ascertained and a determination is made as to whether it is possible to endoscopically remove the lesion.

Procedure 4—Based on the judgement in Procedure 3, if it is possible to endoscopically remove the lesion, the lesion is removed through the endoscopic mucosal resection while observing the lesion as images in normal color. Alternatively, a treatment of burning it with laser may be used.

Furthermore, the present invention is a diagnosing method in which lesions of a living body are diagnosed using an endoscope. In the light source unit of the endoscope apparatus, coatings with different transmittance properties are provided on multiple optical elements placed in the light path of the light source unit and on surfaces of multiple optical elements placed in the light path of the imaging optical system of the scope. By making the light source unit optical elements partially replaceable, the overall transmittance properties of the coatings on the optical elements placed in the light path of the light source unit are modified.

When observing an object, multiple different image information is obtained by observing the object while changing the combination of the overall transmittance property of the light source unit optical elements and the overall transmittance property of the imaging optical system optical elements, and the image information is processed by the image processing device and displayed on the monitor. The diagnosing method is performed in combination with the following three observation methods.

Observation Method 1—By performing fluorescent image observation of a lesion, such as early cancer, whose location used to be difficult to distinguish from normal tissue by observing the living body using an ordinary color image alone, is specified.

Observation Method 2—The capillary blood vessel structure distributed in the mucosal layer at the lesion is examined by using illuminating light in the visible region having narrow wavelength ranges and, by observing magnified images of the lesion, the boundary between the lesion tissue and normal tissue is clarified so that the range of the lesion is specified.

Observation Method 3—By performing observations with infrared region light, the structure of the blood vessels and lymphatics in the lower layer of the mucosa at the lesion are examined, and the presence/absence of infiltration of the lower layer of the mucosa is judged so that a determination is made as to whether it is possible to endoscopically remove the lesion.

FIG. 1 shows the endoscope apparatus 1 of the present invention. The endoscope apparatus 1 includes a light source unit 2, a scope 3, an image processing device 4, and an observation monitor 5. The light source unit 2 is equipped with a lamp 6, multiple optical elements 7a,7b,and a light amount adjusting means 8. The optical elements include a lens 7a having at least one curved surface on one side, and multiple optical filters 7b formed of multilayer interference film coatings on parallel plates.

Figure 2:
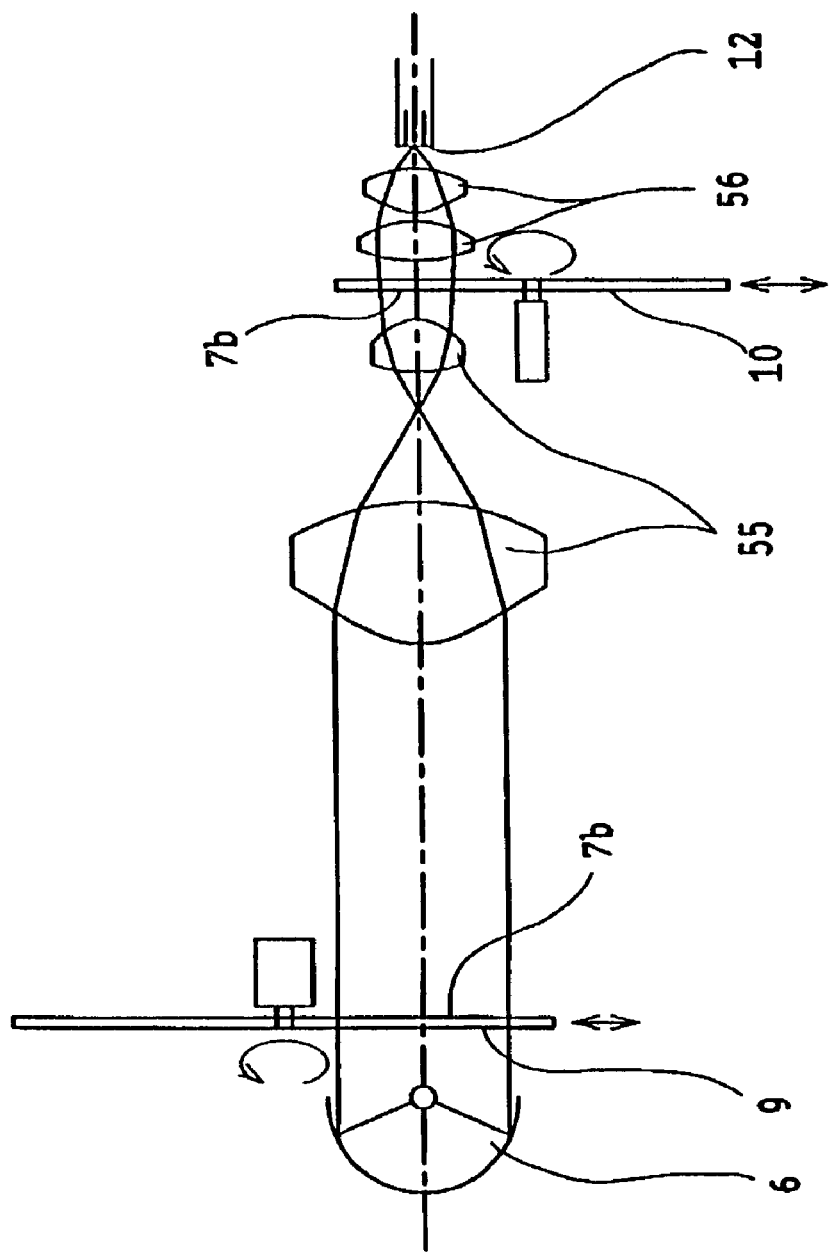
FIG. 2 shows the configuration of an optical system of a light source unit used in the endoscope apparatus according to Embodiment 1.
Figure 3A:
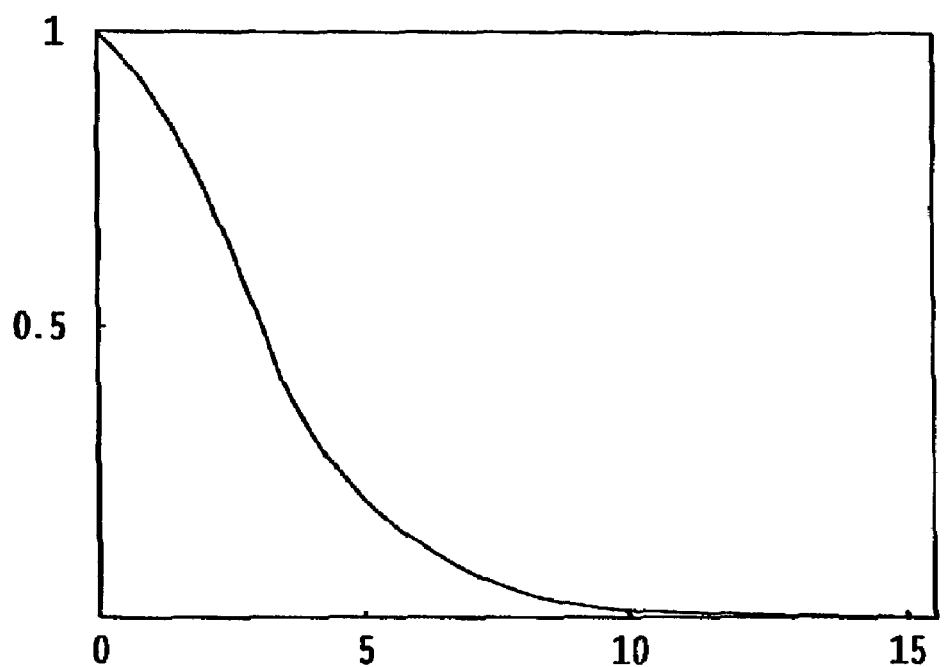
FIGS. 3(a) and 3(b) show the illumination distribution of a light beam emerging from the aperture window of the xenon lamp used in Embodiment 1, with FIG. 3(a) being the illumination distribution after an accumulated usage time of about 6 hours, and with FIG. 3(b) being the illumination distribution after an accumulated usage time of about 100 hours.
Figure 3B:
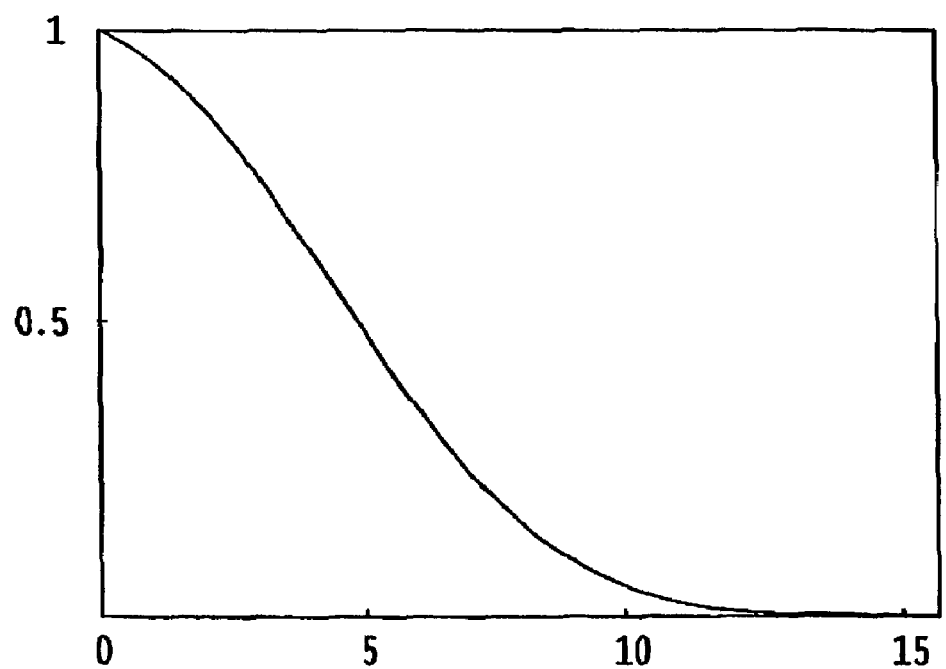

FIG. 2 shows the configuration of an optical system of a light source unit used in the first embodiment of the present invention. The optical system includes a lens system 55 which reduces and projects the image of an aperture window of a lamp 6, and a lens system 56 which condenses the light flux of the lamp onto an end surface 12 of a light guide of the scope. The lamp 6 used in this embodiment is a discharge-type xenon lamp. The xenon lamp is positioned at the focus of a parabolic mirror and projects the image of a bright spot formed near the tip of the negative electrode to infinity. Note that because the bright spot of the lamp is not a perfect point source but instead has a finite size, the light flux reflected by the parabolic surface is projected not as a collimated beam but instead has some beam spread. FIGS. 3(a) and 3(b) show illumination distributions of a light beam emerging from the aperture window of the xenon lamp, with FIG. 3(a) being the illumination distribution when the accumulated usage time is about six hours, and FIG. 3(b) being the illumination distribution when the accumulated usage time is about 100 hours. According to the illumination distribution of light shown in FIG. 3(a), the illumination angle (as measured on the X-axis) where the intensity (measured on the Y-axis) decreases to 0.5 of the maximum intensity is about 3°. Because the shape of this illumination distribution is almost a Gaussian distribution, it can be understood that the light flux within a half-beam width of 3° encompasses about 75% of the total light flux.

Also, according to the illumination distribution of the light shown in FIG. 3(a), the illumination angle (as measured on the X-axis) where the intensity (measured on the Y-axis) decreases to 0.2 of the maximum intensity is about 5°. It can be understood that most of the light flux is encompassed within a half-beam angle of 5°, and thus there is little light flux emitted at angles larger than 5°. Also, from the illumination distribution shown in FIG. 3(b), it can be understood that the illumination distribution of a xenon lamp spreads out when the accumulated usage time exceeds 100 hours. In this case, the illumination angle where the relative intensity to the central illumination intensity becomes 0.5 is about 5°. This is due to the tip of the negative electrode being consumed with lamp usage, resulting in the bright spot that is formed near the tip of the negative electrode changing position as the lamp ages.

Figure 4A:
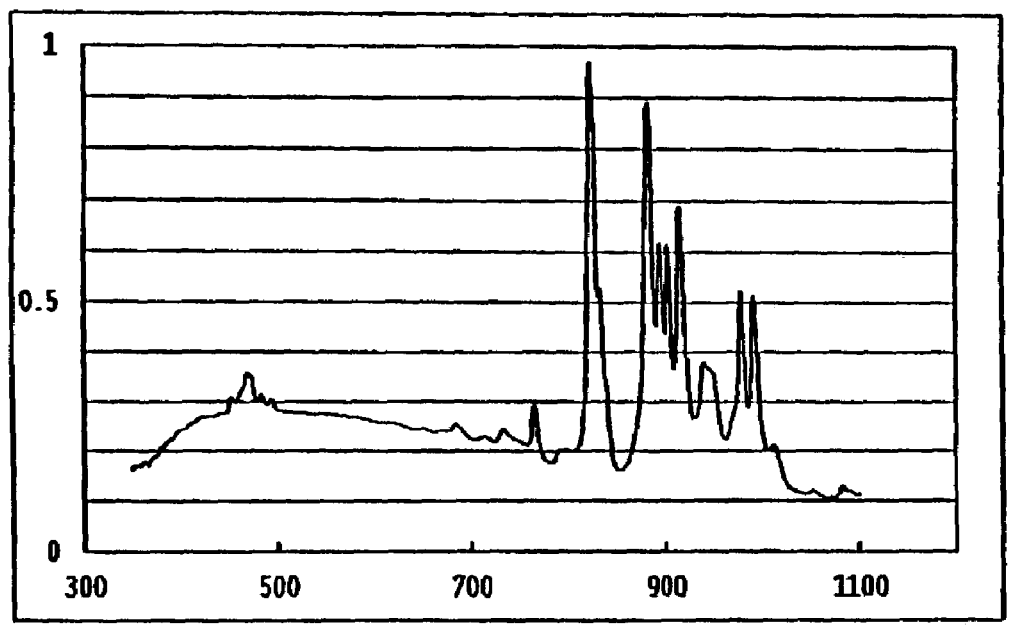
FIGS. 4(a) and 4(b) show the emission intensity distribution of a xenon lamp used in Embodiment 1, with FIG. 4(a) being the emission intensity distribution (Y-axis, arbitrary units) plotted against emitted wavelength (X-axis in nm), when the accumulated usage time is about six hours, and with FIG. 4(b) being the emission intensity distribution when the accumulated usage time is about 100 hours.
Figure 4B:
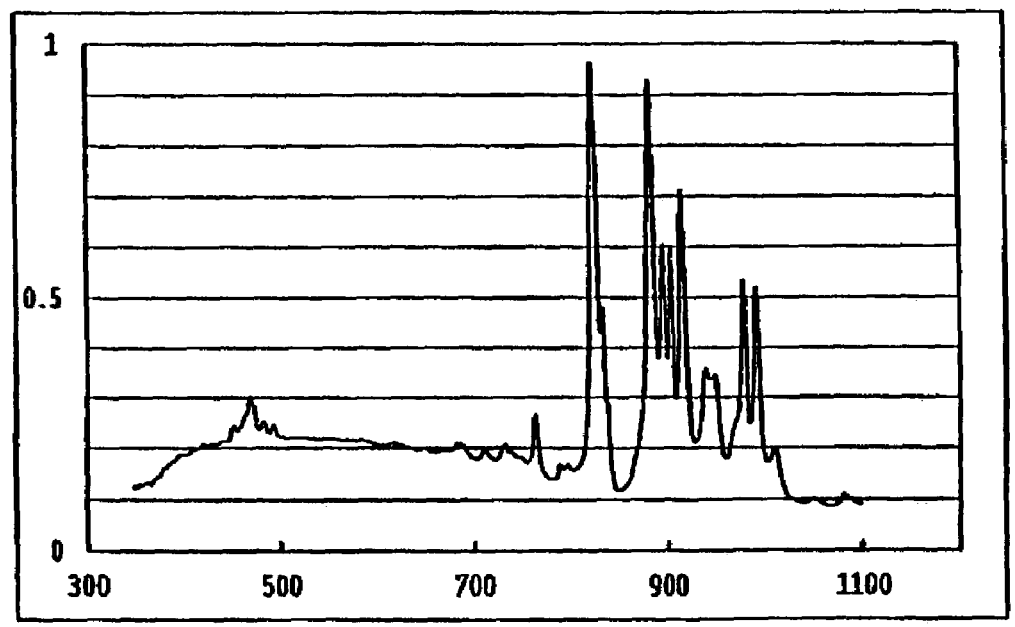

As shown in FIGS. 4(a) and 4(b), a xenon lamp has an emission intensity distribution which is flat in the visible wavelength region, with FIG. 4(a) being the emission intensity distribution when the accumulated usage time is about six hours, and FIG. 4(b) being the emission intensity distribution when the accumulated usage time is about 100 hours. Because the xenon lamp has sufficient intensity also in the ultraviolet wavelength region and the infrared wavelength region, it is the most suitable lamp for use where multiple special light observations such as observing using an ordinary color image observation and an infrared image observation are performed with one endoscope apparatus, as in the present invention. Also, xenon lamps have an illumination intensity distribution that is stable (i.e., without large changes in the relative shape of the illumination intensity distribution) in each of the wavelength regions even when the accumulated usage time has exceeded 100 hours. This is important for the endoscope apparatus of the present invention, which performs observations of in vivo tissues using light in very narrow wavelength regions. Thus, stable observation images can be obtained without being subject to degradation of the illumination light over time. Note that in FIGS. 4(a) and 4(b), the ultraviolet wavelength region is from 330 nm to 380 nm, the visible wavelength region is from 380 nm to 680 nm, and the infrared wavelength region is from 680 nm to 1100 nm.

As shown in FIG. 1, the optical filters 7b are placed on a turret 9 and a rotary filter wheel 10. Both the turret 9 and the rotary filter wheel 10 are placed in a light path extending from a xenon lamp 6 via a lens system to an incident end surface 12 of a light guide 11 that is used with a scope 3. The design is such that the turret 9 moves along a plane that is perpendicular to the optical axis of the light source optical system and the rotary filter wheel 10 rotates about an axis that is parallel to the optical axis. Ideally, light rays traveling along the optical axis are incident onto the optical filters 7b at an angle of incidence of zero degrees, as measured relative to the surface normal of the optical filters 7b.However, because there are mechanical errors in the movement mechanism 23 of the turret 9 and the rotation mechanism 22 of the rotary filter wheel 10, it is not possible to make the movement plane of the turret 9 perfectly perpendicular to the optical axis or the rotation axis of the rotary filter wheel 10 perfectly parallel to the optical axis. Therefore, the optical filters 7b may end up being inserted somewhat obliquely to the optical axis of the light source optical system. The light ray that is parallel to the optical axis is incident onto the optical filter 7b at an incident angle of about 8°.

The optical filters 7b are made by having parallel-plate-shaped optical elements coated with multiple interference films. These have a property to transmit light belonging to a specific wavelength region and to reflect light of other wavelengths. In general, optical filters such as the above change their transmittance properties corresponding to the incidence angle of the light beam incident to the coating surface. This transmittance property is best when the light incidence angle is 0° and degrades as the incidence angles increase. As shown in FIGS. 5(a)-5(e), as the incidence angle of a light beam incident to the coating surface increases, the transmitted wavelength region shifts to the shorter wavelength side, and a desired transmittance property cannot be obtained.

Figure 5A:
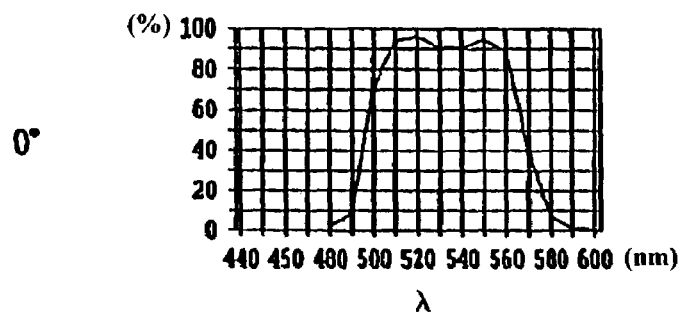
FIGS. 5(a)-5(e) show the relationship between the incidence angle of a light beam that is incident onto a general multilayer interference film and the spectral transmittance properties of the multilayer interference film, with FIG. 5(a) being the spectral transmittance for an incidence angle of 0°, FIG. 5(b) being the spectral transmittance for an incidence angle of 10°, FIG. 5(c) being the spectral transmittance for an incidence angle of 20°, FIG. 5(d) being the spectral transmittance for an incidence angle of 30°, and FIG. 5(e) being the spectral transmittance for an incidence angle of 40°.
Figure 5B:
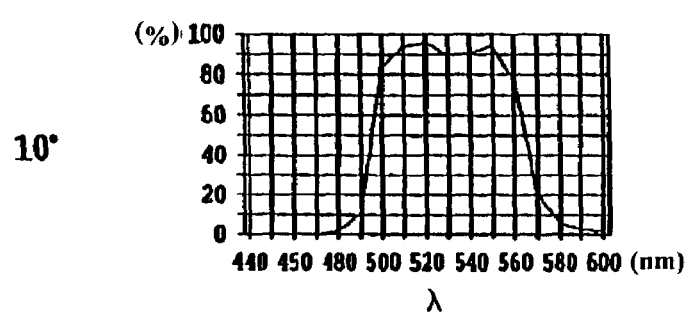
Figure 5C:
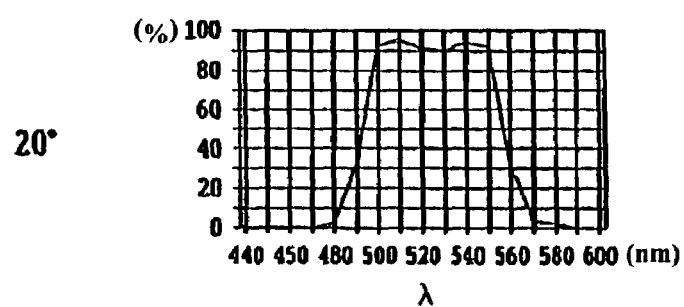
Figure 5D:
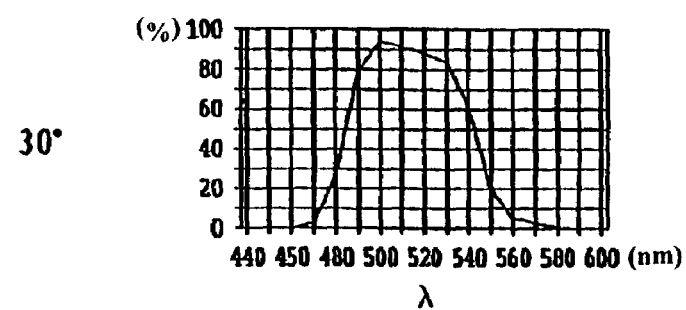
Figure 5E:
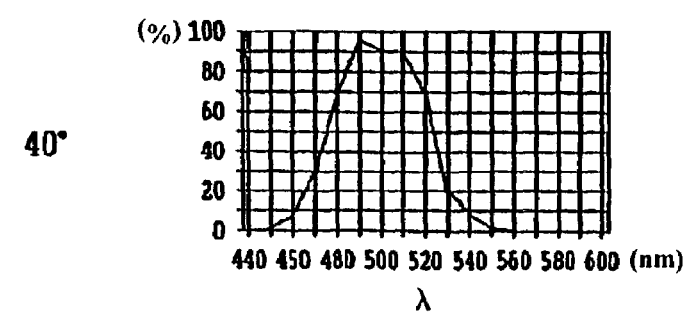

As can be seen by comparing the spectral transmission curve of FIGS. 5(b) versus that of FIG. 5(a), the amount of shifting to shorter wavelengths of the transmitted light of the optical filter is about 5 nm when the light is incident at 10° (FIG. 5(b)) versus 0° (FIG. 5(a)). Therefore, in the light source unit of the present invention, the turret 9 and the rotary filter wheel 10 are placed in the light path of the light source unit at a position wherein the following Condition (7) is satisfied:

$$\theta \leq 13°$$ Condition (7)

where θ is the incidence angle of a light ray onto the optical filters 7b that are positioned on the turret 9 and the rotary filter wheel 10.

More specifically, the turret 9 is placed immediately after the xenon lamp. The illumination distribution of a light beam emerging from the aperture window of a xenon lamp with an accumulated usage time that exceeds 100 hours is shown in FIG. 3(b), where 75% of the emitted light lies within an angle of 5° to the optical axis. The positioning of the optical filters of the turret in the light path is such that, for light rays emitted by the light source unit within an angle of 5° to the optical axis, the maximum angle of incidence onto the optical filters is less than 13°. Thus, the optical filters 7b can stably transmit light in the desired wavelength region, independent from the lamp usage time. Also, the rotary filter wheel 10 is placed immediately after the lens system 55 which projects a reduced image of the aperture window of the xenon lamp. Because the aperture window corresponds to the exit pupil of the xenon lamp, the light illumination distribution immediately after the lens system 55 is equivalent to the illumination distribution shown in FIGS. 3(a) and 3(b). Therefore, the incidence angle of a light beam to the optical filters 7b placed on the rotary filter wheel 10 can also be set to the same condition as the optical filters 7b placed on the turret 9.

Figure 6A:
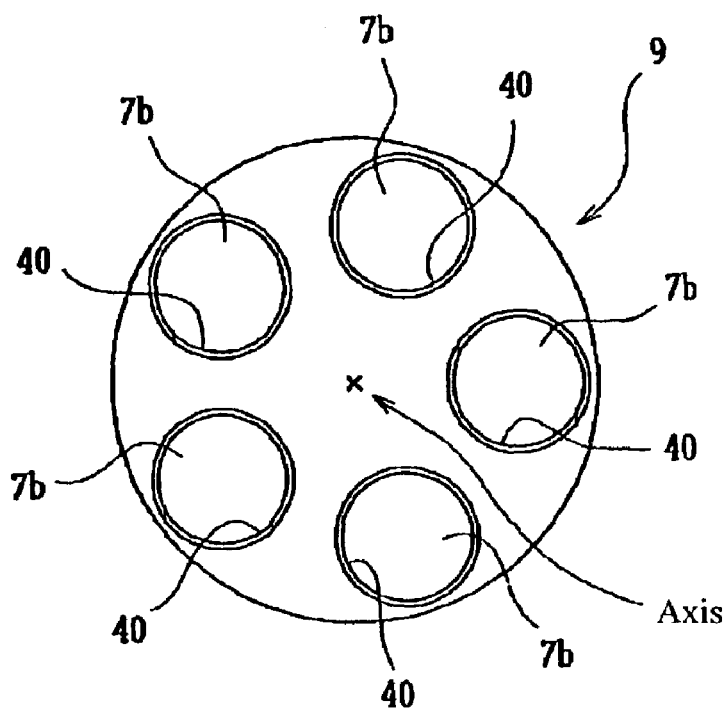
FIG. 6(a) shows a front view (as seen along the rotation axis) of a filter holder that is placed within a turret used in the light source optical system of Embodiment 1.
Figure 6B:
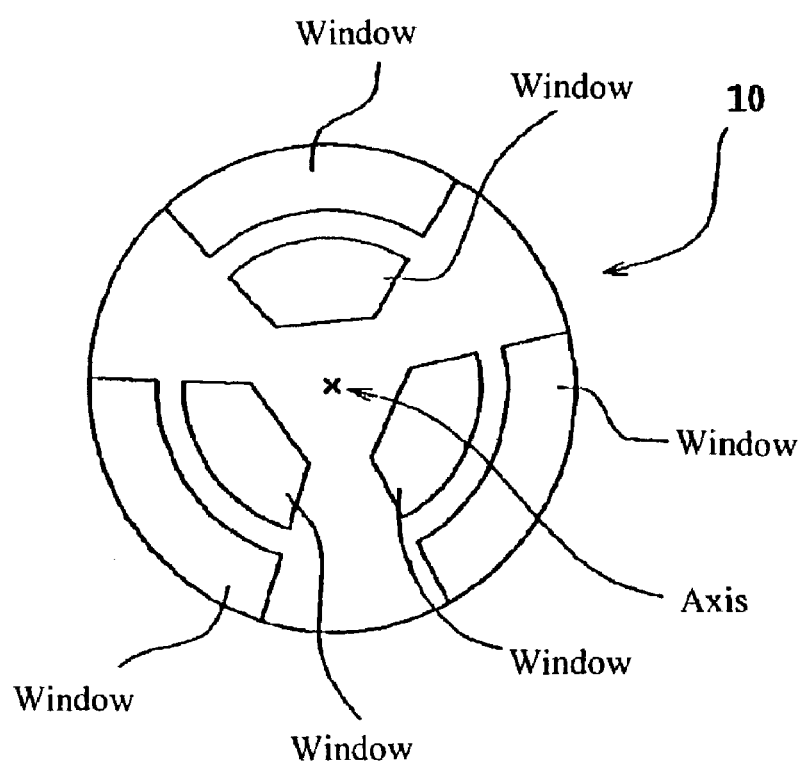
FIG. 6(b) shows the layout of filter windows that are placed on a rotary filter wheel that is used in the light source optical system of Embodiment 1.

As shown in FIG. 6(a), in the turret 9, there are at least five filter holders 40 placed concentrically on the substrate, and one or more optical filters 7b are put in the filter holders. By rotating the turret 9 about its center axis, the optical filters put in the filter holders 40 are inserted into the light path and fixed. As shown in FIG. 6(b), the rotary filter wheel 10 has windows installed concentrically within an outer region and an inner region on a substrate, and the optical filters are adhered to the substrate so as to be positioned, one each, at the windows. The rotary filter wheel 10 is rotated about its center axis at a constant rotation speed. Also, the rotary filter wheel 10 moves substantially perpendicularly to the optical axis of the light source optical system by a rotary filter wheel movement mechanism, not shown. By moving the rotary filter wheel 10 to selected positions, the following three illumination conditions can be selectively created.

Illumination Condition 1—A series of optical filters installed in the outer circle of the rotary filter wheel are sequentially inserted into the light path and perform illumination repeatedly.

Illumination Condition 2—A series of other optical filters installed in the inner circle of the rotary filter wheel are sequentially inserted into the light path and perform illumination repeatedly.

Illumination Condition 3—Illumination is performed with the rotary filter wheel withdrawn from the light path.

Therefore, if five kinds of optical filters having different transmittance properties are installed on the turret 9, it is possible to create 15 different illumination conditions by combining the turret 9 and the rotary filter wheel 10. The rate of rotation of the rotary filter wheel 10 is able to be changed so that a different rotation period can be made to correspond to each of the 15 different possible illumination conditions.

The optical filters allow light in a specific narrow wavelength range to be selectively transmitted according to the particular combination of optical filters selected. In a special light observation, by irradiating light in the specific narrow wavelength range to an in vivo tissue, image information of the in vivo tissue derived from light in the specific narrow wavelength range is obtained as reflected light from the in vivo tissue. For example, it is possible to select light in an arbitrary, narrow wavelength range with the wavelength being less than 470 nm as the excitation light, to irradiate a in vivo tissue with the excitation light so as to induce self-fluorescence of the in vivo tissue, and to obtain fluorescent image information of the in vivo tissue. Other than the self-fluorescence of in vivo tissue, the fact that fluorescent medicines such as ALA (5-aminolevulinic acid) are absorbed only by lesions of in vivo tissues can be utilized to produce fluorescence of in vivo lesions. Also, a metabolic contrast medium can be used. In this case, when a contrast medium is absorbed by in vivo tissue, it reacts with materials that accumulate only in lesions and secondary products are generated. Because the products emit fluorescence by reacting to excitation light, the lesions can be precisely distinguished from normal tissue.

It is possible to select light in an arbitrary, narrow wavelength range within visible wavelengths from 380 nm to 680 nm, and to irradiate in vivo tissues with this light so as to obtain information about the in vivo tissues in the depth direction. Light of short wavelengths in the visible range which belongs to the blue wavelength region only reaches depths very near to the surface of the in vivo tissue. By utilizing this fact, information specifically concerning the mucosa surface layer of a living body can be obtained. In the same way, because light of wavelengths near 500 nm (i.e., the green wavelength region) reaches a depth that is a little deeper than the surface layer of the in vivo tissue, and longer wavelengths (i.e., the red wavelength region) reach depths that are relatively deep in the in vivo tissue, information specific to each desired depth can be obtained.

In addition, it is possible to select infrared radiation in an arbitrary narrow wavelength range anywhere within the wavelength range of 680 nm to 1100 nm, and to irradiate living body tissue with such infrared radiation so as to obtain information from the lower layer of the mucosa of the living body tissue. Near the lower layer of the mucosa of the living body tissue, relatively thick blood vessels and lymphatics exist. Then, by injecting indocyaninegreen (ICG) etc., which has an absorption peak in the near-infrared region, to the blood vessels and lymphatics as a contrast medium, the blood vessels and lymphatics can be clearly observed.

Of course, the lens that is used to condense the light from the light source, which the optical filters selectively transmit in arbitrary narrow wavelength ranges, must efficiently condense the light onto the incident end surface of the light guide. If the condensing efficiency of the light source lens is poor, there will be an insufficient amount of illumination light and the special light observations described above will not be possible. Therefore, on the surface of the light source lens of the present invention, a multilayer film coating is provided that meets the above Conditions (2)-(5).

On the surfaces of conventional light source lenses, there often is provided a coating which prevents reflection of a narrow range of light limited mainly to the visible wavelengths. However, in the light source unit of the present invention, because multiple kinds of special light observations are performed utilizing light in a wide wavelength range of 330 nm to 1100 nm as described above, if a conventional anti-reflective coating is used, the amount of illumination light in the special light observations utilizing light other than in the visible wavelength range will be insufficient. By using a multilayer film coating having the reflectance properties as specified in Conditions (2)-(5) above, brightness can be secured for the multiple kinds of special light observations.

An illumination window and an observation window are installed at the tip of the scope. In the illumination window an illumination unit is installed that is equipped with a light guide and an illumination lens. The imaging unit includes an objective lens, a filter, an image sensing chip, and a channel through which may be inserted a treatment tool for removing a lesion of a living body. An example of such a treatment tool is a probe that guides the beam from an external laser source that is used for burning the lesion.

As stated above, although a countermeasure is taken in the light source unit so that the amount of illumination light for special light observations will not become insufficient, it is still inevitable that the illumination will be insufficient as compared with the amount of illumination needed for ordinary color image observations. Therefore, there needs to be a countermeasure taken on the imaging unit side for ordinary color image observations which compensates for the illumination insufficiency. For example, the F-number of the objective lens may be decreased in order to secure as bright an observation image as possible using light which is reflected by the object and reaches the reception surface of the image sensing chip. However, if the F-number of the objective lens is decreased, the depth of field becomes narrower, and this may cause a problem when simultaneously attempting to observe details at different depths.

Figure 7:
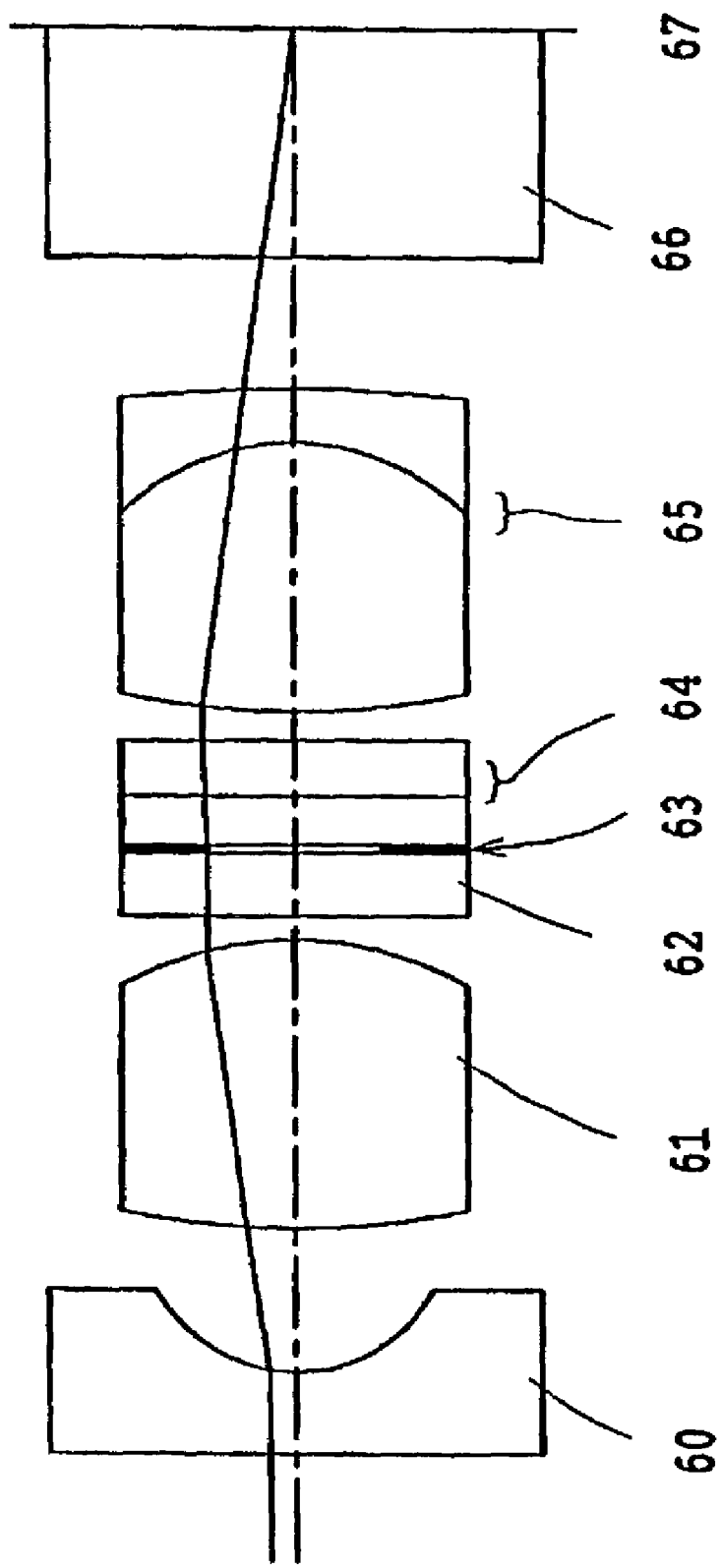
FIG. 7 shows an example of an imaging unit that may be used in Embodiment 1.
Figure 9:
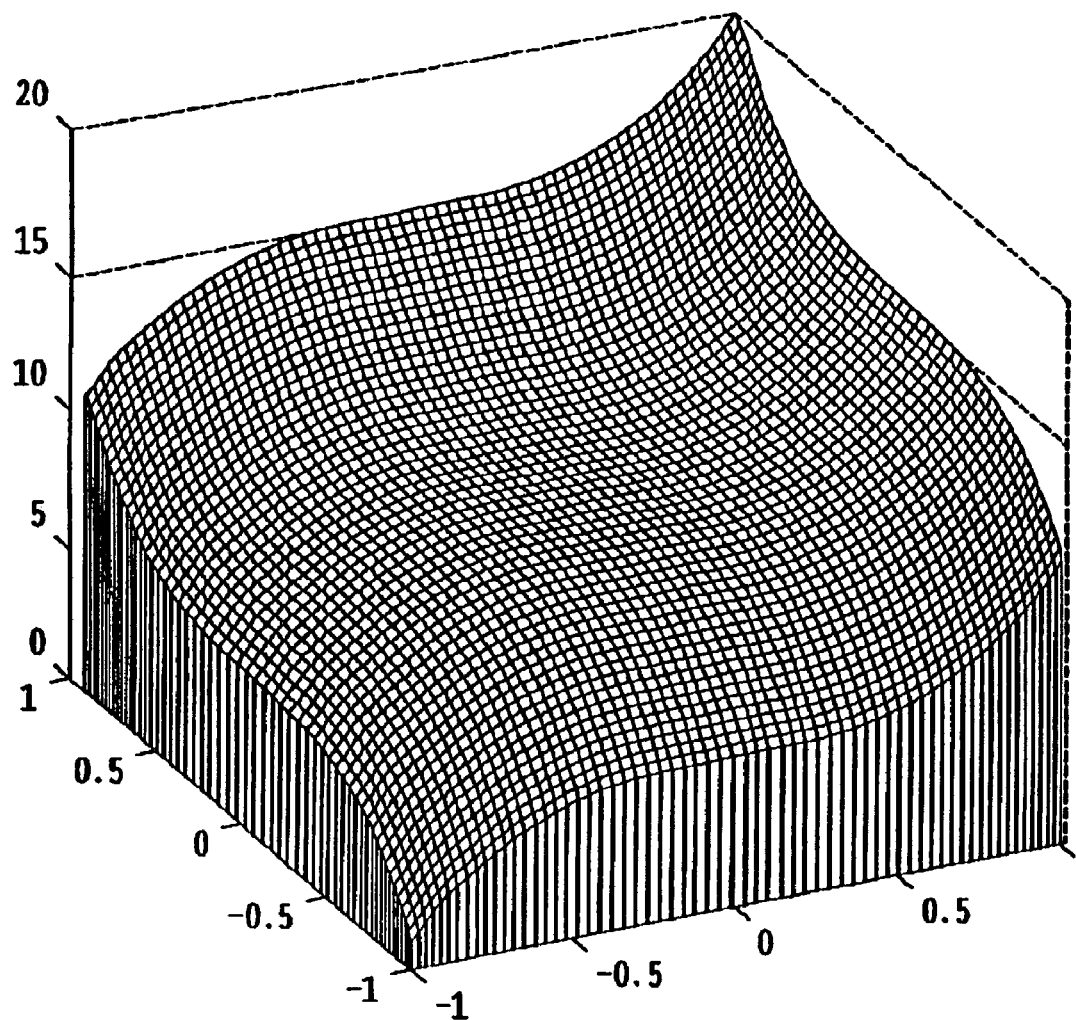
FIG. 9 is a perspective view showing the external shape of a prior art optical phase mask that is used in the device illustrated in FIG. 8.

FIG. 7 shows an example of an imaging unit which may be used. Near the aperture stop of the objective lens, a spatial frequency conversion means 62, such as a phase mask as shown in FIG. 9, is installed. The image signal obtained by the image sensing chip via the spatial frequency conversion means 62 is image processed in a signal processing circuit which performs restoration of the spatial frequencies, thereby enabling the depth of field to be increased. Such a method of increasing the depth of field of an imaging optical system is disclosed in U.S. Pat. No. 5,748,371,the teachings of which are hereby incorporated by reference.

Figure 8:
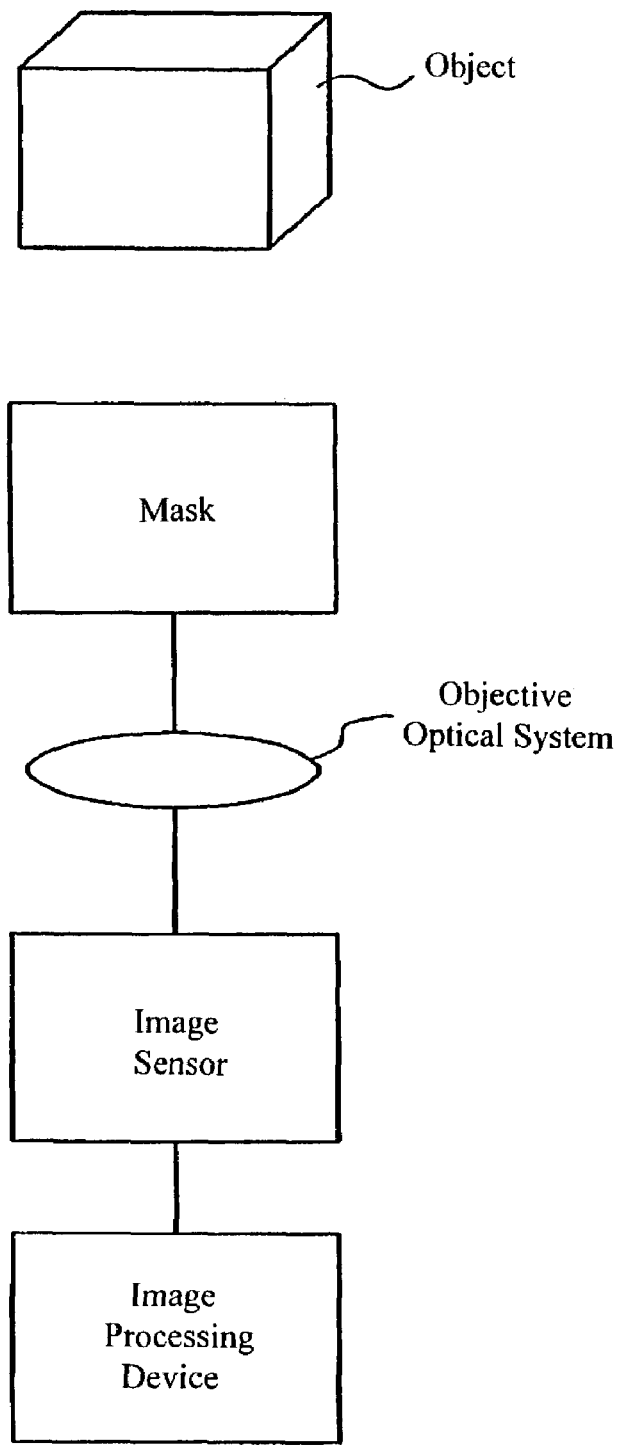
FIG. 8 shows the configuration of components of a prior art device that is used to increase the depth of field.
Figure 10:
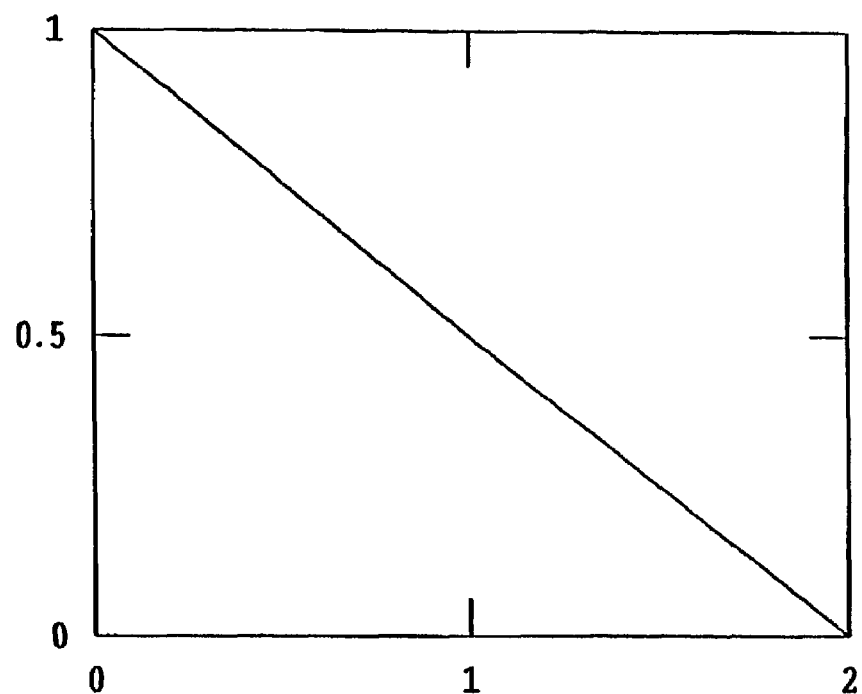
FIG. 10 shows the intensity distribution of the optical transfer function (Y-axis) plotted against relative spatial frequency (X-axis) when an object is at an in-focus position of an ordinary optical system, with 2 on the X-axis being the Nyquist frequency of the image sensing chip.

FIG. 8 illustrates an apparatus that uses the method disclosed in U.S. Pat. No. 5,748,371.This apparatus has an image sensor such as a CCD, an optical system such as a lens which forms an image of an object on the reception surface of the image sensor, an optical phase mask that is located at the pupil position of the optical system, and an image processing device which constructs an image based on image data received from the image sensor. The shape of the optical phase mask is shown in FIG. 9. In an ordinary imaging optical system which does not have a phase mask, the intensity distribution of the optical transfer function (OTF) at the image plane of the imaging optical system changes from the shape shown in FIG. 10 to the shape shown in FIG. 11 as the object moves from the in-focus position to a position away from the in-focus position. If the object moves away from the in-focus position even farther, it changes to the shape shown in FIG. 12.

Figure 11:
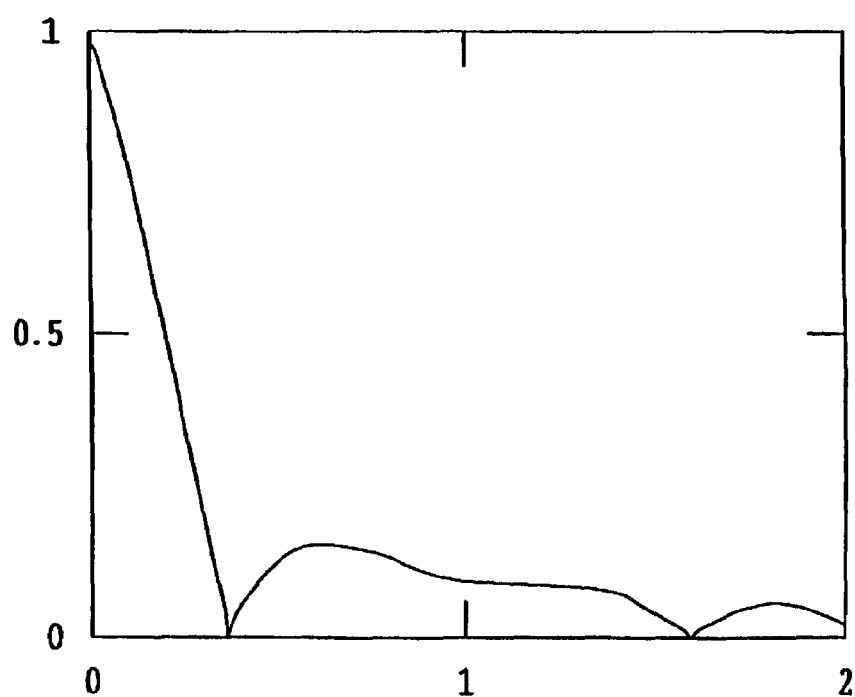
FIG. 11 shows the intensity distribution of the optical transfer function (Y-axis) plotted against relative spatial frequency (X-axis) when an object is positioned somewhat away from the in-focus position of an ordinary optical system, with 2 on the X-axis being the Nyquist frequency of the image sensing chip.
Figure 12:
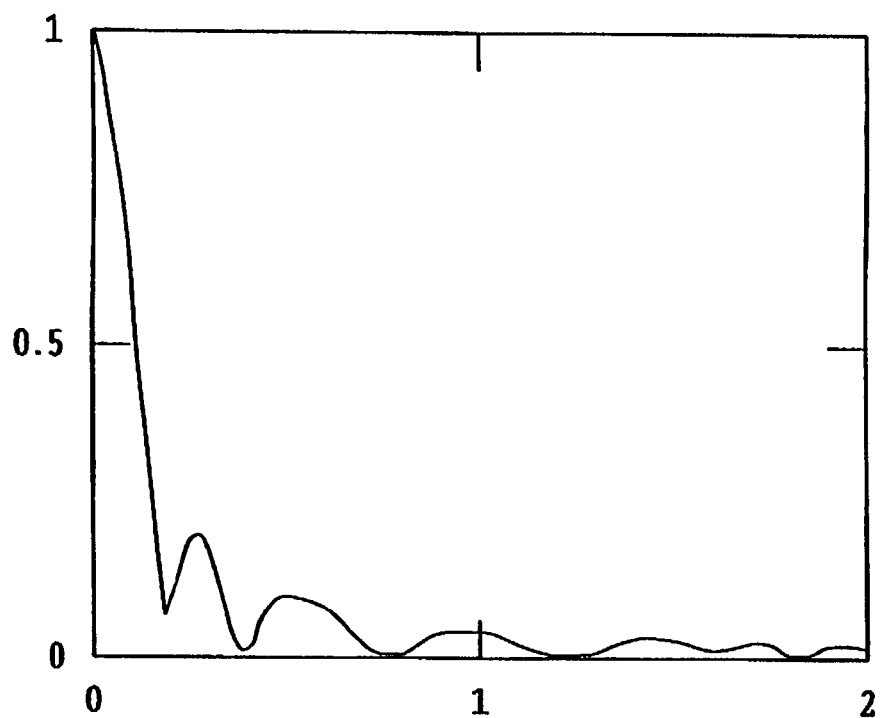
FIG. 12 shows the intensity distribution of the optical transfer function (Y-axis) plotted against relative spatial frequency (X-axis) when an object is positioned farther away from the in-focus position of an ordinary optical system than that shown in FIG. 11, with 2 on the X-axis being the Nyquist frequency of the image sensing chip.
Figure 13:
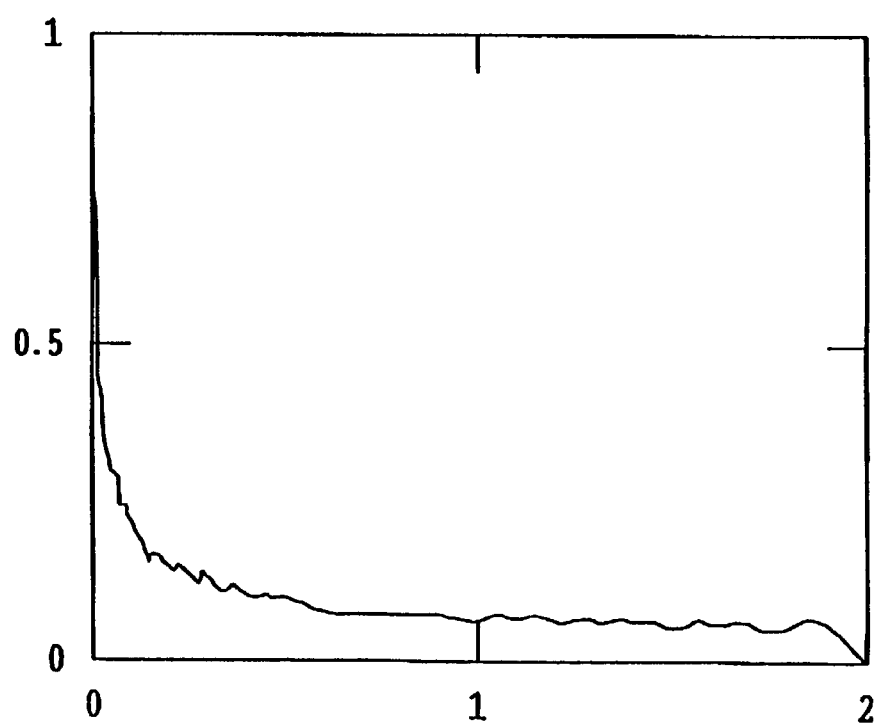
FIG. 13 shows the intensity distribution of the optical transfer function (Y-axis) plotted against relative spatial frequency (X-axis), with 2 on the X-axis being the Nyquist frequency of the image sensing chip, when an object is at an in-focus position in an optical system wherein the depth of field has been increased using a phase mask as shown in FIG. 9.
Figure 14:
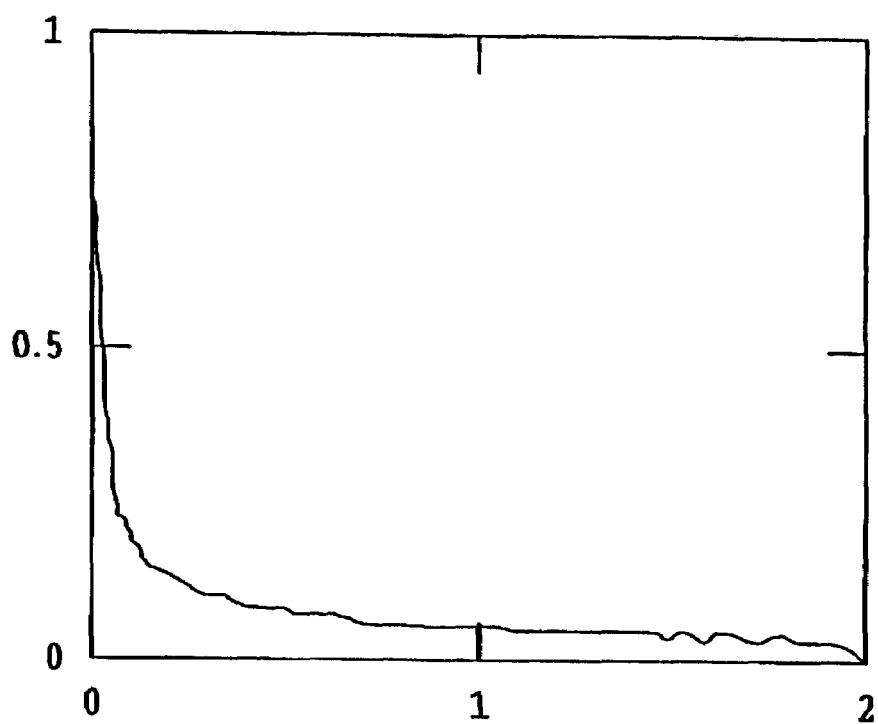
FIG. 14 shows the intensity distribution of the optical transfer function (Y-axis) plotted against relative spatial frequency (X-axis), with 2 on the X-axis being the Nyquist frequency of the image sensing chip, when an object is positioned somewhat away from an in-focus position of an optical system wherein the depth of field has been increased using a phase mask as shown in FIG. 9.
Figure 15:
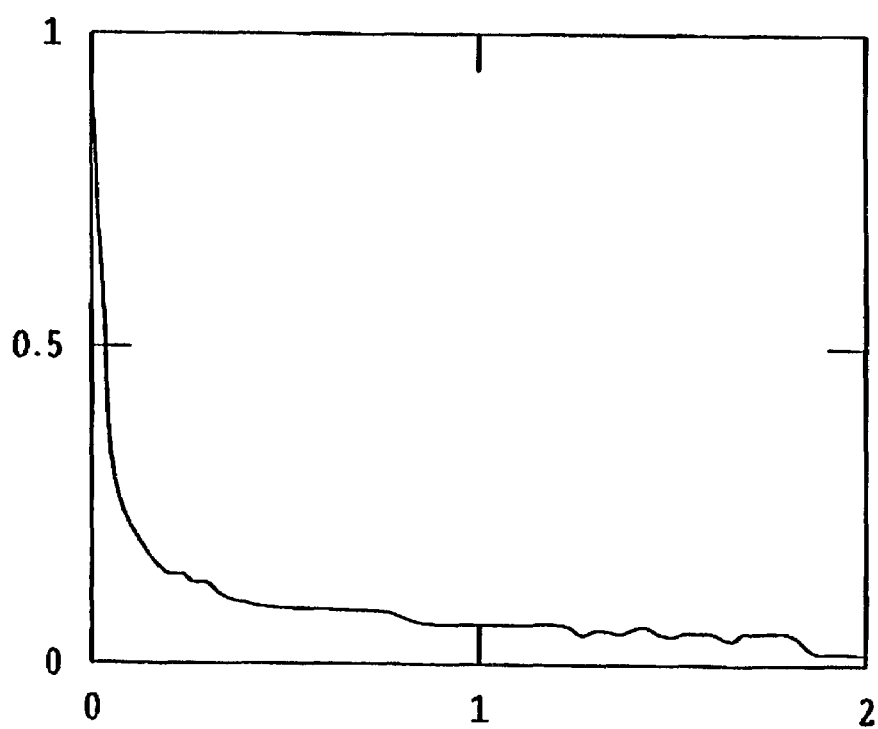
FIG. 15 shows the intensity distribution of the optical transfer function (Y-axis) plotted against relative spatial frequency (X-axis), with 2 on the X-axis being the Nyquist frequency of the image sensing chip, when an object is positioned farther away from an in-focus position than that shown in FIG. 14.
Figure 16:
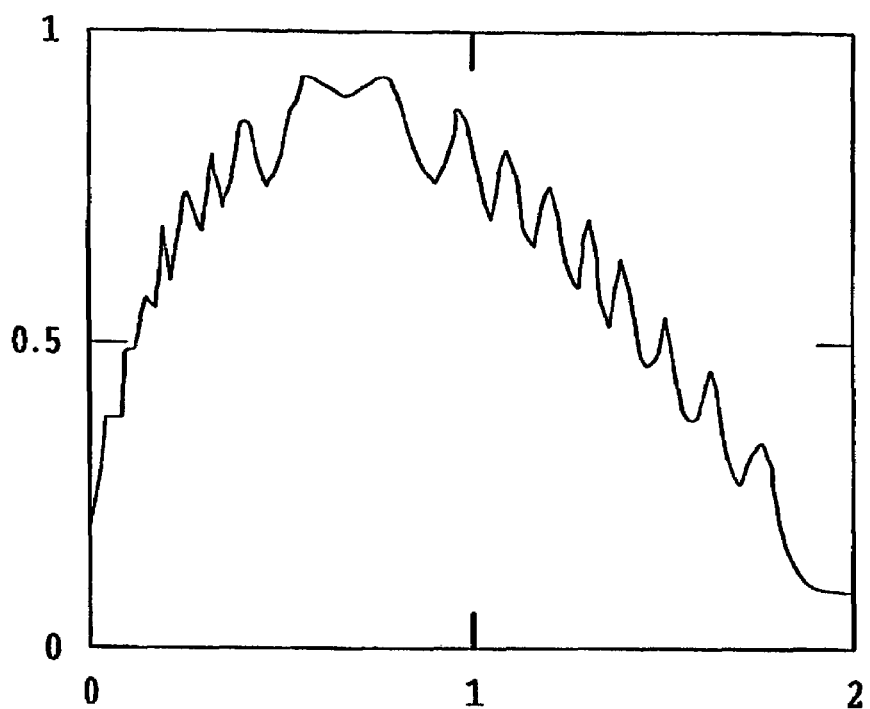
FIG. 16 shows the intensity distribution of the optical transfer function (Y-axis) plotted against relative spatial frequency (X-axis), with 2 on the X-axis being the Nyquist frequency of the image sensing chip, of a filter used in a spatial frequency restoration processing performed in a depth of field magnified optical system.

On the other hand, in a so-called 'depth of field magnified optical system' which combines an optical system having the same optical performance as the imaging optical system and the optical phase mask shown in FIG. 9, the intensity distribution of the OTF at the image plane of the depth of field magnified optical system becomes as shown in FIG. 13 for an object at the in-focus position. When the object moves from the in-focus position by an amount equal to that for which the OTF is shown in FIG. 11, the OTF of a depth of field magnified optical system becomes as shown in FIG. 14. When the object moves still farther from the in-focus position by an amount equal to that for which the OTF is shown in FIG. 12, the OTF of a depth of field magnified optical system becomes as shown in FIG. 15. In each of FIGS. 10-19, the horizontal axis represents relative spatial frequency, with "2" corresponding to the Nyquist frequency of the image sensing chip, and the vertical axis represents the optical transfer function of the imaging optical system. For images formed on the image sensor by the depth of field magnified optical system, image restoration processing is performed by the image processing device. Namely, filtering using a spatial frequency restoration filter having an OTF as shown in FIG. 16 is performed on the OTF intensity distributions shown in FIGS. 13, 14, and 15.

Figure 17:
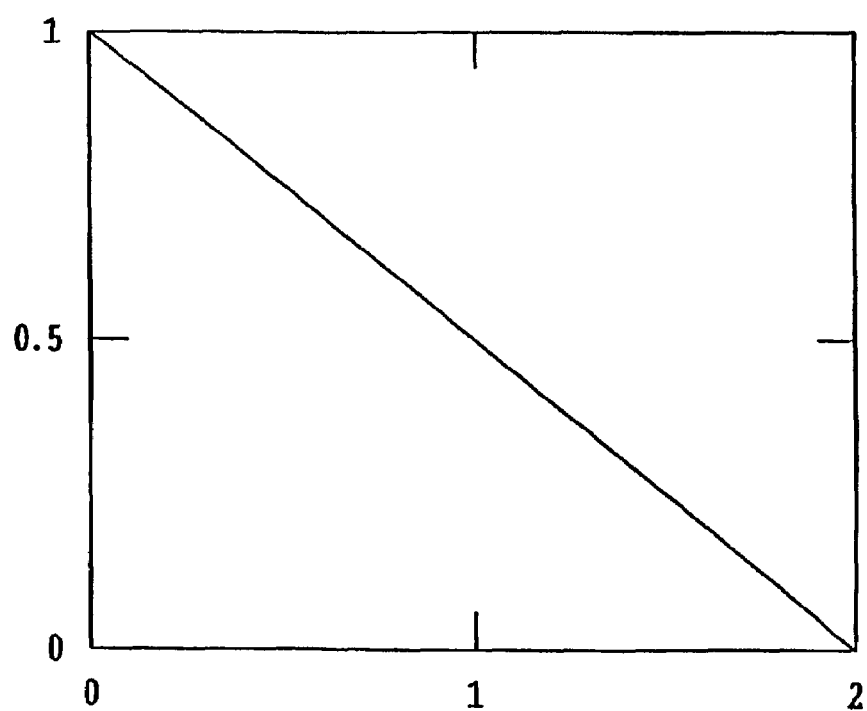
FIG. 17 shows the intensity distribution of the optical transfer function (Y-axis) plotted against relative spatial frequency (X-axis), with 2 on the X-axis being the Nyquist frequency of the image sensing chip, after performing a spatial frequency restoration processing to the optical transfer function shown in FIG. 13 using a filter having the property shown in FIG. 16.
Figure 18:
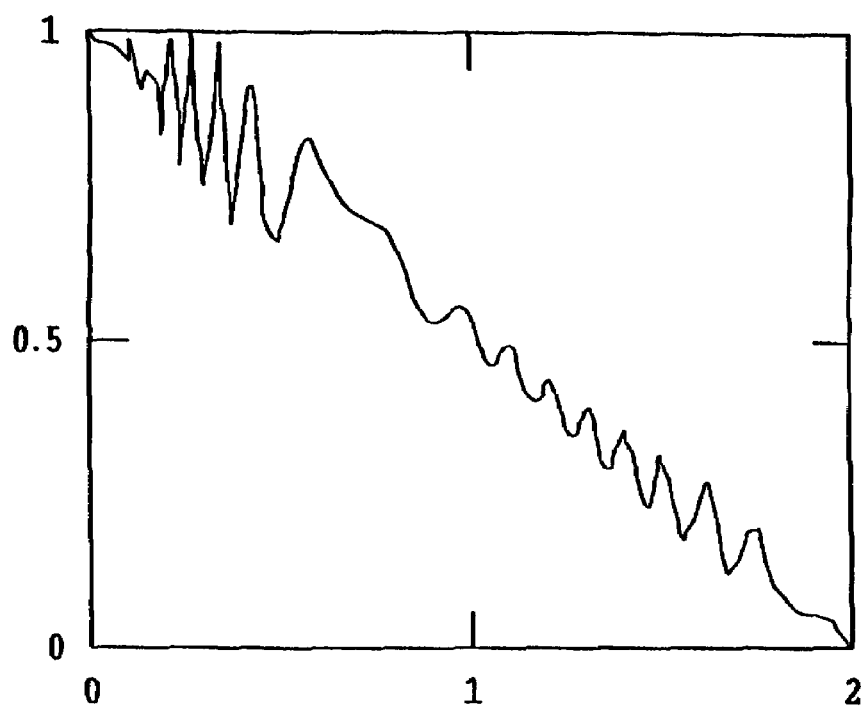
FIG. 18 shows the intensity distribution of the optical transfer function (Y-axis) plotted against relative spatial frequency (X-axis), with 2 on the X-axis being the Nyquist frequency of the image sensing chip, after performing a spatial frequency restoration processing to the optical transfer function shown in FIG. 14 using a filter having the property shown in FIG. 16.
Figure 19:
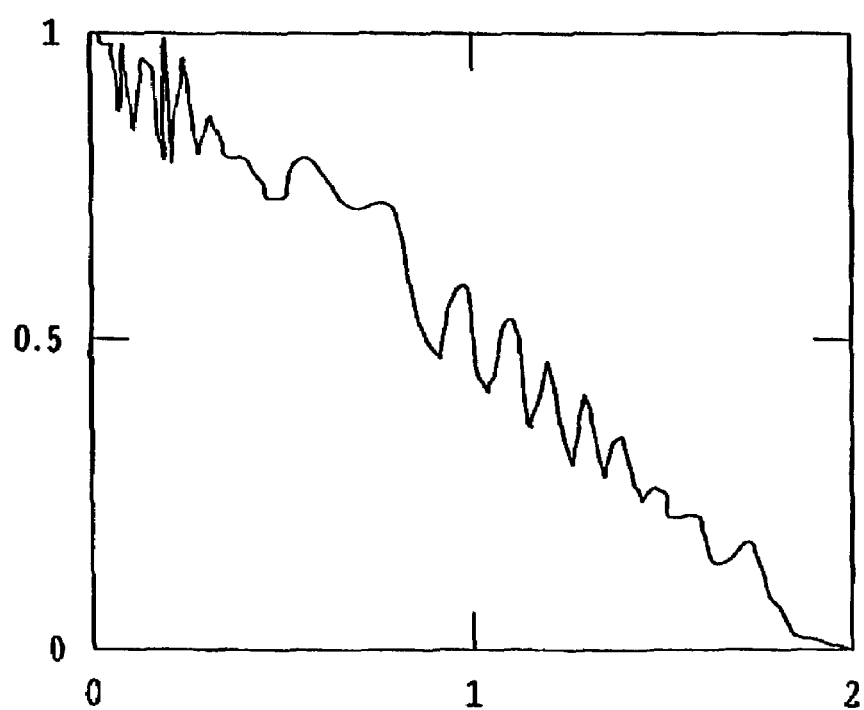
FIG. 19 shows the intensity distribution of the optical transfer function (Y-axis) plotted against relative spatial frequency (X-axis), with 2 on the X-axis being the Nyquist frequency of the image sensing chip, after performing a spatial frequency restoration processing to the optical transfer function shown in FIG. 15 using a filter having the property shown in FIG. 16.

As a result, the OTF intensity distribution shapes are restored, as shown in FIGS. 17, 18, and 19, respectively. All these have intensity distributions that are nearly the same as the OTF intensity distribution at the image plane when an object is at the in-focus position. Therefore, in the objective lens of the invention, the brightness of the images formed on the reception surface of the image sensor can be secured by decreasing the F-number of the objective lens and the depth of field of the objective lens can be increased simultaneously.

In the endoscope apparatus of the invention, the following three kinds of scopes can be used. One of these is a scope wherein a single observation window is installed at the tip of the scope and an imaging unit is installed behind the observation window. Such a scope (not illustrated) is constructed so that an ordinary color image observation or a special light observation can be made by selecting the optical properties of the filters installed in the imaging unit. FIG. 7 shows an example of such an imaging unit that may be used, wherein a single imaging unit can perform two types of observations. This imaging unit is formed of, in sequential order from the object side, a plano-concave lens 60, a biconvex lens 61, a spatial frequency conversion means 62, an aperture stop 63, an optical filter 64 for removing light that is unnecessary for observation, a lens 65 formed of a biconvex lens element that is joined to a meniscus lens element, and an image sensing chip 67. On the image sensing chip 67, a cover glass 66 is installed which protects the reception surface of the image sensing chip. When the imaging unit (FIG. 7) is arranged so as to perform fluorescent image observations, the optical filter 64 functions to block excitation light in the wavelength range which causes the fluorescence. When observing self-fluorescence of a living body tissue, light in an arbitrary narrow wavelength range is selected as excitation light of wavelengths shorter than 470 nm, and the living body tissue is irradiated with it. The living body tissue emits fluorescence having a strong peak in a green color at longer wavelengths than the excitation light. The peak intensity of the fluorescence that living body tissue emits is only 1/500 to 1/100 of the average intensity of the excitation light.

Figure 20:
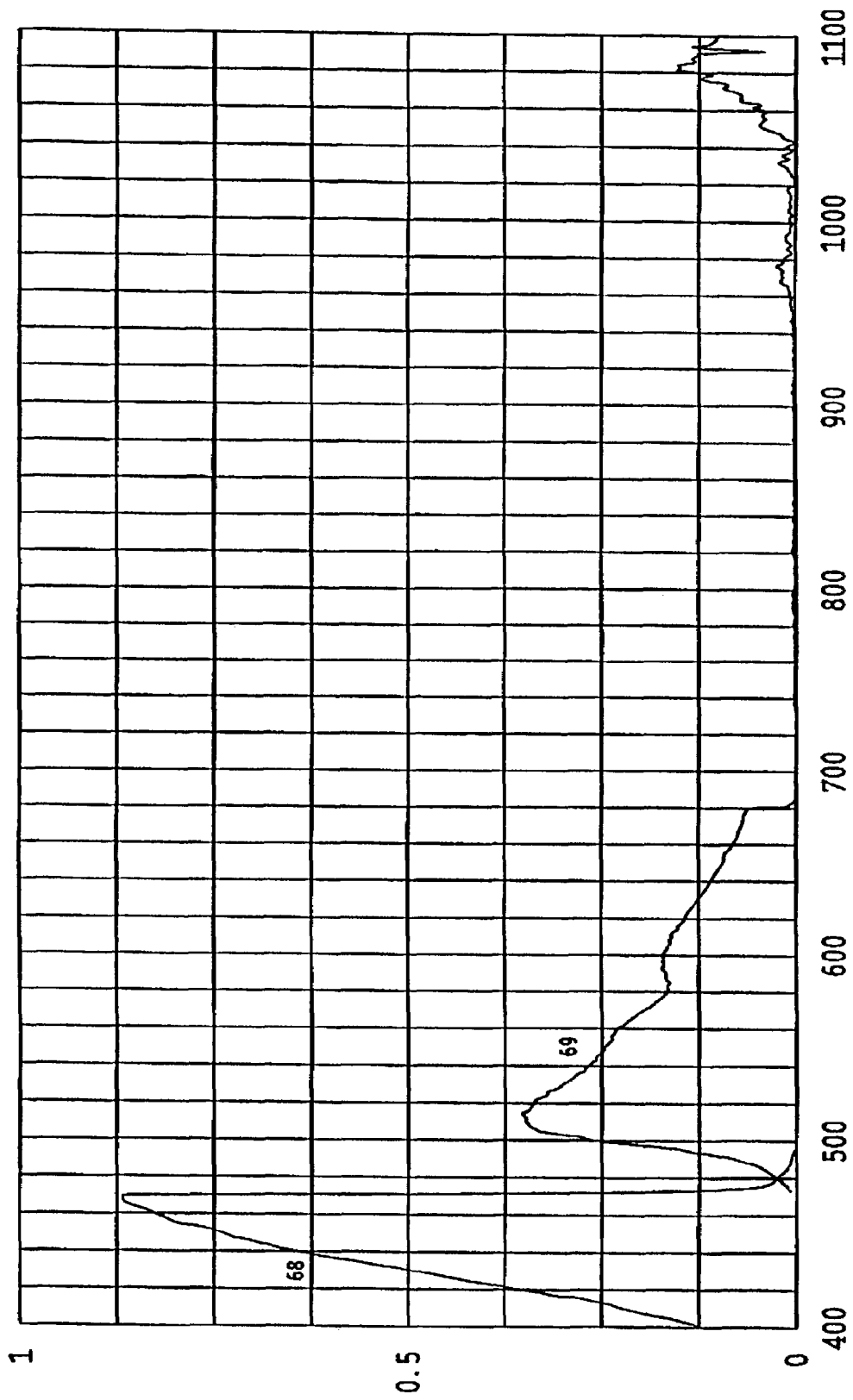
FIG. 20 shows the spectral intensity distribution of excitation light used for artificially induced fluorescent image observations and a 100× magnified spectral intensity distribution of self-fluorescent image observations emitted by in vivo tissue that has been excited by the excitation light.

FIG. 20 shows the spectral intensity emission curves of the excitation light 68 and an example of self-fluorescence 69 emitted by living body tissue. In FIG. 20, the intensity of the self-fluorescent light 69 has been multiplied by a factor of 100 so that the excitation light and the self-fluorescence are easy to compare. The excitation light 68 is irradiated through an illumination unit of the scope to the living body tissue after being passed through a filter installed in the light source unit which transmits light of wavelengths shorter than 470 nm and blocks light of longer wavelengths.

Because the light guide in the illumination unit is generally made of glass fibers, the shorter the wavelength of the light, the more transmission loss occurs in the light guide due to absorption. As a result, the excitation light 68 becomes a blue light which has an intensity peak at 470 nm and the intensity decreases toward shorter wavelengths. The optical filter 64 installed in the scope is a bandpass filter which has a transmittance bandpass range of 500 nm to 680 nm so as to block the excitation light. The self-fluorescence 69 emitted by the living body tissue has an intensity peak near 510 nm.

Thus, when the intensity peaks of the excitation light and the fluorescence are close and their intensity difference is very large, it becomes important that the optical filter 64 has a high excitation light removal performance. If the performance of removing excitation light is insufficient, light which could not be removed by the optical filter 64 reaches the image sensing chip 67 together with the fluorescence. As a result, noise overlaps with the fluorescent image, making the contrast poor. In such a case, clear fluorescent images cannot be obtained.

As stated earlier, an optical filter coated with a multilayer interference film has a transmittance which changes depending on the incidence angle of a light ray that is incident onto its coated surface. Thus, a light ray having an angle of incidence to the optical filter 64 of 0° will be sufficiently blocked. However, light rays with larger incidence angles cannot be sufficiently blocked, resulting in excitation light leakage from the optical filter 64 which will be detected by the image sensing chip 67. Especially when intensity peaks of the excitation light and the fluorescence are near one another in wavelength, the same filter cannot be placed at positions in the imaging unit where incidence angles of the light rays onto the optical filter 64 become large. Thus, in the imaging unit of the present invention, the optical filter 64 is placed in a position where the incidence angles of light rays to the optical filter 64 are small and the imaging unit can be constructed so as to be compact. More specifically, the optical filter 64 is placed in a position so that the light incident onto the optical filter 64 satisfies Condition (6) above.

The imaging unit of an endoscope apparatus must favorably correct even minute aberrations, enable various kinds of optical filters to be selectively inserted in the light path, and provide a wide field of view. Therefore, a telecentric optical system, as shown in FIG. 7 is used in the present invention. In the optical system such as above, positions which satisfy the above Condition (6) for placing the optical filter 64 are locations near the aperture stop and between the lens surface nearest the image side and the image sensing chip 67. Alternatively, the optical filter 64 can be dispersed. For example, the desired excitation light blocking property can be realized using multiple filters placed in different locations.

Figure 21:
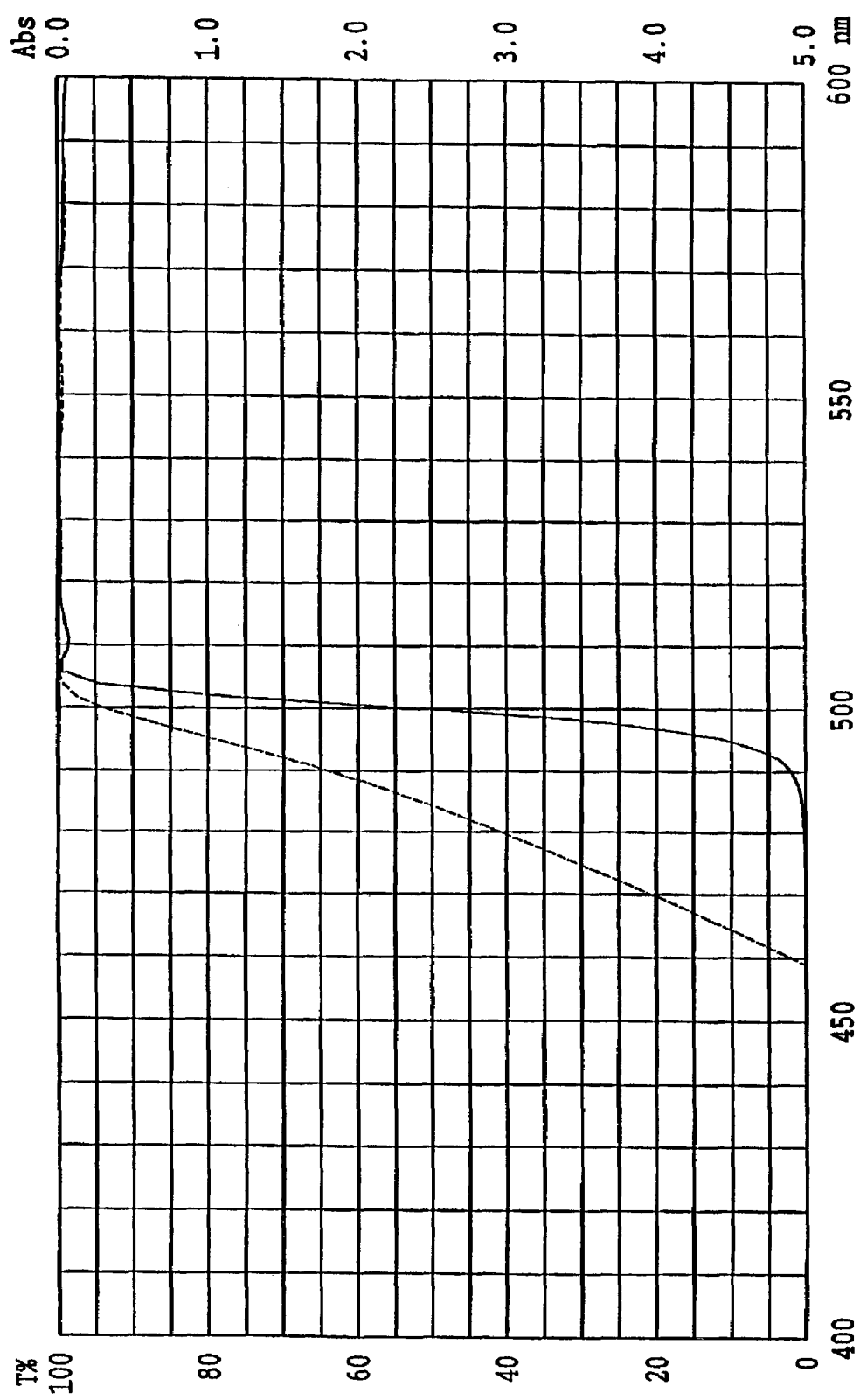
FIG. 21 shows optical properties of a bandpass filter having an excitation light blocking performance that is insufficient for a light beam that is incident normal to the surface of the bandpass filter, with the solid line showing the % transmission as indicated on the left-side scale, and with the dotted line showing the optical density as indicated on the right-side scale.
Figure 22:
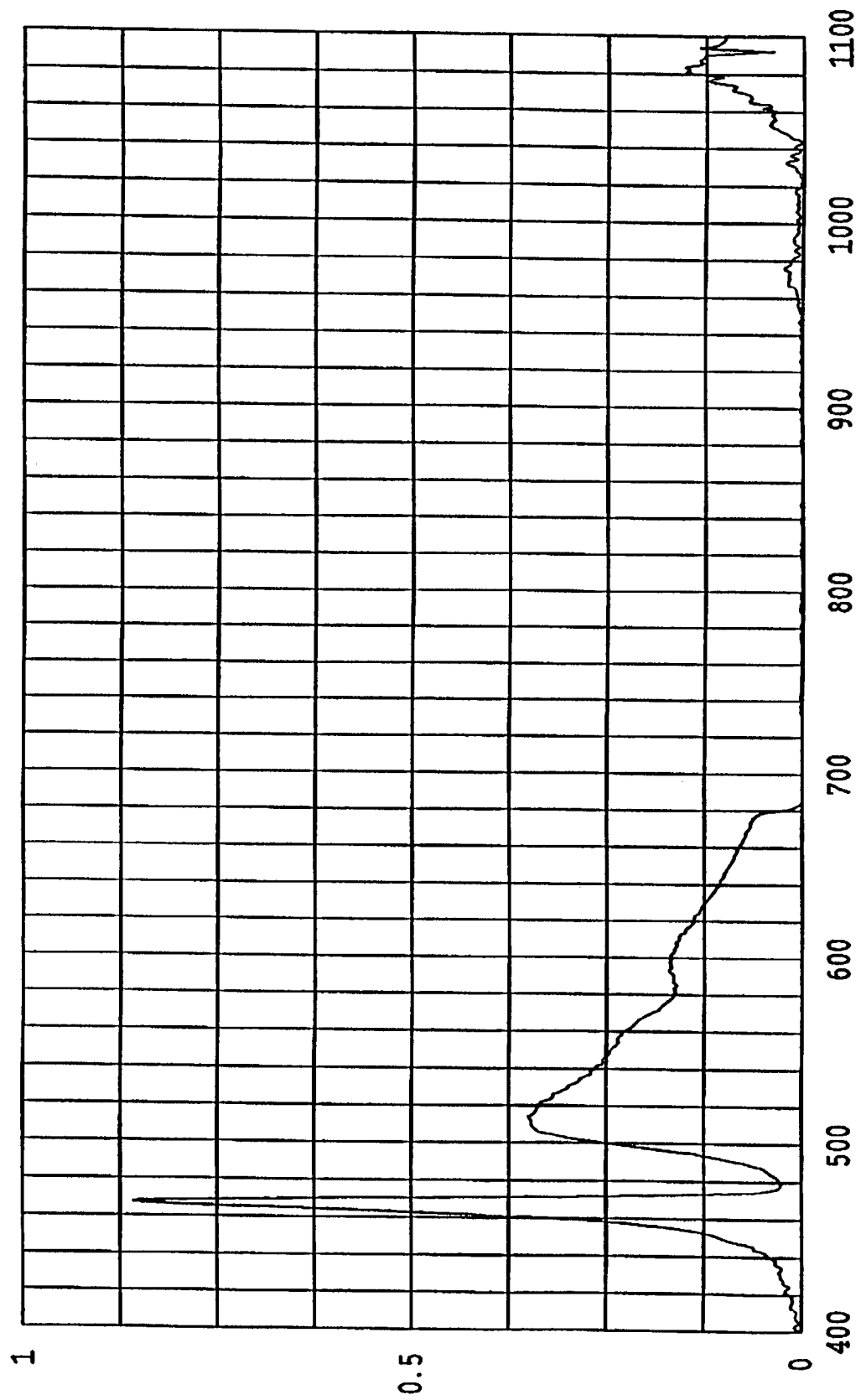
FIG. 22 shows the spectral intensity distribution, with the scale of the Y-axis being arbitrary, of light received by the image sensing chip 67 when the bandpass filter in FIG. 21 is used for the imaging unit in FIG. 7.

FIG. 21 shows an example of an optical filter having an excitation light removal performance that is insufficient. In FIG. 21, the solid line represents the% transmittance, to which the left-side scale applies, of the optical filter for a light beam having an angle of incidence of 0° (as measured to the surface normal). The dotted line represents the optical density, as defined above. The optical filter in FIG. 21 is a bandpass filter having a transmittance bandpass range of 500 nm to 600 nm (although not shown, the transmittance bandpass range extends to 680 nm), and blocks excitation light near 470 nm with an optical density of 4 (i.e., OD4) as shown by the dotted line. Also, just as in FIGS. 5(a)-5(e), the transmittance region of the bandpass filter for a light beam having an angle of incidence of 25° to the incidence surface shifts to the shorter wavelengths as compared to a light beam that has an angle of incidence near 0°. Thus, the light blocking property at 470 nm for a light beam having an angle of incidence of 25° becomes smaller than OD4. The spectral intensity distribution of light received by the image sensing chip 67 when the bandpass filter in FIG. 21 is used in the imaging unit in FIG. 7 is shown in FIG. 22. According to FIG. 22, fluorescence having an intensity peak near 510 nm appears in a range of 500 nm to 680 nm. On the other hand, excitation light having about twice the intensity of the fluorescent intensity peak appears near 470 nm. Thus, FIG. 22 shows a state where excitation light has leaked through the bandpass filter and has been detected by the image sensing chip 67.

Figure 23A:
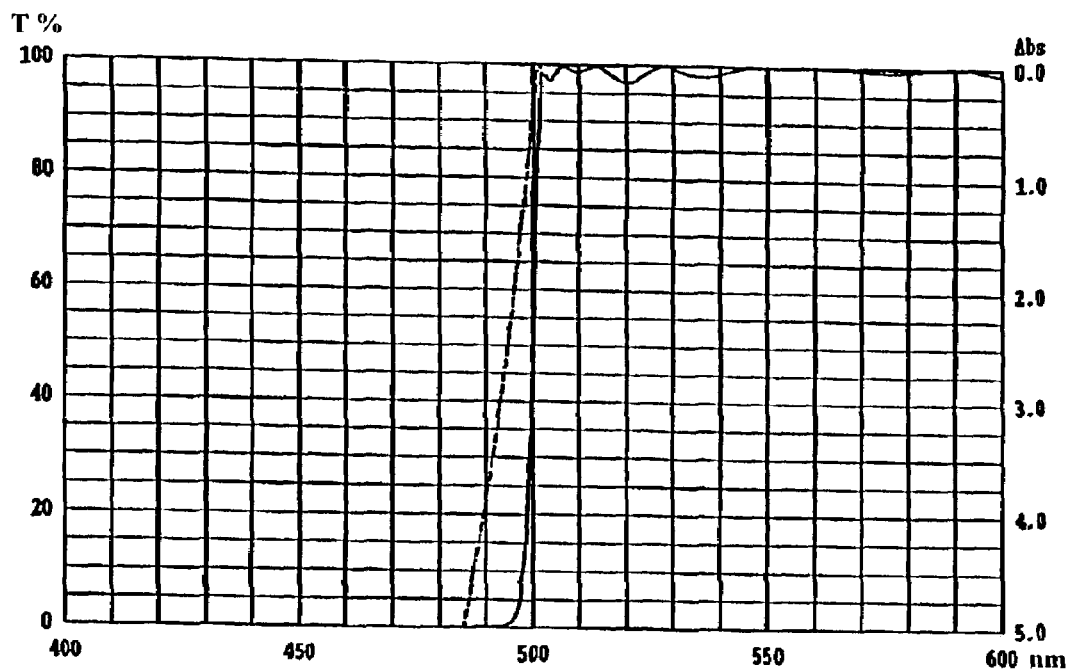
FIGS. 23($a$) and 23($b$) show optical properties of a bandpass filter having an excitation light blocking performance that is greater than the bandpass filter shown in FIG. 21, with FIG. 23($a$) showing by a solid line the spectral transmission (left-side scale) of the bandpass filter and showing by a dotted line the optical density (right-side scale) for a light beam incident at an angle of 0° to the surface normal, and with FIG. 23($b$) illustrating the same properties as shown in FIG. 23($a$) but being for a light beam incident at an angle of 25° to the surface normal.
Figure 23B:
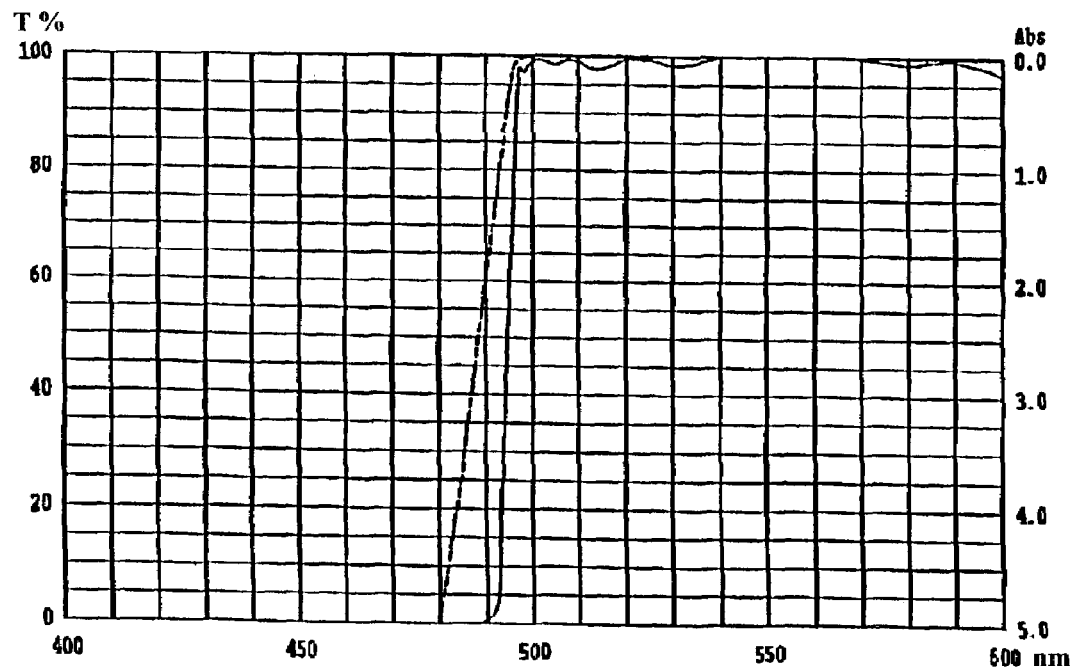

An example of an improved bandpass filter is shown in FIGS. 23(a) and 23(b). In FIG. 23(a), the solid line represents the transmittance of the bandpass filter for a light beam having an angle of incidence onto the incidence surface of 0° (as measured to the surface normal). The dotted line represents the light blocking property of the bandpass filter for the same light beam. The bandpass filter in FIG. 23(a) is a bandpass filter having a transmittance bandpass range of 500 nm to 680 nm, just as was the case for the bandpass filter discussed previously with regard to FIG. 21. However, the bandpass filter in FIG. 23(a) has an improved capacity to block excitation light near 470 nm that is incident at 0°, with the light blocking capacity being much larger than OD4. Indeed, the light blocking property for light near 490 nm that is incident at 0° is OD4.

Figure 24:
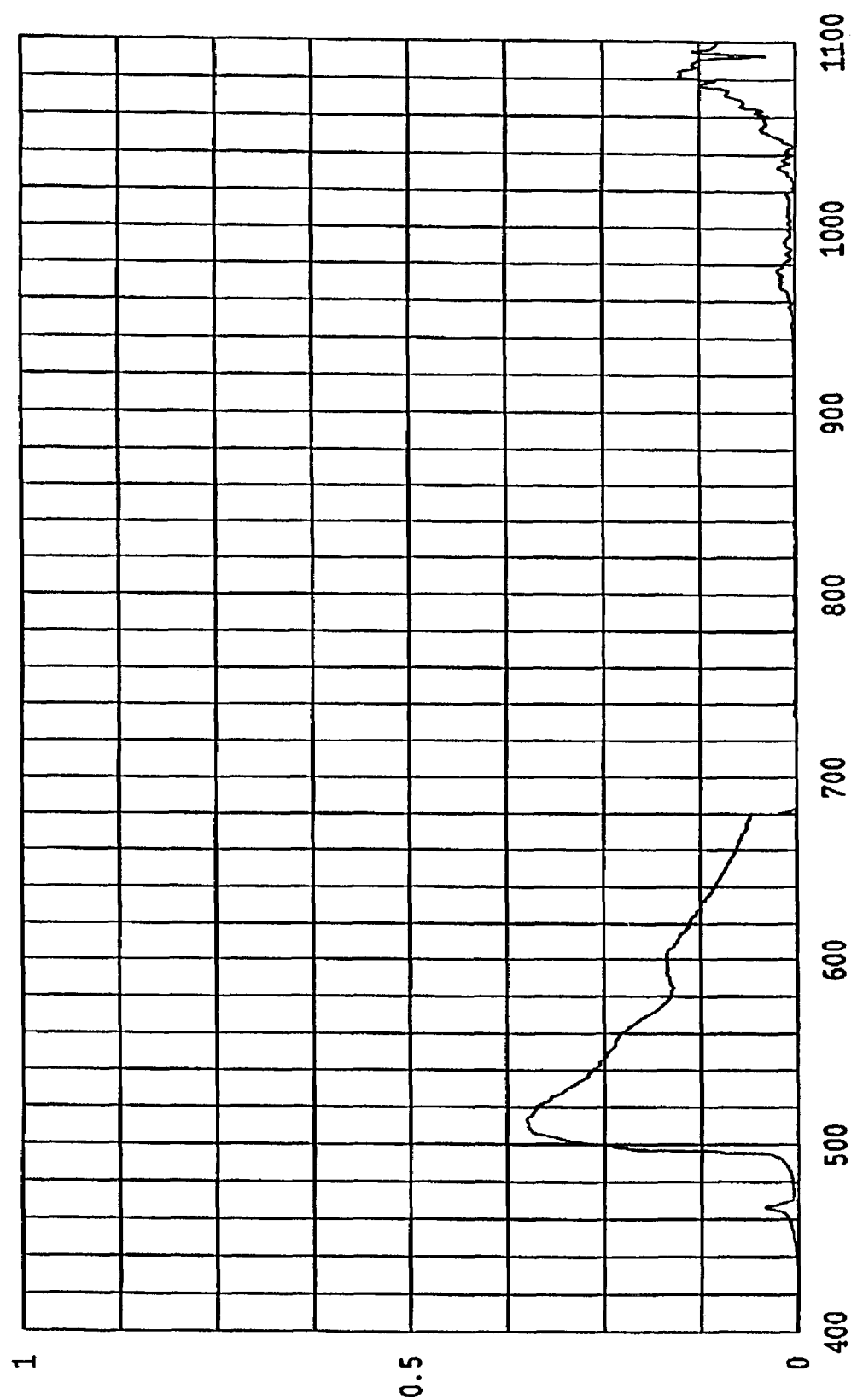
FIG. 24 shows the spectral intensity distribution of light received by the image sensing chip 67 when the bandpass filter in FIG. 23($a$) is used for the imaging unit in FIG. 7.

FIG. 23(b) illustrates the optical performance for the same filter as in FIG. 23(a), but with the incident angle of the light onto the filter being 25°. Once again, the solid line represents the transmittance according to the scale on the left side of the figure, and the dotted line represents the optical density, according to the scale on the right side of the figure. In spite of the fact that the spectral transmission shifts to shorter wavelengths as the angles of incidence become larger, the light blocking property at 470 nm remains significantly larger than OD4. This is achieved by increasing the number of interference film layers on the surface of the filter substrate as compared to the number of interference film layers on the surface of the filter substrate of the bandpass filter in FIG. 21. The spectral intensity distribution of light received by the image sensing chip 67 when the improved bandpass filter (i.e., one having a larger number of interference layers with an optical performance as illustrated in FIG. 23(b)) is used in the imaging unit in FIG. 7 is shown in FIG. 24. According to FIG. 24, although fluorescence having an intensity peak near 510 nm appears in a range of 500 nm to 680 nm, almost all the excitation light near 470 nm is blocked.

From the above, it can be seen that, when intensity peaks of excitation light and fluorescence are near one another on the X-axis (i.e., in terms of wavelength) and their intensity difference is very large, it is desirable that an optical filter having a strong excitation light blocking property be installed in the imaging unit. More particularly, the light blocking property of the optical filter should be OD4 or higher at a wavelength $\lambda_2$ which is shifted away from the peak transmittance by $\Delta\lambda$ equals 20 nm from a wavelength $\lambda_1$, where $\lambda_1$ is a wavelength where the transmittance becomes 50% for light having an angle of incidence η equal to 0°. And, the light blocking property of the optical filter should be OD4 or higher at the wavelength λ2 to light having an angle of incidence η of 25°. By using an optical filter which satisfies the above requirements, there is no optical "noise" overlap with fluorescent images which degrades the contrast, and thus clear fluorescent images can be obtained. Also, when the desired excitation light blocking property is realized with multiple filters, and these filters are placed at several places in the imaging unit, if the overall light blocking property of the multiple optical filters in the excitation light wavelength range is OD4 or higher, the same effect can be obtained.

Also, when performing laser burning of a lesion while observing the ordinary color image, a strict blocking property similar to the above is required for an optical filter which is to block the laser wavelength light from reaching the image sensor. Commonly, a YAG laser or a semiconductor laser is chosen as a laser type for medical treatment when infrared wavelengths are required, and the intensities of the beams from these lasers is more than 100 times that of red, green, and blue light necessary for forming ordinary color images. Because the image sensing chip has a sensitivity to these infrared laser wavelengths, when the laser wavelength blocking performance of the optical filter is insufficient and the lesion is irradiated with laser light, the observation image will become saturated and it will be difficult to observe anything. Laser treatment of the lesion cannot be performed under such conditions.

Figure 25A:
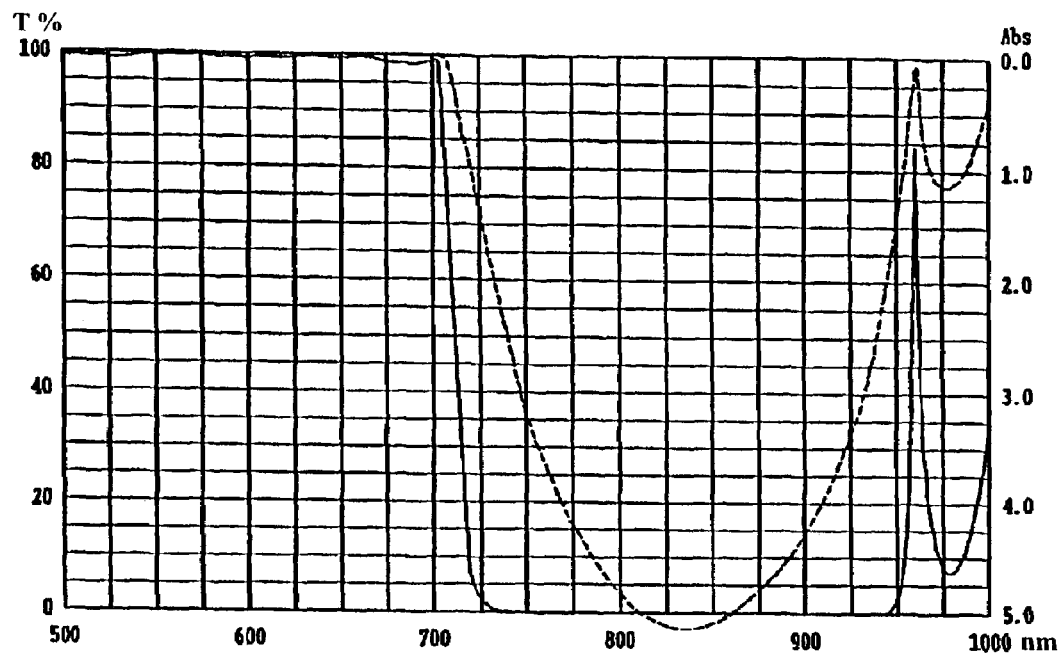
FIGS. 25($a$) and 25($b$) show optical properties of an optical filter which can securely block near-infrared light when using a semiconductor laser which emits near-infrared light in the wavelength range of 775 nm to 876 nm, with FIG. 25($a$) illustrating the situation for a light beam incident at an angle of 0° to the surface normal, and with FIG. 25($b$) illustrating the situation for the incident beam making an angle of 25° to the surface normal, with the solid and dashed lines and left-side versus right-side scales being the same as in FIGS. 23($a$) and 23($b$)
Figure 25B:
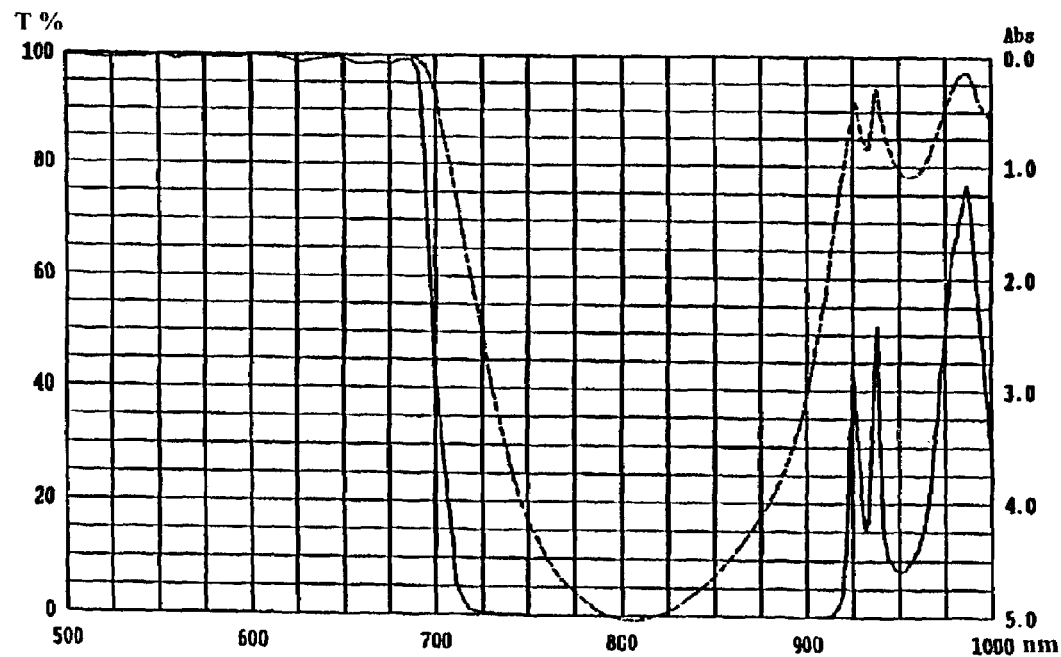

For example, when using a semiconductor laser which emits near-infrared light in a wavelength range of 775 nm to 875 nm, as optical filters which can securely block the near-infrared light, there are those having the properties shown in FIGS. 25(a) and 25(b). In FIG. 25(a), the solid line represents the transmittance of the optical filter for a light beam having an angle of incidence of 0° to the surface normal, and the dotted line represents the light blocking property of the band-pass filter for the same light beam. Once again the transmittance scale in % is at the left side of the figure and the light blocking scale, in terms of optical density, is at the right side of the figure.

The optical filter in FIG. 25(a) transmits light with wavelengths less than 715 nm and blocks wavelengths ranging from 715 nm to 960 nm and is manufactured so that, when the near-infrared light range to be blocked (namely the range of 775 nm to 875 nm) is expanded by 50 nm, the blocking properties becomes OD3 or higher at the boundary wavelengths (namely 750 nm and 900 nm), and the light blocking properties in the wavelength range of 775 nm to 875 nm is OD4 or higher.

FIG. 25(b) shows the optical properties for the same filter as that of FIG. 25(a), but rather than the light being incident at 0° to the surface normal, the angle of incidence is 25° to the surface normal of the filter. Once again, the solid line is the transmittance in % as measured on the left side scale and the dotted line is the optical density as measured on the right side scale. In spite of the fact that the transmission range shifts to the shorter wavelengths as the incidence angle becomes larger, the light blocking properties in the wavelength range of 775 nm to 875 nm are still significantly larger than OD4. Thus, the semiconductor laser light can be sufficiently blocked. Because of this, even when a lesion is irradiated with laser light, the observed image does not become saturated, and laser treatment can be performed safely.

If the optical properties of an optical filter which enables successful performance are to be generalized, the requirements become: an optical filter having the function of blocking a wavelength range of 100 nm or wider should have a light blocking property of OD3 or higher at the boundary wavelengths λ3 and λ4 when the wavelength range to be blocked is expanded by 50 nm. If the ratio Q'/Q, where Q is the intensity of light transmitted by an optical filter and Q' is the intensity of light to be blocked by an optical filter is about 100, it is desirable that the optical filter satisfy the requirements mentioned in the previous sentence. As above, a scope constructed with a single imaging unit enables the tip to be made thin for insertion into a relatively narrow space, such as the bronchial tubes. Both ordinary color image observations and fluorescent observations can be performed by appropriately selecting the transmittance properties of the optical filters, as will be described in greater detail later.

Another example is a scope where two observation windows are installed at the tip and a separate imaging unit is used at each window. The two imaging units have different optical properties such as field of view, image magnification, and depth of field so as to correspond to their respective observation objectives. Furthermore, the number of pixels, the size of the imaging area, and the reception sensitivity are different. For example, it is conceivable that the two imaging units have the following characteristics. One imaging unit can perform ordinary color image observations and infrared image observations. The field of view is about 120° to 160°, with a depth of field of about 10 mm to 100 mm. The other imaging unit can perform ordinary color image observations and fluorescent image observations, the image magnification can change so that the field of view ranges from 60° to 120°, and the depth of field is from about 2 mm to 30 mm. Also, in order to provide images with sufficient brightness such as object images when visible light is divided into multiple narrow-band wavelength ranges and emitted sequentially and object images are desired using fluorescent observations, an image sensing chip having a high photosensitivity is used. Thus by configuring a single scope by combining imaging units of different characteristics, multiple special light observations disclosed in the present invention can be efficiently performed using a single scope. Because of this, the troublesome work of switching the endoscope apparatus every time a special light observation is changed can be avoided.

Yet another example is a scope where there are two observation windows installed at the tip. An optical unit which is equipped with an objective lens and a filter is installed in each of the two observation windows, and a single image sensing chip is utilized. These optical units have different optical performances such as field of view, image magnification, and depth of field so as to correspond to specific observation objectives. Also, the spectral transmittance properties of the filters differ, and the image sensing chip receives images on its detecting surface from both optical units. In this case, compared with the case where two image sensing chips are used, the scope tip can be made thinner. Also, because processing of the image signals can be performed relatively easily if there is only one image sensing chip, displaying two images side-by-side on one monitor screen is also easy. Needless to say, with all three kinds of scopes, the viewing directions of the imaging units can be changed as needed. The endoscope apparatus of the present invention can perform observation and removal of living body lesions through the series of Procedures (1)-(4), discussed previously.

Figure 26:
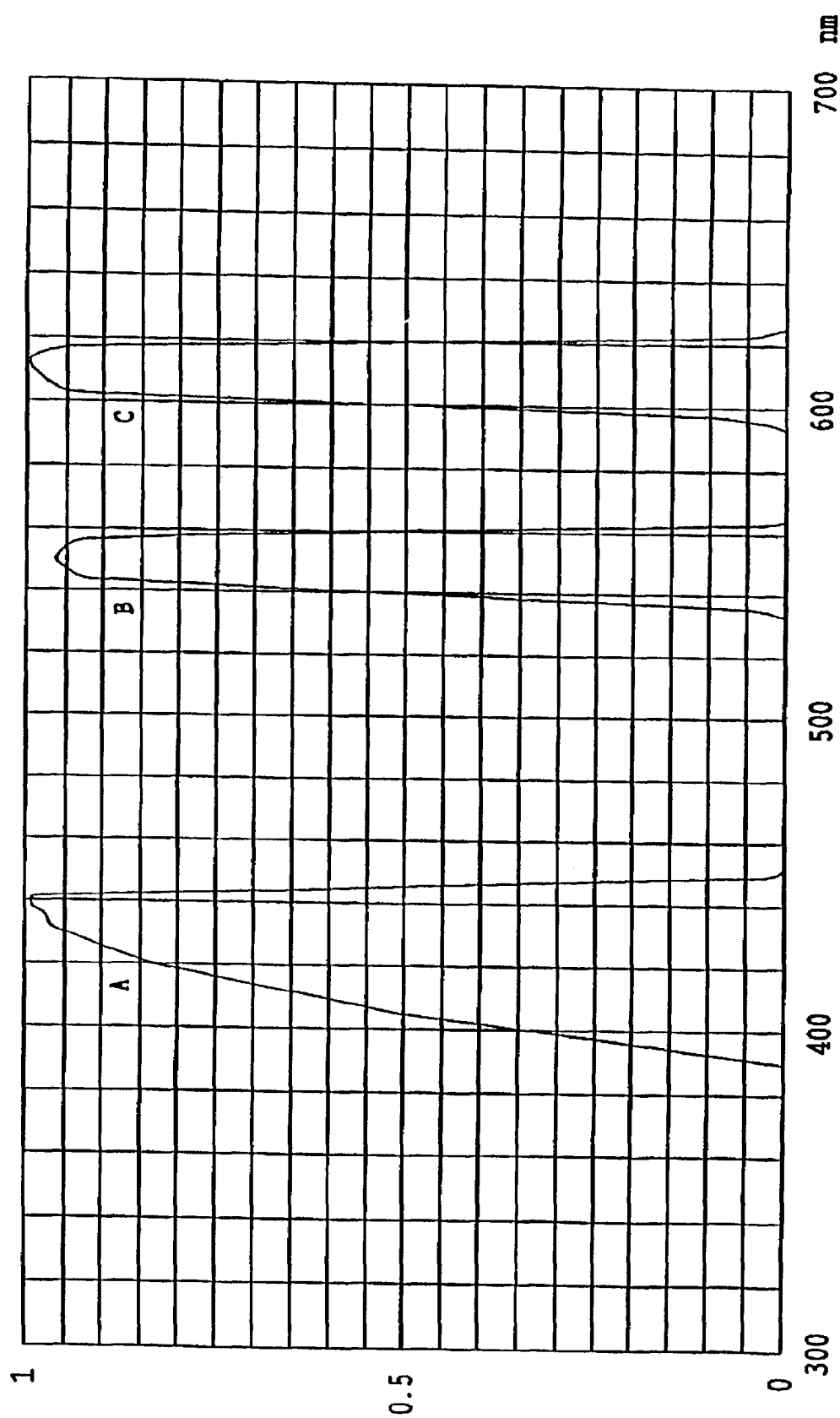
FIG. 26 shows the spectral intensity distribution, with the scale of the Y-axis being arbitrary, of the illumination light used when performing observations according to Procedure 1 in a series of observation and removal procedures of an in vivo lesion shown in the first embodiment.
Figure 27:
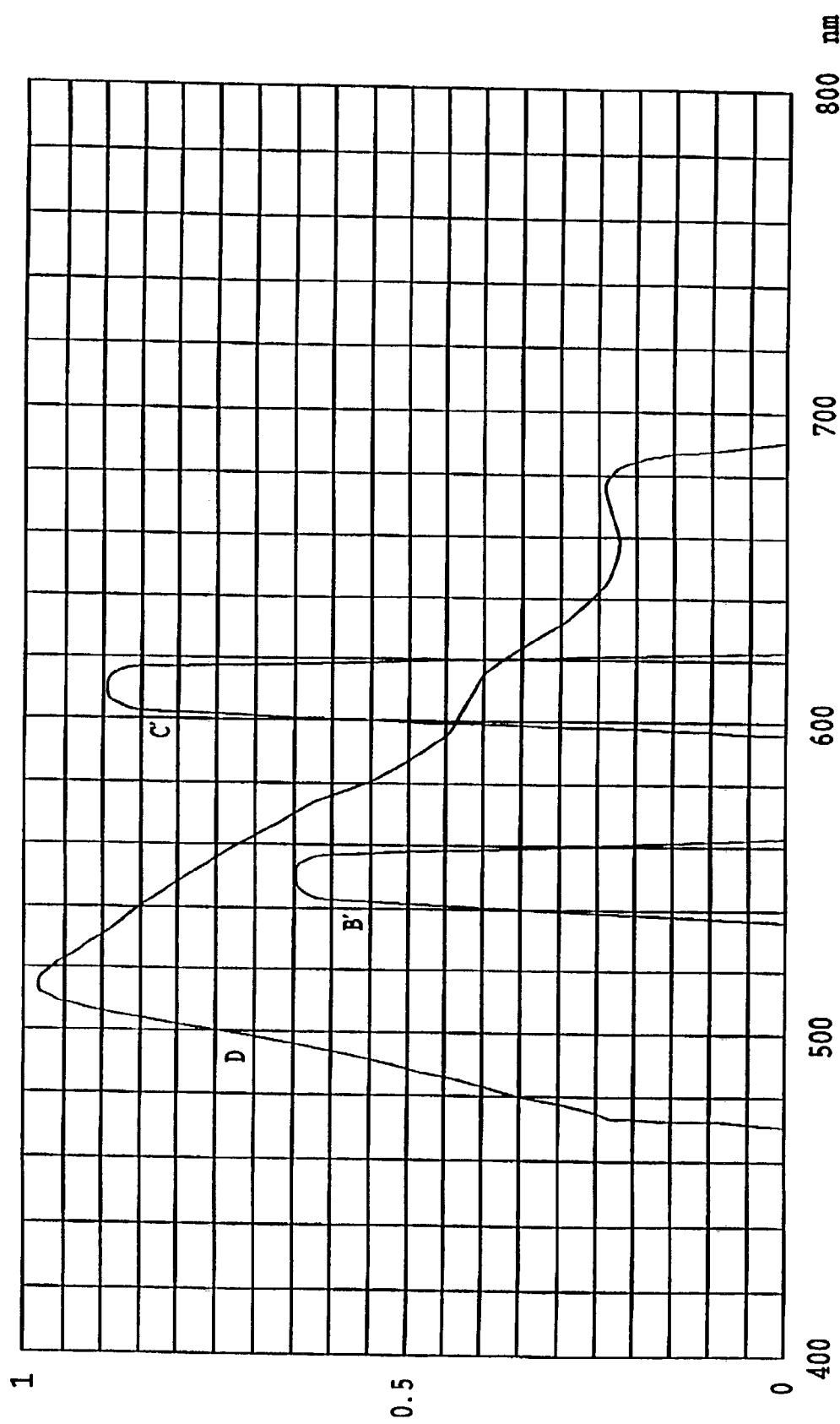
FIG. 27 shows the spectral intensity distribution, with the scale of the Y-axis being arbitrary, of fluorescence and reflected light at the image surface obtained from normal in vivo tissue when it is irradiated with light in the wavelength range shown in FIG. 26.

In Procedure 1, the light source unit illuminates repeatedly and sequentially using light in 10 the wavelength ranges shown in FIG. 26 using the illumination unit of the scope. The spectral intensity curve A in FIG. 26 is an excitation light for exciting fluorescence of living body tissues, utilizing light shorter than 445 nm in wavelength. In the spectral intensity curve A, the reason the intensity decreases as the wavelength becomes shorter is that the light guide in the illumination unit absorbs light of the shorter wavelengths. The spectral intensity curve B and the spectral intensity curve C are illumination light of different wavelength ranges for retrieving information other than fluorescence from living body tissues, utilizing light in very narrow wavelength ranges from 540 nm to 560 nm and from 600 nm to 620 nm, respectively. In order to compare the spectral intensity properties of three illumination beams in a single figure, the spectral intensity curves B and C in FIG. 26 are displayed with the actual intensity multiplied by a factor of 500 to 1000.The imaging unit is equipped with a filter which blocks the excitation light, and if light of the different wavelength ranges shown in FIG. 26 is illuminated onto normal living body tissue, images in fluorescent light D and images in reflected light of spectral content B' and C' shown in FIG. 27 are obtained. In FIG. 27, the fluorescent light D has a spectral intensity distribution with a peak near 510 nm in the wavelength range of 470 nm to 690 nm, and the reflected light of spectral content B' and C' have spectral intensity distributions in the wavelength ranges of 540 nm to 560 nm and 600 nm to 620 nm, respectively.

When the spectral intensity distribution of fluorescent light emitted from normal living body tissue and the spectral intensity distribution of fluorescent light emitted by lesions such as cancer are compared, it is known that the intensity of fluorescent light emitted by lesions is less. By utilizing the difference in fluorescent intensity as mentioned above, image processing is performed by a video processor so that lesions are displayed separately from normal living body tissues. However, there are cases where processing images based merely on information obtained from fluorescence emitted by normal living body tissue versus lesions cannot clearly separate the boundary between the normal living body tissue and a lesion. In this embodiment, image processing is performed by adding information obtained in reflected light of spectral content B' and C' shown in FIG. 27 (i.e., the reflected light from living body tissue in the wavelength ranges of 540 nm to 560 nm and 600 nm to 620 nm, respectively). As the reflected light from living body tissues, light centered at the wavelength of 550 nm, which is one of the wavelengths absorbed by hemoglobin in blood, and light centered at the wavelength of 610 nm, which does not belong to the absorption wavelengths, can be selected. Thus, the distribution of capillary blood vessels in a normal living body tissue versus a lesion of the living body tissue is detected. By adding this as new information for separating the boundary between the normal tissue and a lesion of living body tissue, it becomes possible to separate clearly the boundary between the normal tissue and a lesion of the living body tissue. Thus, the resolution of fluorescent images is improved by increasing the amount of information about the boundary between the normal tissue and the lesion of the living body tissue.

Figure 28:
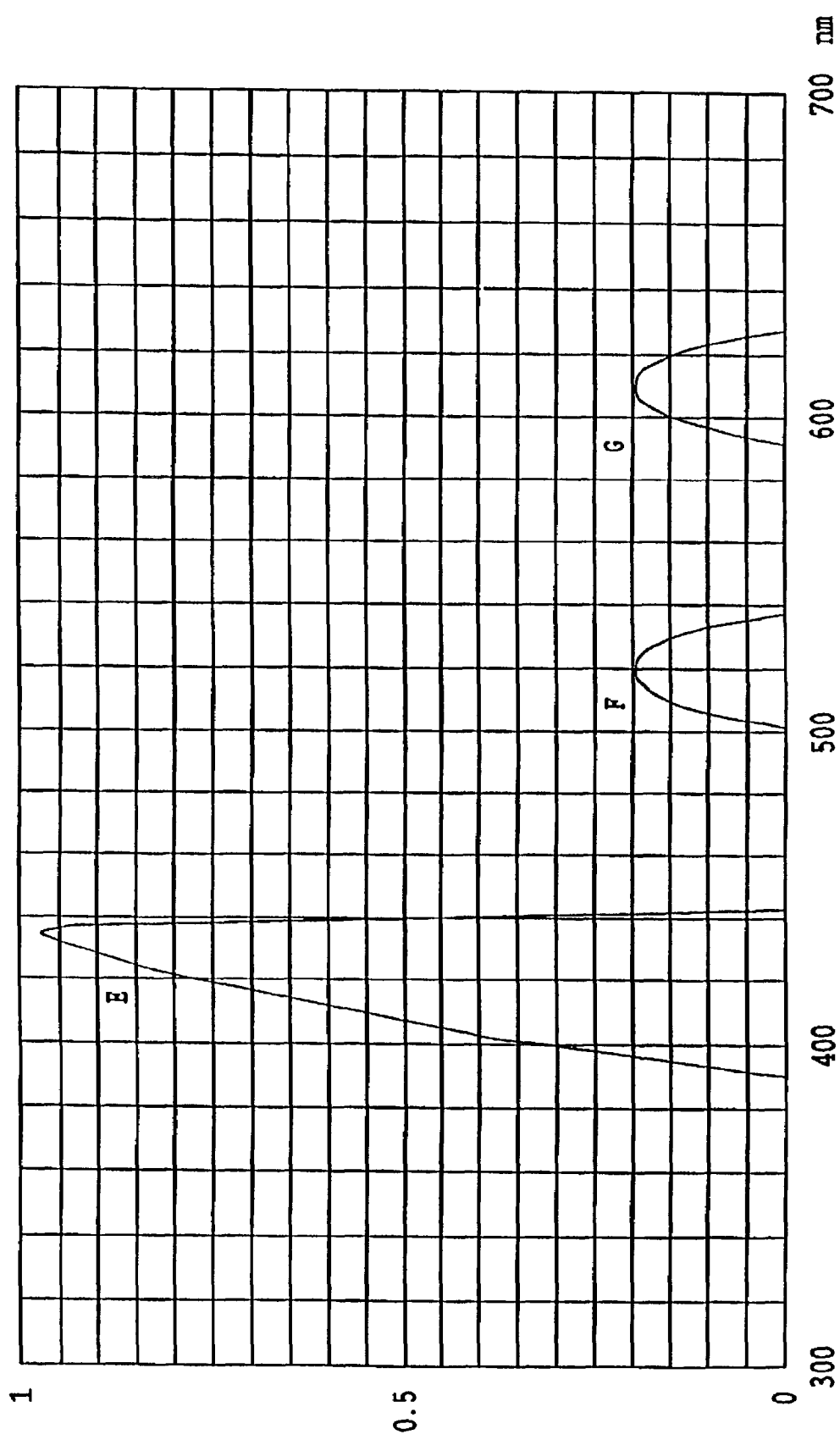
FIG. 28 shows the spectral intensity distributions, with the scale of the Y-axis being arbitrary, of illumination light of different wavelength ranges used when performing an observation according to Procedure 2 in a series of observation and removal procedures of an in vivo lesion using the endoscope apparatus of first embodiment.

In Procedure 2,the light source unit illuminates the object repeatedly and sequentially with light in the very narrow wavelength ranges shown in FIG. 28 through the illumination unit of the scope. Living body soft tissue commonly has a layered-structure that varies in the depth direction from the surface. The layer nearest the surface is the mucosal layer where many capillary blood vessels are distributed. Deeper in the mucosal layer, blood vessels thicker than capillary blood vessels and lymphatics are distributed. As discussed briefly above, the penetration depth of light into living body tissue depends upon the wavelength of the light. The spectral intensity curve E shown in FIG. 28 is light in the blue region having wavelengths shorter than 440 nm, and is useful for obtaining information on the mucosal layer. A reason why the intensity decreases rapidly as the wavelength becomes shorter than that of the peak intensity for the E curve is that the light guide of the illumination unit absorbs light at these shorter wavelengths.

Because the blue region light has short wavelengths and thus is reflected by the mucosal layer, this reflected light contains information on the mucosal layer. For example, it is known that normal tissue and lesions such as cancer in the mucosal layer have different shapes of capillary blood vessels and there is a difference in cell array density. When the mucosal layer images are optically expanded and the capillary blood vessels and cells distributed therein are observed, a determination can be made as to whether a region is cancerous or not. Also, the range of cancer can be correctly specified by observing the boundary between the normal tissue and the cancerous tissue.

The spectral intensity curve F shown in FIG. 28 is light in the wavelength range of 505 nm to 535 nm, which is in the green region of the spectrum. Also, the spectral intensity curve G is an illumination light in the wavelength range of 595 nm to 625 nm which is in the red region of the spectrum. In the case of using illumination light in the green region and the red region, both of which have longer wavelengths than light in the blue region, because light is reflected after reaching deeper than the mucosal layer, tissue information in the middle layer or even deeper layers of a living body tissue can be obtained. This information is processed in the video processor, and an image containing the desired tissue information is displayed.

When desiring information that is to be obtained from the mucosal layer, the illumination intensity of the blue region light is made to be higher than the illumination intensity of other wavelength regions. In this way, the amount of information obtained from the mucosal layer can be increased, and the degree of freedom in processing information by the video processor can be increased. As shown in FIG. 28, the illumination intensity of the blue region light is set about five times higher than that of the green region light and the red region light. In other words, the intensity of the green region light and the intensity of the red region light is about one-fifth the intensity of the blue region light. Therefore, images are obtained in which the boundaries between lesions and normal tissue in the mucosal layer can be clearly distinguished.

Figure 29:
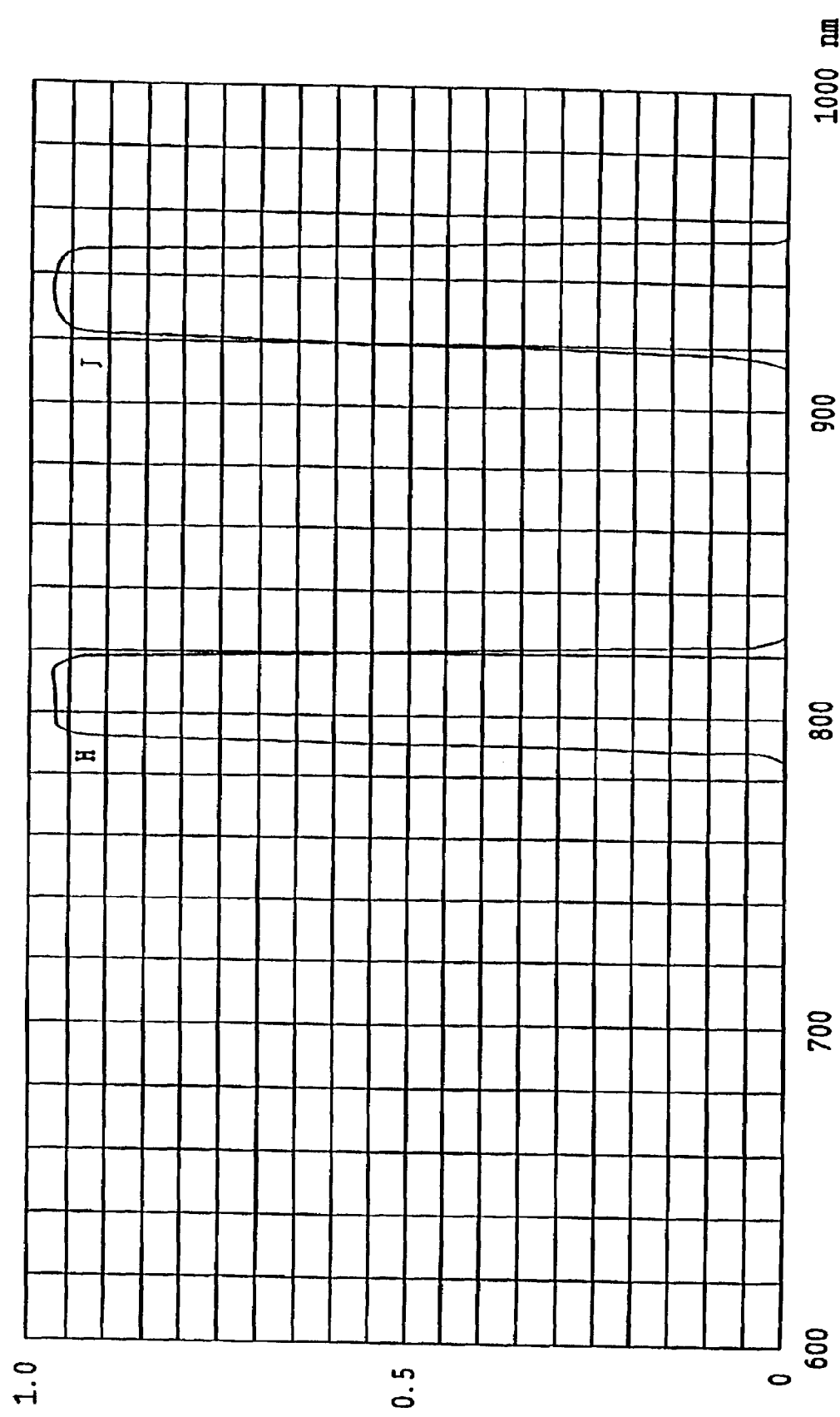
FIG. 29 shows the spectral intensity distribution, with the scale of the Y-axis being arbitrary, of the illumination light used when performing an observation according to Procedure 3 in a series of observation and removal procedures of an in vivo lesion using the endoscope apparatus of the first embodiment.

In Procedure 3, the light source unit irradiates the object repeatedly and sequentially with radiation in the wavelength ranges shown in FIG. 29 through the illumination unit of the scope. The spectral intensity curve H shown in FIG. 29 is radiation in the wavelength range of 790 nm to 820 nm, which is in the near-infrared region. The spectral intensity curve J is radiation in the wavelength range of 920 nm to 950 nm, which also is in the near-infrared region. Thus, as shown in FIG. 29, each of the spectral intensity curves H and J has a separate spectral transmission peak within a different wavelength range of the infrared region.

Observations using near-infrared region radiation are effective for examining the state of blood vessels in the lower layer of the mucosa. In this method by injecting indocyaninegreen (ICG) having an absorption peak near a wavelength of 805 nm into a vein as a contrast medium, contrast is obtained for viewing the blood vessels in the lower layer of the mucosa, and the state of these blood vessels can be clearly observed. By forming images using near-infrared light having a wavelength near 805 nm (i.e., the peak absorbance wavelength of ICG) and a wavelength near 930 nm (where the absorbance of ICG is relatively low), the distribution of ICG inside the blood vessels can be displayed as being pseudo-colorized for ease of observation. If cancer has infiltrated to the lower layer of the mucosa, there occurs a difference in blood flow in the blood vessels in the cancerous regions versus the non-cancerous regions, and thus the presence/absence of cancer in the lower layer of the mucosa can be examined. Thus, whether or not cancer has infiltrated beyond the mucosa can be determined by examining the state of the lower layer of the mucosa. If the cancerous tissue is limited to the mucosal layer, it may be possible to remove the cancerous tissue using an endoscope.

Figure 30:
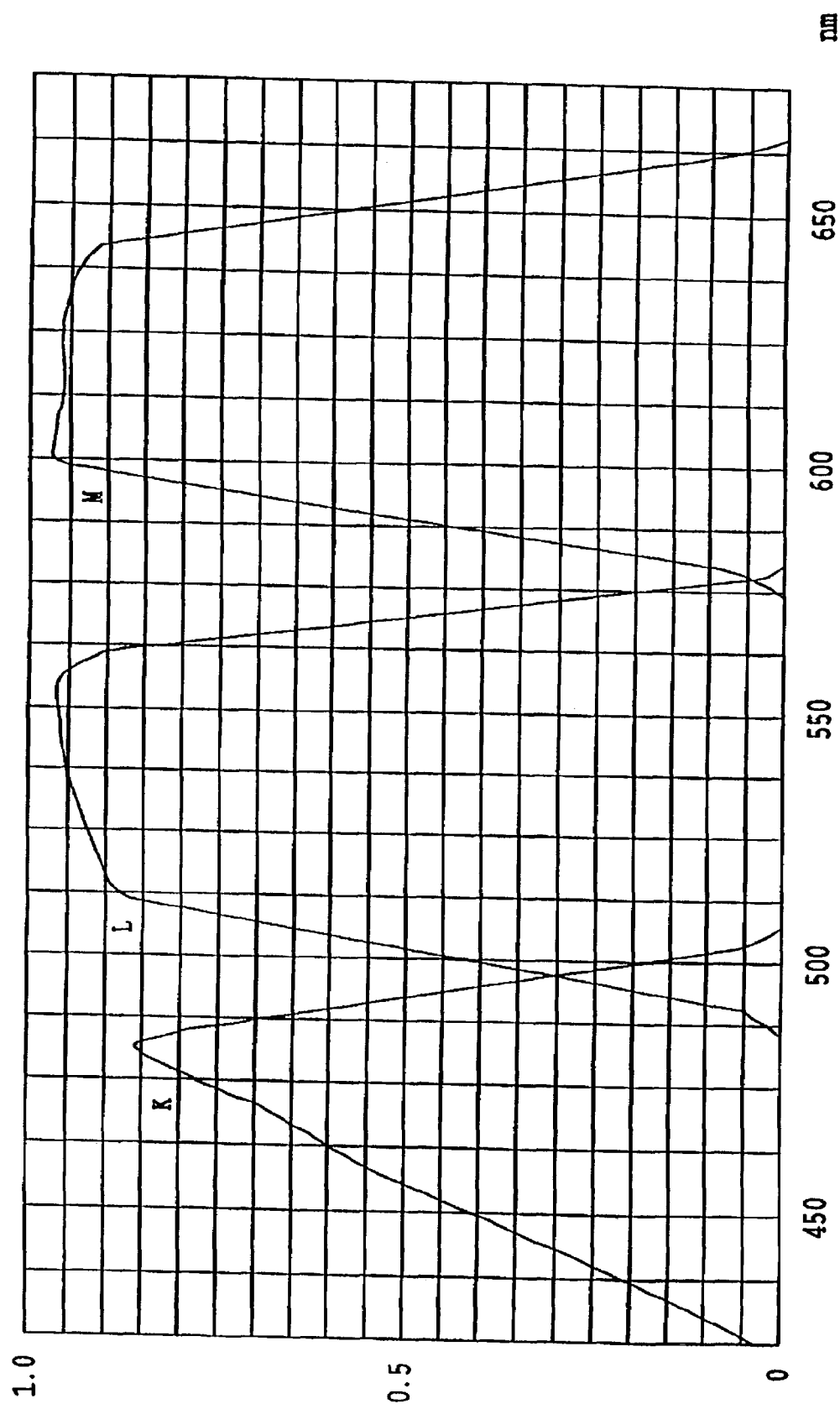
FIG. 30 shows the spectral intensity distribution, with the scale of the Y-axis being arbitrary, of the illumination light used when performing an observation according to Procedure 4 in a series of observation and removal procedures of an in vivo lesion using the endoscope apparatus of the first embodiment.

In Procedure 4, the light source unit illuminates the object repeatedly and sequentially using light in the wavelength ranges shown in FIG. 30 through the illumination unit of the scope. The spectral intensity distribution K shown in FIG. 30 is illumination light shorter than 495 nm. In the spectral intensity distribution K, a reason why the intensity decreases from the peak intensity as the wavelength becomes shorter is that the light guide which forms the illumination unit absorbs light at shorter wavelengths. The spectral intensity distribution L is illumination light in the wavelength range of 500 nm to 575 nm. Also, the spectral intensity distribution M is illumination light in the wavelength range of 585 nm to 655 nm. Because the spectral intensity distributions K, L, and M are broadband illumination sources within the visible spectrum which correspond generally to the regions of blue, green, and red light, respectively, bright color images having good color reproducibility can be obtained using these illumination sources.

In order to safely treat a lesion such as cancer, it is necessary that the lesion and the surrounding tissue be imaged with good color reproducibility. In the endoscopic mucosal resection (EMR), a treatment tool is inserted near the lesion through an insertion channel installed in the endoscope, and the treatment tool is utilized to remove the mucosal lesion while observing images of the lesion and its surrounding tissue. Also, when burning a mucosal lesion using laser radiation, a laser probe is inserted near the lesion through the insertion channel of the endoscope, and laser irradiation is performed thoroughly over the lesion while observing images of the lesion and its surrounding tissue.

By the above procedures, it is possible to eliminate the time and labor needed to excise a sample for pathological examination, which is usually done immediately after discovery of a lesion such as cancer. Therefore, by using the endoscope apparatus and the diagnosing method of the present invention, within a much shorter time from the discovery of a lesion such as cancer, the state of the lesion can be determined. Furthermore, if the situation allows for endoscopic treatment, excision of the lesion can be performed at once.

In the endoscope apparatus of the invention, in order to perform a series of observations, optical filters having the spectral transmittance as shown in FIGS. 31(a)-31(e) are provided in the light source unit. FIGS. 31(a)-31(e) show the spectral transmittance properties of optical filters 111, 112a, 112b, 113, and 114, respectively, that are concentrically arranged on the turret.

On the other hand, FIGS. 32(a)-32(f) show the spectral transmittance of optical filters 115-120, respectively, that are arranged on the rotary filter wheel of the light source unit. On the outer circle of the rotary filter wheel, the optical filters 115, 116, and 117 are concentrically arranged. Also, on the inner circle of the rotary filter wheel, the optical filters 118, 119, and 120 are concentrically arranged. In this embodiment, at least one optical filter of the turret (namely, filter 114 shown in FIG. 31(e)) and at least one optical filter of the rotary filter wheel (e.g., optical filter 116 or 117, shown in FIGS. 32(b) and 32(c), respectively) each transmit light in at least two wavelength ranges.

Figure 32A:
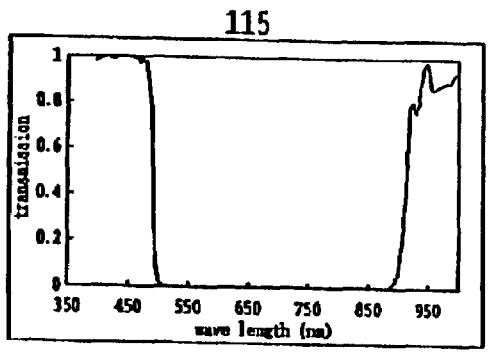
FIGS. 32($a$)-32(f) show the spectral transmittance of optical filters placed on a rotary filter wheel in the light source unit used in the first embodiment.
Figure 32B:
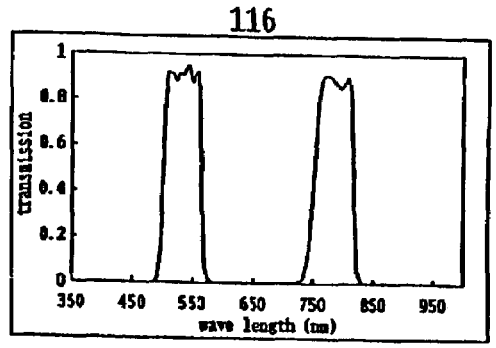
Figure 32C:
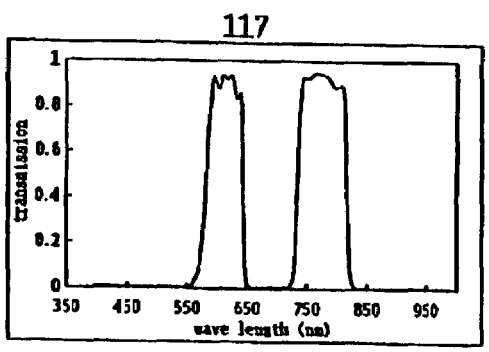
Figure 32D:
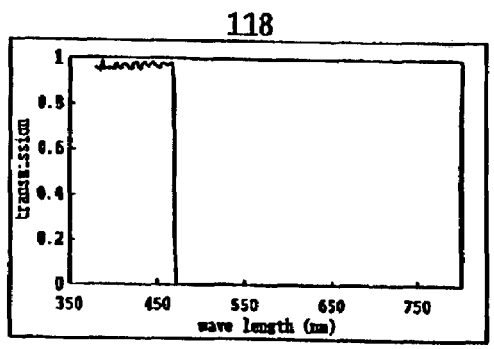
Figure 32E:
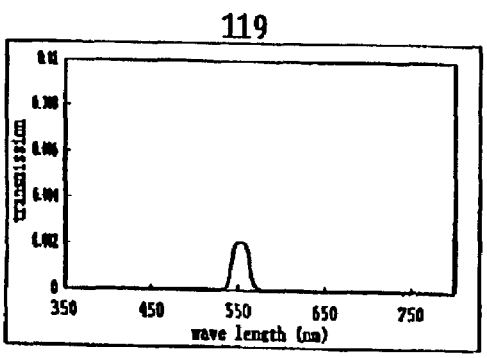
Figure 32F:
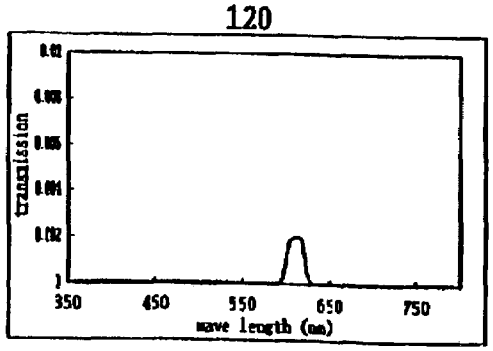
Figure 33A:
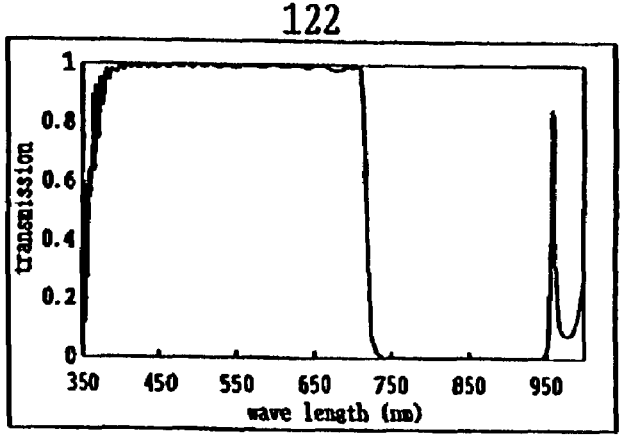
FIGS. 33($a$)-33($c$) show the spectral transmittance of optical filters placed in the imaging optical system of the scope used in the first embodiment.
Figure 33B:
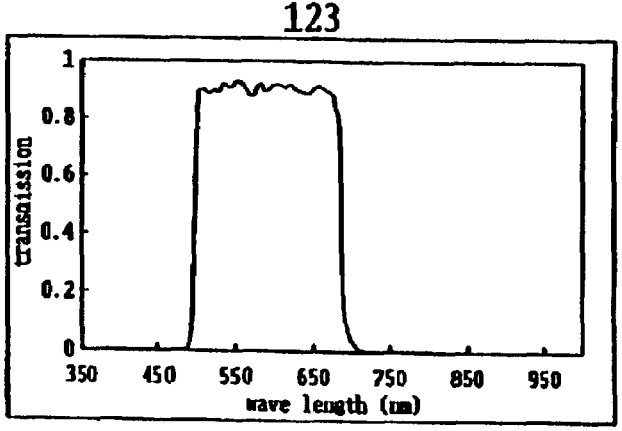
Figure 33C:
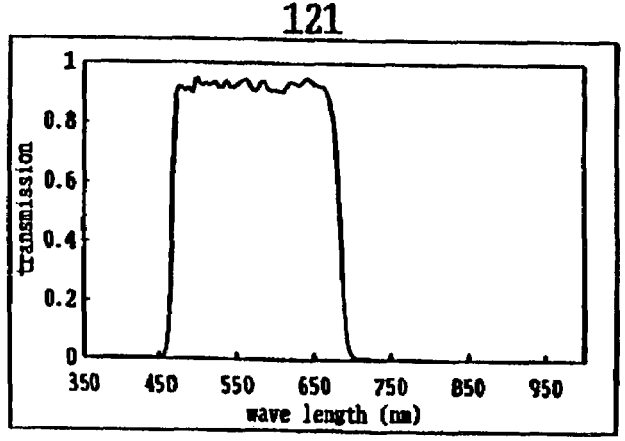

FIGS. 33(a)-33(c) show the spectral transmittance of optical filters 122, 123, and 121, respectively, that are arranged in the imaging optical system of the scope. Desired observation images can be obtained by selecting different combinations of the optical filters shown in FIGS. 31(a) to 33(c) depending on the kind of observation undertaken. Examples of different combinations of these optical filters will now be given according to the observation and treatment procedures.

In Procedure 1, the light source unit illuminates the object repeatedly and sequentially through the illumination unit of the scope with light having the spectral intensity curves A, B and C as shown in FIG. 26. At the same time, the turret of the light source is rotated so as to insert an optical filter into the light path. Each window of the turret can be filled with a filter having a desired spectral transmittance and optical density for wavelengths that are to be blocked, or two or more filters in series can be placed within a single window of the turret so as to obtain a desired spectral transmittance and optical density of the wavelengths that are to be blocked. Also, the rotary filter wheel of the light source unit is mounted so that it may be translated in a plane normal to the optical axis so as to insert the inner circle of the rotary filter wheel into the light path. Then, the rotary filter wheel is rotated at a constant rate so as to sequentially insert the optical filters 118, 119, and 120 having spectral transmittances as shown in FIGS. 32(d), 32(e) and 32(f) respectively, into the light path with a constant period.

As mentioned above, a single window of the turret, or for that matter of the rotary filter wheel, may contain optical filters in series. For example, an optical filter may be formed of a bandpass filter 112a, having a transmittance bandpass range of 390 nm to 695 nm, in series with a filter 112b which blocks wavelengths from 445 nm to 510 nm. Also, an optical filter can block or transmit wavelengths longer or shorter than a specified wavelength. For example, filter 118 has a transmittance bandpass range as shown in FIG. 32(d), i.e., it is transmissive to light of 470 nm or shorter, and blocks longer wavelengths. Thus, when the optical filters 112a and 112b are placed in series in the light path, excitation light having a wavelength range of 390 nm to 445 nm will be transmitted.

The optical filter 119 as shown in FIG. 32(e) consists of a combination of a bandpass filter having a transmittance bandpass range of 540 nm to 560 nm and a means to adjust the intensity of the transmitted light so that it is within a range of 1/500 to 1/1000 of the intensity of the light that is incident in the range of 540 nm to 560 nm. The optical filter 120 as shown in FIG. 32(f) consists of a combination of a bandpass filter having a transmittance bandpass range of 600 nm to 620 nm and a means to adjust the intensity of the transmitted light so that it is within a range of 1/500 to 1/1000 of the intensity of the light that is incident in the range of 600 nm to 620 nm. When the optical filters 119 and 120 are each inserted into the light path, an illumination light for retrieving information other than fluorescence from a living body tissue is allowed to exit the light source unit.

The optical filter 121 having a transmittance as shown in FIG. 33(c) is placed in the imaging optical system of the scope. The optical filter 121 is a bandpass filter having a transmittance bandpass range of 470 nm to 690 nm. Therefore, excitation light does not reach the image surface of the imaging optical system, but fluorescent light of spectral intensity distribution D and light of spectral intensity distributions B' and C', (shown in FIG. 27) do reach it.

Figure 31A:
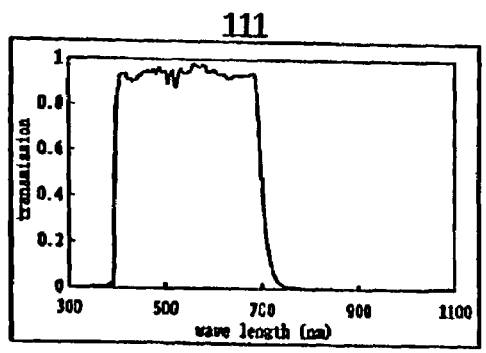
FIGS. 31($a$)-31($e$) show the spectral transmittance of optical filters placed on a turret in the light source unit used in the first embodiment.

When performing ordinary color image observations using the imaging optical system, the turret of the light source unit is rotated so as to insert the optical filter 111, having a spectral transmittance as shown in FIG. 31(a). Also, the rotary filter wheel of the light source unit is translated so as to insert the outer circle of filters of the rotary filter wheel into the light path. Then, the rotary filter wheel is rotated at a constant rate so as to insert the optical filters 115, 116, and 117 having spectral transmittance as shown in FIGS. 32(a), 32(b) and 32(c), respectively, repeatedly into the light path with a constant period. The optical filter 111 having a transmittance as shown in FIG. 31(a) is a bandpass filter which has a transmittance bandpass range of 390 nm to 695 nm, which is the same range of transmittance as the bandpass filter 112a shown in FIG. 31(b). Also, the optical filter 115 has a spectral transmittance as shown in FIG. 32(a) (i.e., a bandpass from 385 nm to 495 nm) and also it transmits light longer than about 920 nm. When the optical filter 115 is inserted into the light path, blue light of a wavelength range of 390 nm to 495 nm is allowed to exit the light source unit. Then, light reflected from the living body tissue having wavelengths from 470 nm to 495 nm is allowed to reach the image surface of the optical system.

The optical filter 116 has a spectral transmittance as shown in FIG. 32(b), i.e., it has a transmittance bandpass range of 500 nm to 575 nm as well as a transmittance bandpass range of 765 nm to 820 nm. When the optical filter 116 is inserted into the light path, green light of a wavelength range of 500 nm to 575 nm is allowed to exit the light source unit. Then, light reflected from the living body tissue of wavelengths from 500 nm to 575 nm is able to reach the image surface of the imaging optical system.

The optical filter 117 has a spectral transmittance as shown in FIG. 32(c), i.e., its transmittance ranges are 585 nm to 655 nm and 745 nm to 820 nm. When the optical filter 117 is inserted into the light path, red light of a wavelength range of 585 nm to 655 nm is allowed to exit the light source unit. Then, light of a wavelength range of 585 nm to 655 nm that is reflected by living body tissue reaches the image surface of the imaging optical system. The monochrome images of blue, green, and red are synthesized in the image processing circuit so as to obtain an ordinary color image. Thus, by combining optical filters, fluorescent image observations and ordinary color image observations can be performed using a single imaging optical system.

Figure 31B:
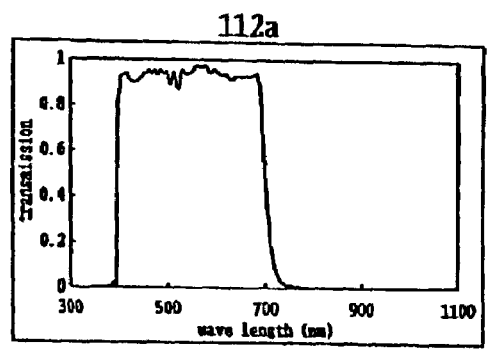
Figure 31C:
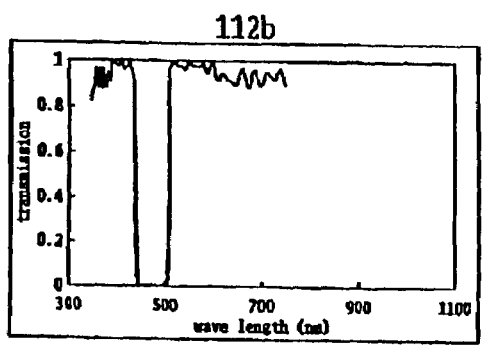

As an example of a possible modification, an optical filter 111 as shown in FIG. 31(a) can also be used in place of the optical filters 112a and 112b as shown in FIGS. 31(b) and 31(c), respectively, that are placed in series at a single position of the turret of the light source unit. In this case, an optical filter 123 is used which replaces the optical filter 121 which has a transmittance as shown in FIG. 33(c) in the imaging optical system of the scope. As shown in FIG. 33(b), the optical filter 123 has a transmittance bandpass range of 500 nm to 680 nm.

Excitation light in a wavelength range of 390 nm to 470 nm is allowed to exit the light source unit by combining the optical filter 111 having a transmittance bandpass range from 390 nm to 715 nm as shown in FIG. 31(a) and the optical filter 118 having a transmittance for wavelengths less than 470 nm as shown in FIG. 32(d) and placing these filters, in series, in a single position of the rotating filter wheel of the light source unit. Fluorescent light of a wavelength range of 500 nm to 680 nm that is emitted by living body tissue in response to being irradiated by the excitation light then reaches the image surface of the imaging optical system. In the same way, two kinds of illumination sources are allowed to exit the light source unit for retrieving information other than fluorescence from a living body tissue by placing the optical filter 119 and the optical filter 120 at different positions of the filter wheel so as to become rotating filters of the light source unit. Then, fluorescent light of a wavelength range of 540 nm to 560 nm and light of a wavelength range of 600 nm to 620 nm that is reflected by the living body tissue is allowed to reach the image surface of the imaging optical system. In this example, the imaging optical system can only perform fluorescent image observations. However, by expanding the wavelength range of the excitation light, the brightness of the excitation light can be increased, and along with it the amount of fluorescent light emitted by a living body tissue can be increased. This is especially effective when observing objects, such as a stomach wall, which normally are difficult to image in fluorescent light due to the fluorescent emission intensity being weak.

Note that the transmittance ranges of the filters and the transmittance property of the light intensity adjusting means that are used may be changed when necessary for obtaining desired observation images. Also, the light amount adjusting means can be combined with filters on the turret.

In Procedure 2, the light source unit illuminates the object repeatedly and sequentially through the illumination unit of the scope using light in the wavelength ranges shown in FIG. 28. At this time, the turret of the light source unit is rotated so as to insert the optical filter 114 having the spectral transmittance as shown in FIG. 31(e) into the light path. Also, the rotary filter wheel of the light source unit is translated so as to insert the filters on the outer circle of the rotary filter wheel into the light path. Then, the rotary filter wheel is rotated at a constant rate so as to repeatedly insert the optical filters 115, 116, and 117 having transmittance as shown in FIGS. 32(a), 32(b) and 32(c), respectively, into the light path with a constant period.

The optical filter 114 having a transmittance as shown in FIG. 31(e) is formed of a combination of filters arranged in series, as follows: one having a first bandpass transmittance range of 400 nm to 440 nm, one having a second bandpass transmittance range of 505 nm to 535 nm, one having a third bandpass transmittance range of 595 nm to 625 nm, and means to adjust the light intensity so that light of the first wavelength range is transmitted by the filter 114 with about five times the intensity as light in the second wavelength range and light in the third wavelength range.

The optical filter 115 has a transmittance bandpass range, as shown in FIG. 32(a), from 385 nm to 495 nm and is also transmissive for wavelengths longer than 920 nm. When the optical filter 115 is inserted into the light path, light in the blue region having wavelengths from 400 nm to 440 nm is allowed to exit the light source unit.

The optical filter 116 has a transmittance bandpass range of 500 nm to 575 nm and a transmittance bandpass range of 765 nm to 820 nm. When the optical filter 116 is inserted into the light path, light in the green region having wavelengths in the range of 505 nm to 535 nm is allowed to exit the light source unit.

The optical filter 117 is a filter having a transmittance bandpass range of 585 nm to 655 nm and a transmittance bandpass range of 745 nm to 820 nm. When the optical filter 117 is inserted into the light path, light in the red region having a wavelength range of 595 nm to 625 nm is allowed to exit the light source unit.

FIG. 33(a) shows the spectral transmission of an optical filter 122 that is placed in the imaging optical system of the scope. The optical filter 122 transmits light with wavelengths shorter than 715 nm and blocks light in the range from 715 nm to 960 nm. Therefore, this optical filter allows the blue region light, the green region light, and the red region light that is reflected by living body tissue to reach the image surface of the imaging optical system.

Because the illumination intensity ratio of the blue region light is set higher than light in the other wavelength regions, images that clearly show the boundary between lesions and normal tissue in the mucosal layer of living body tissue can be obtained. The transmittance bandpass ranges of the filters and the transmittance property of the light intensity adjusting means may be changed when necessary for obtaining desired observation images.

Figure 34A:
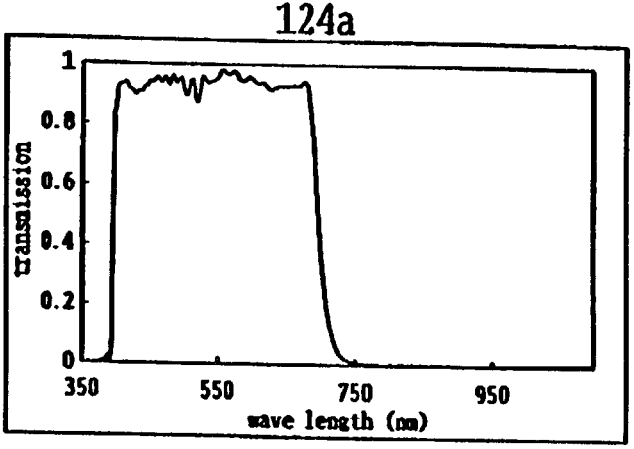
FIGS. 34($a$)-34($c$) show the spectral transmittance of optical filters used in possible modifications to the first embodiment.
Figure 34B:
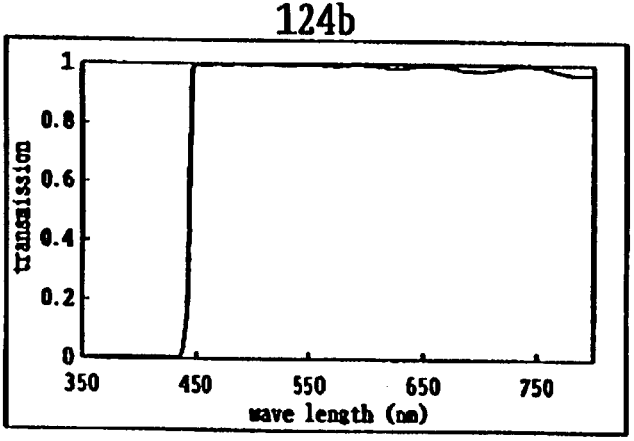
Figure 34C:
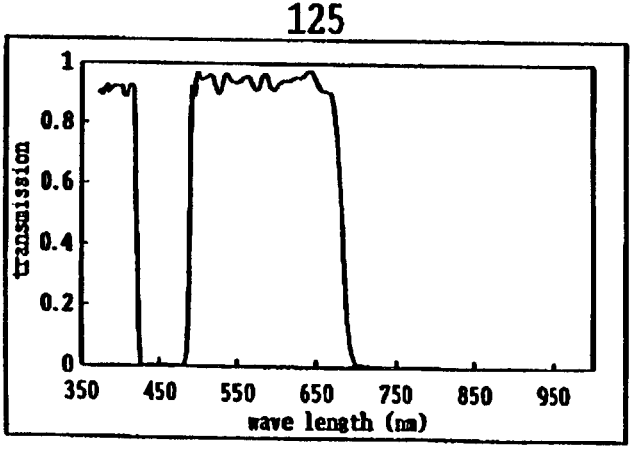

As an example of a possible modification of the combination of optical filters in Procedure 2, an optical filter 125 having a spectral transmittance as shown in FIG. 34(c) may be placed in the scope imaging optical system. The optical filter 125 has a transmittance bandpass range of 495 nm to 690 nm and transmits shorter than 430 nm. Therefore, light of a wavelength range of 400 nm to 430 nm out of the blue region light, the green region light, and the red region light reflected by a living body tissue reaches the image surface of the imaging optical system, and almost the same image can be obtained as in the case of using the optical filter 122.

Also, the imaging optical system where the optical filter 125 is placed can be used for fluorescent image observations. In this case, optical filters are placed in the turret of the light source unit, and these are inserted into the light path. The optical filters are formed of a bandpass filter 124a which has a transmittance bandpass range of 390 nm to 695 nm in series with a filter 124b which transmits light of 445 nm or longer. The bandpass filter 124a is the same as the bandpass filter 12a having a spectral transmittance as shown in FIG. 31(b). By combining the optical filter 125 and the optical filter 118 placed on the inner circle of the rotary filter wheel of the light source unit, excitation light of a wavelength range of 445 nm to 470 nm is allowed to exit the light source unit. Therefore, because excitation light does not reach the image surface of the imaging optical system and instead only the fluorescent light emitted by the living body tissue reaches it, fluorescent images with good contrast can be obtained.

Furthermore, the imaging optical system where the optical filter 125 is placed can be used for ordinary color image observation. In this case, the optical filter 111 in FIG. 31(a) is placed on the turret and inserted into the light path. By combining the optical filter 111 and the optical filters 115, 116, and 117, the latter three of which are arranged on the outer circle of the rotary filter wheel, illumination light of three different wavelength regions in the blue region, green region, and red region are allowed to sequentially exit the light source unit while substantially no light in the near infrared region is allowed to exit the light source unit. Light of a wavelength range of 400 nm to 430 nm out of the blue region light, the green region light, and the red region light reflected by living body tissue is allowed to reach the image surface of the imaging optical system. These monochrome images are then synthesized in the image processing circuit so as to obtain an ordinary color image. Thus, by devising combinations of filters, three kinds of observations can be performed using a single imaging optical system.

In Procedure 3, light in the wavelength regions H and J as shown in FIG. 29 are repeatedly and sequentially projected through the illumination unit of the scope toward the object. At this time, the turret of the light source unit rotates so as to insert the optical filter 113 in FIG. 31(d) into the light path. Also, the rotary filter wheel of the light source unit is translated so that filters positioned within the outer circle of the rotary filter wheel may be rotated into the light path. Then, the rotary filter wheel is rotated at a constant rate so as to insert the optical filters 115, 116, and 117 in FIGS. 32(a)-32(c), respectively, repeatedly into the light path with a constant period.

Figure 31D:
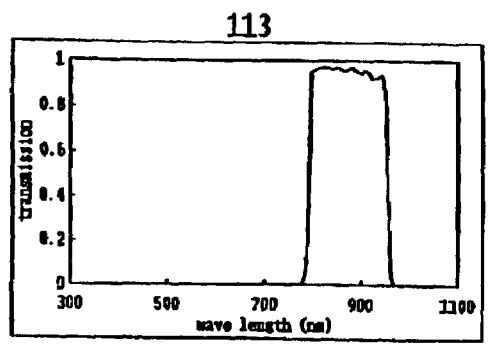
Figure 31E:
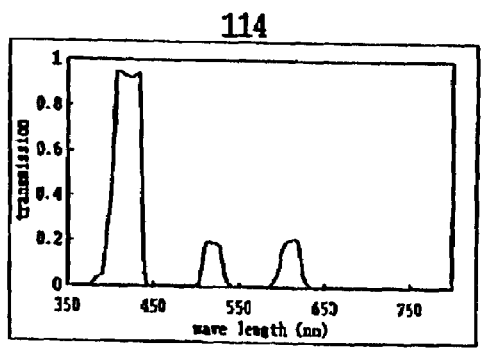

The optical filter 113 in FIG. 31(d) is a filter having a transmittance bandpass range of 790 nm to 950 nm. Because the optical filter 115 is a filter having a transmittance bandpass range of 385 nm to 495 nm and transmits light longer than 920 nm, when the optical filter 115 is inserted into the light path, infrared region light of a wavelength range of 920 nm to 950 nm is allowed to exit the light source unit.

Because the optical filter 116 is a filter having a transmittance bandpass range of 500 nm to 575 nm and a transmittance bandpass range of 765 nm to 820 nm, when the optical filter 116 is inserted into the light path, infrared region light of a wavelength range of 790 nm to 820 nm is allowed to exit the light source unit.

Because the optical filter 117 is a filter having a transmittance bandpass range of 585 nm to 655 nm and a transmittance bandpass range of 745 nm to 820 nm, when the optical filter 117 is inserted into the light path, infrared region light of a wavelength range of 790 nm to 820 nm is allowed to exit the light source unit.

In the imaging optical system of the scope, because at least the infrared region light should be efficiently transmitted and condensed onto the image surface of the imaging optical system, optical filters can be omitted. By using the infrared region light that reaches the image surface to display an image, for example on a monitor, the flow of blood in blood vessels and lymphatics distributed in the lower layer of the mucosa of a living body tissue can be clearly observed. Because of this, whether a lesion such as cancer has infiltrated beyond the mucosal layer can be determined.

In Procedure 4, the light source unit illuminates repeatedly and sequentially light of spectral intensity distributions shown in FIG. 30 through the illumination unit of the scope toward the object. At this time, the turret of the light source unit rotates to insert the optical filter 111 in FIG. 31(a) into the light path. Also, the rotary filter wheel of the light source unit moves to insert the outer circle of the rotary filter wheel into the light path. Then, the rotary filter wheel rotates to insert the optical filters 115, 116, and 117 in FIGS. 32(a)-32(c), respectively, repeatedly at a constant period. Because this combination was already described, the detailed explanation is omitted here.

In order to endoscopically safely treat a lesion such as cancer, it is indispensable to observe the lesion and its surrounding tissue using images which are bright and have good color reproducibility. Also, when burning a lesion in the mucosa using a laser, the light of the laser wavelength must be securely blocked in order to be able to observe the lesion while the laser is active. Then, in the scope imaging optical system, the optical filter 122 in FIG. 33(a) is used.

The optical filter 122 transmits light having wavelengths shorter than 715 nm and blocks light in the wavelength range of 715 nm to 960 nm. Blue light of a wavelength range of 390 nm to 495 nm, green light of a wavelength range of 500 nm to 575 nm, and red light of a wavelength range of 585 nm to 655 nm reflected by the living body tissue reach the image surface of the imaging optical system. If light from these filters is combined after being reflected from an object, almost the entire range of the visible wavelength is represented. Because of this, bright color images which have good color reproducibility can be obtained. Also, because near-infrared light from semiconductor lasers in the range of 775 nm to 875 nm is blocked by the optical filter 122, the lesion can be clearly observed even during semiconductor laser irradiation. However, if YAG laser irradiation is used, in addition to using the optical filter 122, a filter which blocks light of wavelengths 960 nm or shorter must be added in order to obtain good observation images.

According to this embodiment, illumination light having the needed spectral contents for performing the series of observations can be created by a single light source unit. Because of this, the conventional troublesome work of exchanging the light source unit every time the kind of special light observation is changed becomes unnecessary.

Because multiple kinds of observations can be performed with a single imaging optical system, the labor to exchange the scope every time the kind of observation is changed and the pain to the patient can be reduced. Especially, by using a scope equipped with two imaging optical systems where filters having different spectral transmittance properties are placed, it becomes possible to perform a complete series of observation procedures without exchanging the scope.

In this embodiment, in order to perform multiple kinds of observations with a single imaging optical system, blue region light is divided into two bands. Light in one band is utilized as the excitation light for fluorescent image observations, and light in the other band is utilized as illumination light for the other observations. Therefore, it is desirable to install the following devices to the filters placed in the light source unit, imaging optical system, and the light guide forming the scope illumination unit.

In manufacturing the light guide, it is desirable to use materials which do not absorb light at short wavelengths, such as quartz. Thus, the phenomenon such as seen in the spectral intensity curve E in FIG. 28 where the illumination intensity rapidly decreases as the wavelength becomes shorter can be avoided. If a filter is one wherein layers of interference films are vapor coated on a glass substrate, it is desirable to make the interference films of a material such as tantalum (Ta), etc., which does not absorb light at short wavelengths.

Figure 35A:
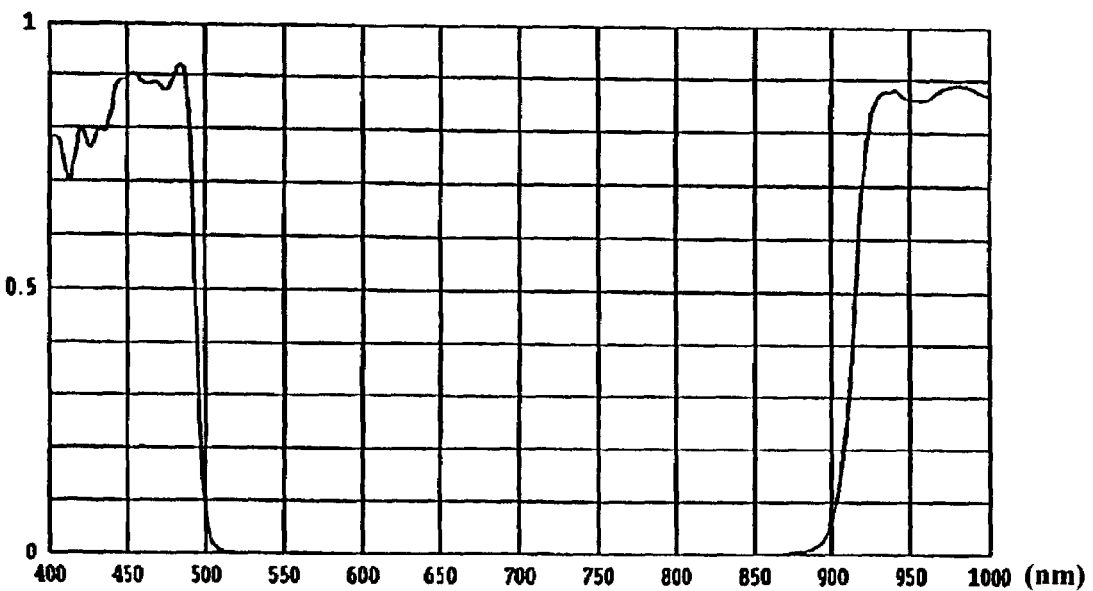
FIGS. 35(*a*) and 35(*b*) show the spectral transmittance of the optical filter 115 for a case using a film which does not absorb much light in short wavelengths and for a case using a film which does absorb light in short wavelengths.
Figure 35B:
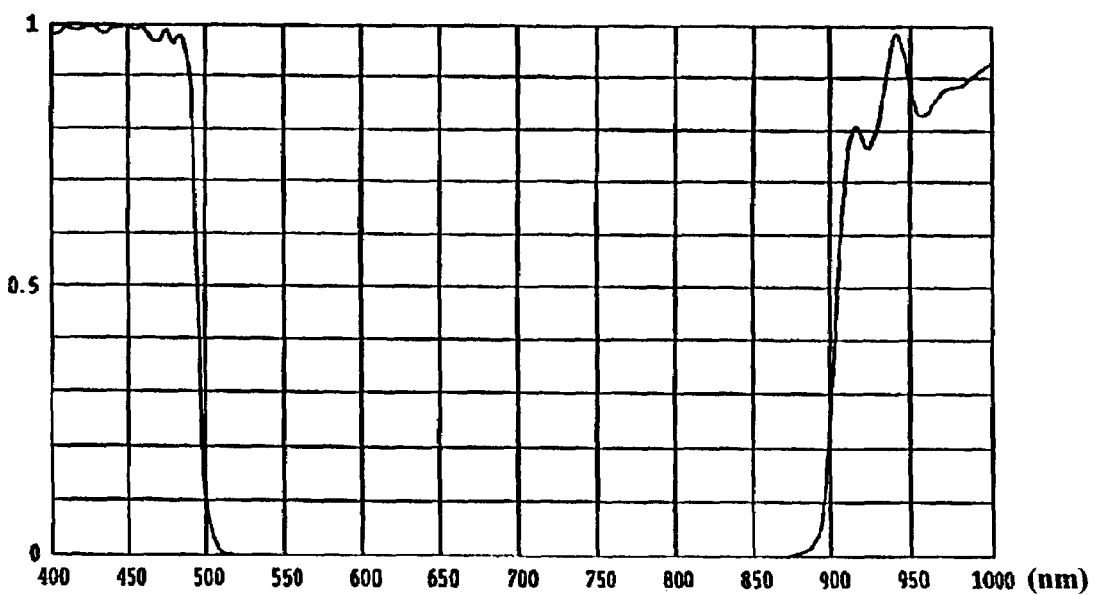

For example, in the optical filter 115, both sides of a glass substrate are vapor coated with 30 to 50 layers of interference film. In the optical filter 115, the spectral transmittance properties when a film-forming material which does not absorb much short wavelength light and the spectral transmittance properties when a film-forming material which does absorb short wavelength light are compared in FIGS. 35(*a*) and 35(*b*). Shown in FIG. 35(*a*) is the spectral transmittance property plot when the multilayer interference film is constructed using titanium (Ti) and silicon (Si) as the film-forming materials. Shown in FIG. 35(*b*) is the spectral transmittance when the multilayer interference film is constructed by replacing titanium (Ti) with tantalum (Ta) in the film-forming materials. As is clear from FIGS. 35(*a*) and 35(*b*), by using a material such as tantalum (Ta) which does not absorb as much short wavelength light as a film-forming material, transmittance properties in the blue region can be improved. Also, it becomes possible to utilize ultraviolet region light as excitation light using such multilayer interference films.

Figure 36:
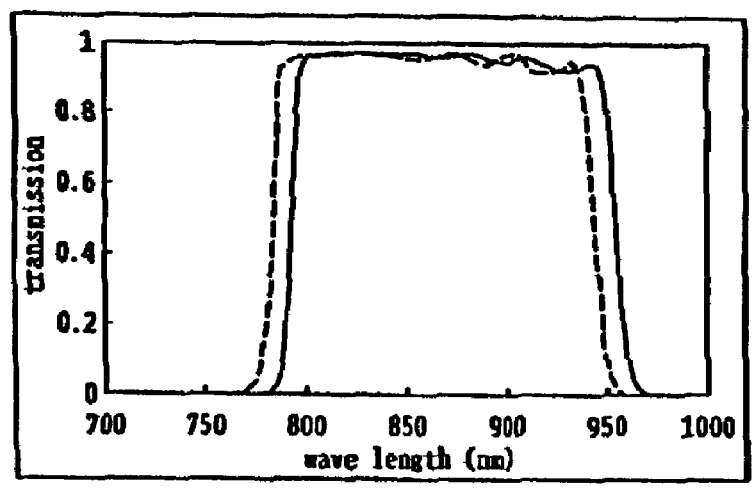
FIG. 36 shows the change in the spectral transmittance of the optical filter 123 when the thermal load is changed.

In this embodiment, the turret of the light source unit is placed immediately after a lamp. Because of this, an optical filter that is placed on the turret when inserted into the light emitted from the lamp receives a significant thermal load. If the optical filter is used in such a state, the spectral transmittance properties may change with time. As an example, changes in the spectral transmittance properties of the optical filter 123 are shown in FIG. 36. The solid-line curve in FIG. 36 represents the spectral transmittance properties of an optical filter before a thermal load has changed its spectral transmittance distribution, and the dashed line represents the spectral transmittance distribution after 60 minutes have passed since the thermal load was applied. As is apparent from comparing these two lines, when a thermal load is applied to the optical filter 123, its transmittance region shifts gradually toward the shorter wavelengths with time. After the thermal load has been applied for about 60 minutes, the transmittance region becomes stable. At this time, the amount of shift in the spectral transmittance region has been 6 nm to 10 nm.

Special light observations may require a living body tissue to be illuminated with light in very narrow wavelength ranges, with information specific to those wavelength ranges being obtained after the light has been reflected by living body tissue. Therefore, it is required to maintain the illumination light constant in spectral content and intensity during such an observation. If the spectral transmittance properties of the optical filter change during an observation, reliable information concerning the cancerous state of living body tissue cannot be obtained and a correct diagnosis of the lesion will be greatly impaired.

The change in spectral transmittance of an optical filter due to thermal loading as discussed above is caused by water vapor which enters interlayer spaces that are created when the interference layers are applied. Although the spectral transmittance properties change as a result of the thermal load driving out the water vapor (i.e., reducing the relative humidity), once this occurs, the optical performance of the filter becomes stable. Unfortunately, when the thermal load is no longer present, the optical filter cools to ambient temperature. Because this will allow the water vapor in the atmosphere to again enter the spaces so as to increase the relative humidity at ambient temperature, the inconvenience of the optical filter having transmittance properties that change with thermal loading during the first 60 minutes of each use will never cease.

Therefore, the optical filters of the present invention are preferably manufactured by a film-forming method which does not generate interlayer spaces when applying the interference layers. More specifically, a known film-forming method using an ion gun and termed "ion assisting" or "ion plating" may be used to manufacture the optical filters. Because these film-forming methods strengthen the bonding power of the film-forming materials, no interlayer space is formed. As a result, optical filters can be provided which have spectral transmittance properties that do not change even when a thermal load is applied. Note that the filters used in this embodiment may consist of a single filter or multiple filters in series. Also, filters that are arranged on the rotary filter wheel 10 may be placed on either the outer circle or the inner circle of the rotary filter wheel containing concentric arrangements of filters.

Figure 37:
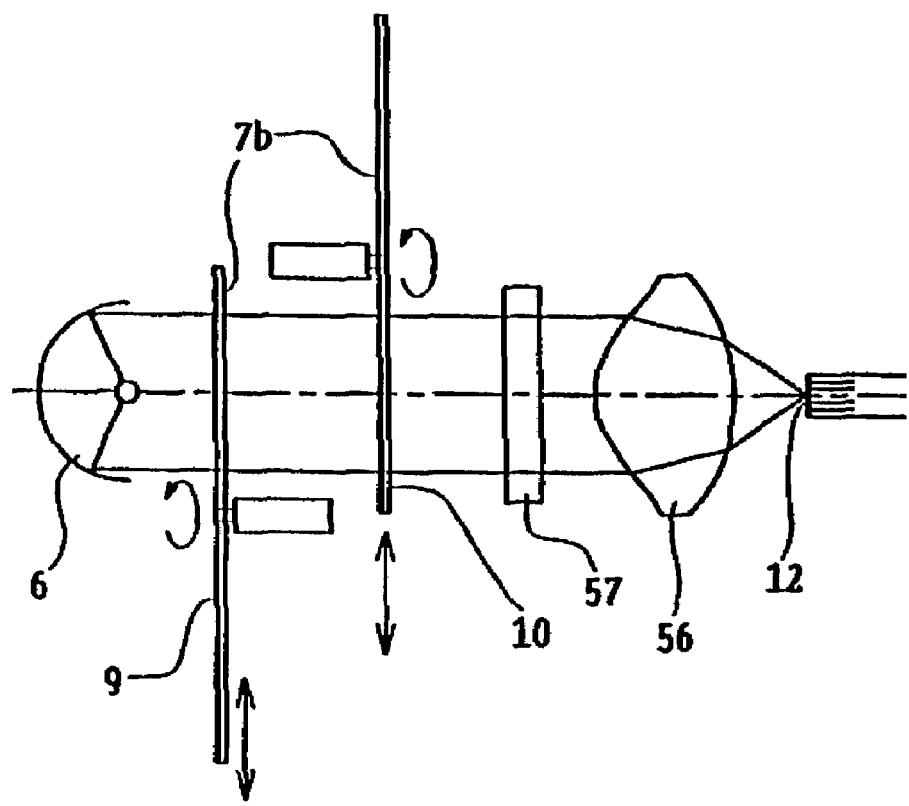
FIG. 37 shows the configuration of the optical system of the light source unit used in the second embodiment.
Figure 38:
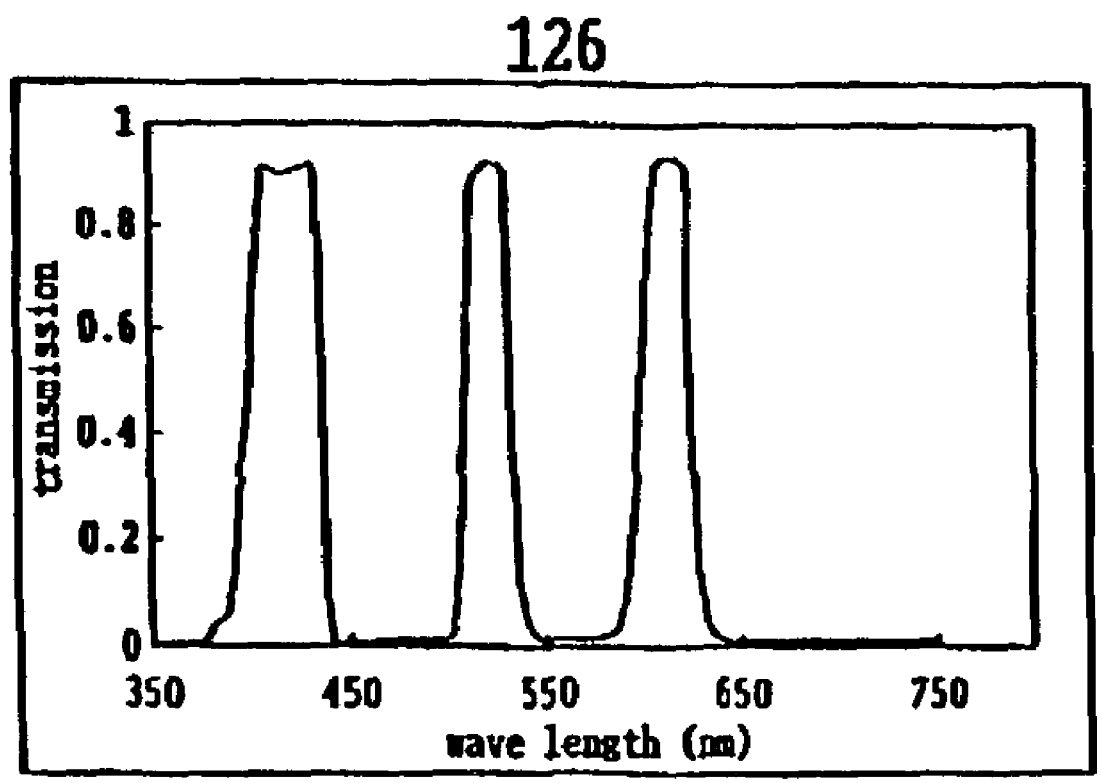
FIG. 38 shows the spectral transmittance of the optical filters placed on the turret of the light source unit used in the second embodiment.

FIGS. 37-39(*c*) relate to a second embodiment of the present invention. FIG. 37 shows the configuration of the optical system of the light source unit according to the second embodiment. FIG. 38 shows the spectral transmittance of optical filters placed on the turret of the light source unit according to the second embodiment, and FIGS. 39(*a*)-39(*c*) show the spectral transmittance of optical filters placed on the rotary filter wheel according to the second embodiment. Because the basic device configuration and filter combination method are the same as that discussed above for the first embodiment, only the differences will now be described.

In special light observations, there are cases where image quality will vary greatly depending on the particular living tissue being observed and the technique used to perform the observation. For example, observing the stomach wall is made difficult because numerous tissues which project toward the interior of the stomach are distributed on the stomach wall, and the mucosal surface is covered with a secretion which functions to protect the stomach wall from stomach acid. Because of this, a high proportion of the illumination light is absorbed and scattered by the mucosal surface, and the amount of light reflected from the mucosal layer changes every time the observation state changes. According to the second embodiment of the invention, the relative intensity of the illumination light can be changed when necessary according to the observation state so that observation images of stable quality can be provided.

FIG. 37 shows the configuration of the optical system of the light source unit used in the second embodiment. The optical system is formed of a lens 56 which condenses a light flux emitted from an aperture window of a lamp 6 onto an end surface 12 of the light guide of a scope. A turret 9, a rotary filter wheel 10, and a transmitted light amount adjusting means 57 are placed between the lamp 6 and the lens 56. As illustrated by the double-headed arrows, both the turret 9 and the rotary filter wheel 10 of this embodiment may be translated within planes that are substantially normal to the light path direction.

A transmitted light amount adjusting means 57 functions to reduce the light intensity that is incident onto the end surface 12 of the light guide by a desired factor. Also, the light flux reduction rate can be varied in synchronism to the rotation period of the rotary filter wheel 10. In addition, it can be set up so that the rate of light reduction varies automatically based on a brightness correction signal that is fed back while processing images taken by the imaging unit. For example, when performing an observation in Procedure 2 among the series of observation procedures discussed above with regard to the first embodiment, an optical filter 126 having a spectral transmittance distribution as shown in FIG. 38 that is placed on the turret 9 may be inserted into the light path.

The optical filter 126 has a transmittance bandpass range of 400 nm to 440 nm, a transmittance bandpass range of 505 nm to 535 nm, and a transmittance bandpass range of 595 nm to 625 nm. When used in series with the optical filters 115, 116, and 117 (having spectral transmittance as shown in FIGS. 32(a), 32(b), and 32(c), respectively) that are arranged on the outer circle of the rotary filter wheel 10, light in the blue region having wavelengths in the range of 400 nm to 440 nm, light in the green region having wavelengths in the range of 505 nm to 535 nm, and light in the red region having wavelengths in the range of 595 nm to 625 nm are allowed to exit the light source unit. When used in synchronization with the rotary filter wheel 10, the transmitted light amount adjusting means 57 adjusts the amount of transmitted light so that light in the three wavelength regions of red, green and blue have the desired intensity ratios.

Also, according to the observation state, the ratios of light in the three wavelength ranges may be adjusted. Thus, observation images having a stable image quality can be obtained, independent of the living tissue that is observed or of the observation state.

As an example of a possible modification, the transmitted light amount adjusting means can be placed in the imaging unit. For example, an optical element which has a property that its transmittance distribution may be varied can be placed at the aperture stop position 63 (FIG. 7), or in that vicinity, of the objective optical system. The optical element can be made to vary its transmittance distribution in synchronism with the illumination periods of light in each wavelength range, thereby enabling the amount of light in each wavelength region that reaches the detecting surface of the image sensing chip 67 (FIG. 7) to be controlled.

When performing observation Procedure 1, among the series of observation procedures discussed in the first embodiment using an imaging unit with this kind of configuration, optical filters in the light source unit are used as will now be discussed.

Figure 39A:
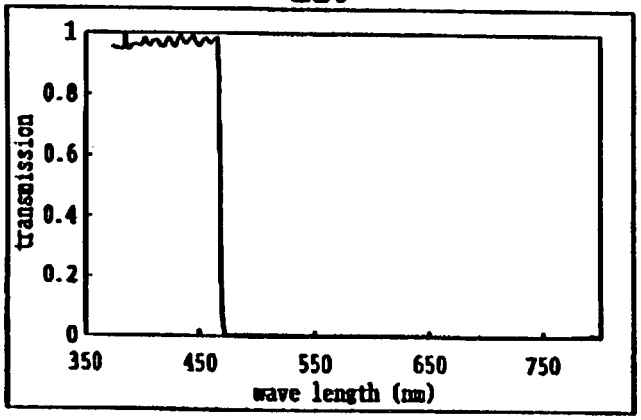
FIGS. 39(*a*)-39(*c*) show the spectral transmittance of the optical filters placed in the imaging optical system of the scope used in the second embodiment.
Figure 39B:
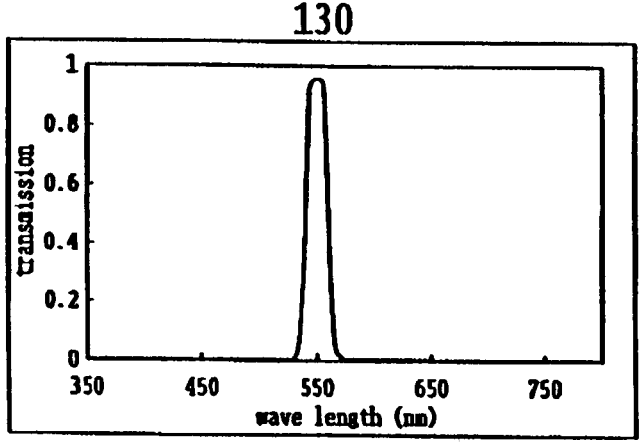
Figure 39C:
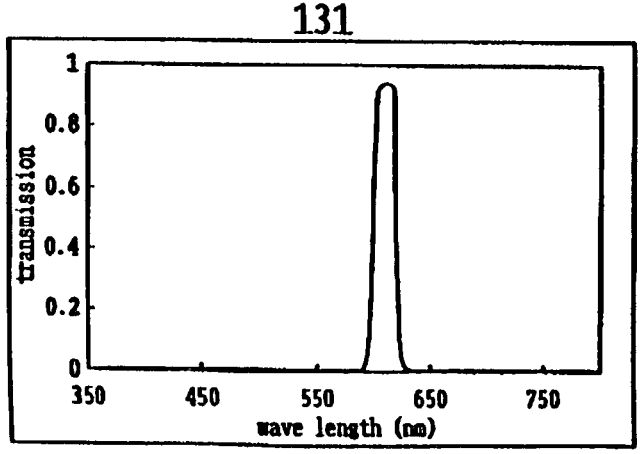

The optical filters 112(a) and 112(b) having spectral transmittance as shown in FIGS. 31(b) and 31(c) are placed in series within a single window of a turret 9 and then inserted into the light path. Optical filters 129, 130, and 131 having spectral transmittance as shown in FIGS. 39(a), 39(b) and 39(c), respectively, are arranged on the inner circle of a rotary filter wheel 10 and are repeatedly rotated into the light path with a constant period. The optical filter 129 in FIG. 39(a) transmits light of wavelengths 470 nm or shorter. When the optical filter 129 is inserted into the light path, excitation light of a wavelength range of 390 nm to 445 nm is allowed to exit the light source unit. The optical filter 130 has a spectral transmittance as shown in FIG. 39(b), namely, wavelengths in the range of 540 nm to 560 nm are transmitted. When the optical filter 130 is inserted into the light path, light of a wavelength range of 540 nm to 560 nm is allowed to exit the light source unit. The optical filter 131 having a spectral transmittance as shown in FIG. 39(c), namely, wavelengths in the range of 600 nm to 620 nm are transmitted. When the optical filter 131 is inserted into the light path, light of a wavelength range of 600 nm to 620 nm is allowed to exit the light source unit.

Light in these different wavelength ranges are sequentially made to be incident onto living body tissue through the illumination unit of a scope, and fluorescence and reflected light from the living body tissue are received by the imaging unit. A transmitted light amount adjusting means that is positioned at the aperture stop position of the imaging unit or its vicinity transmits 100% of the fluorescence in synchronism with the illumination period of the excitation light. Also, it reduces the reflected light by a factor in the range of 1/500 to 1/1000 in synchronism with the illumination period of the light in the other wavelength ranges.

In this instance, the excitation light is blocked by the optical filter 121 (having a spectral transmittance as shown in FIG. 33(c)) that is placed in the filter position 64 near the aperture stop position 63, and thus only the fluorescence and reflected light reach the detection surface of the image sensing chip 67, as shown in FIG. 7. Image signals from the image sensing chip are fed back to a driving circuit of the transmitted light amount adjusting means and, according to the brightness correction value calculated based on the standard light amount ratio data stored in a memory of the driving circuit, the light reduction rate is automatically adjusted. Thus, independent from the observed tissue or observation state, observation images of stable quality can be provided.

In a scope having two observation windows installed on its insertion tip, an optical unit equipped with lens(es) and filter(s) may be positioned behind each observation window, and an image sensing chip may be placed behind the optical units so as to receive input light from each window. The transmitted light amount adjusting means may be placed immediately before the image sensing chip and constructed so that the transmittance of light flux from each objective lens and filter can be individually controlled.

Figure 40B:
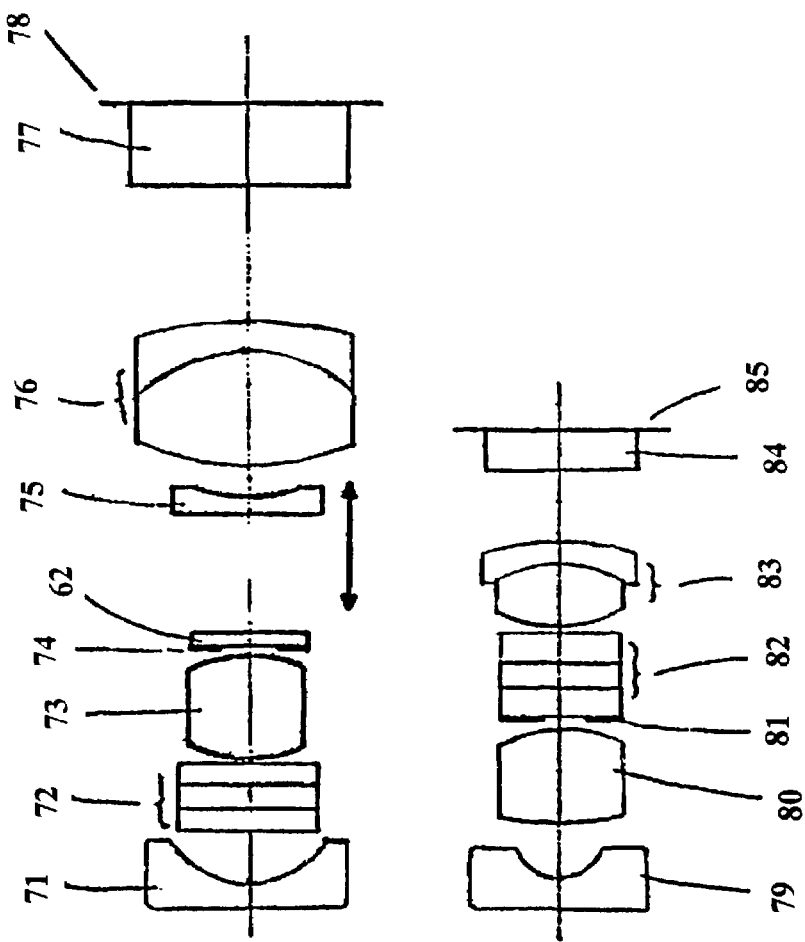
FIGS. 40(*a*) and 40(*b*), FIGS. 40(*c*) and 40(*d*), and FIGS. 40(*e*) and 40(*f*) show three types of optical systems that can be used in the endoscope systems of the invention.
Figure 40A:
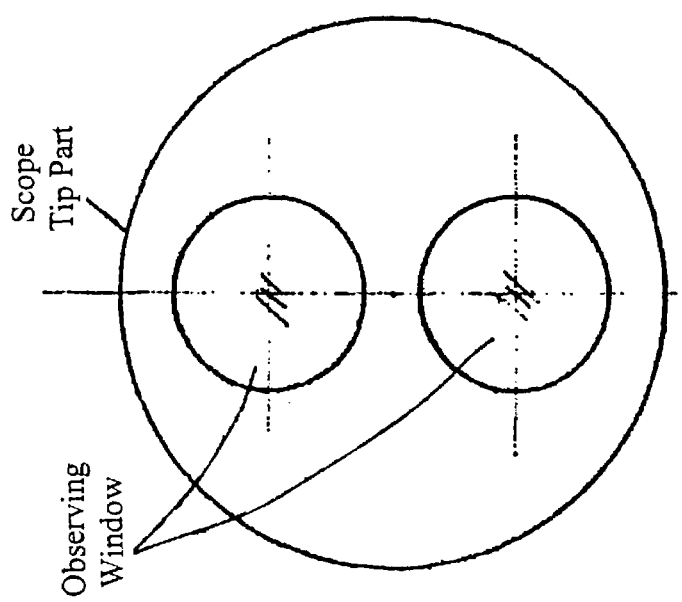
Figure 40D:
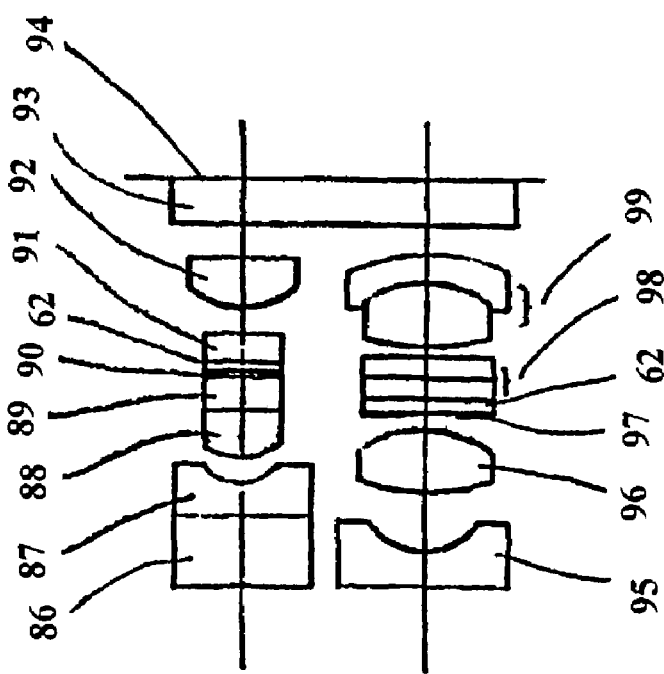
Figure 40C:
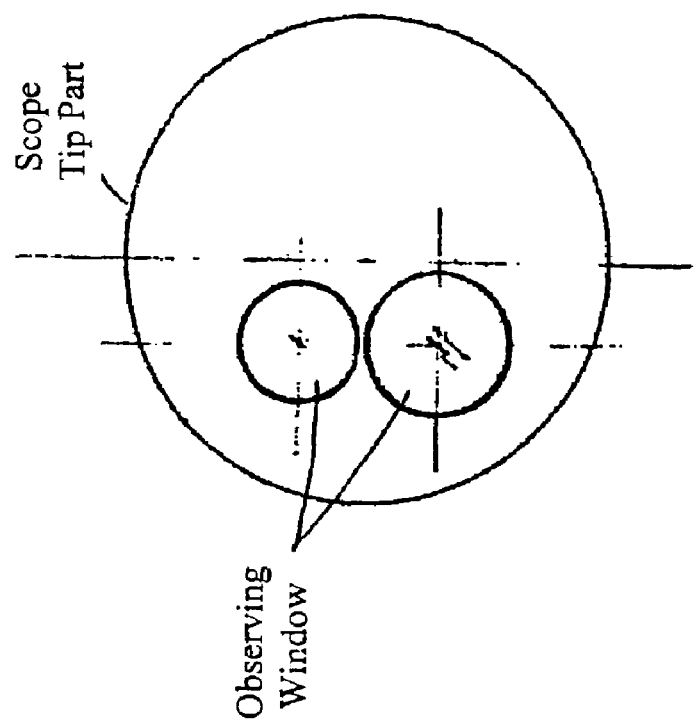
Figure 40F:
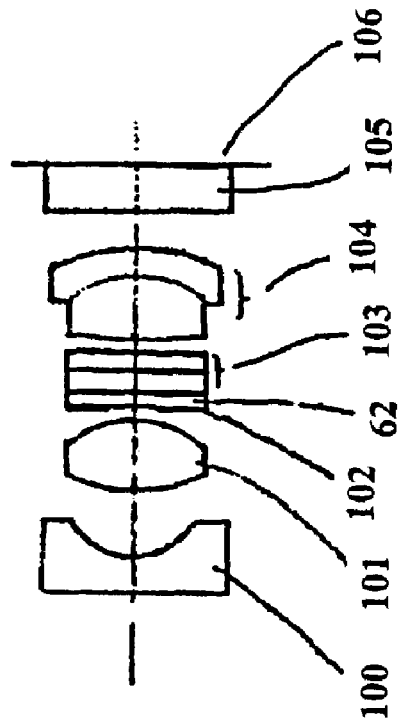
Figure 40E:
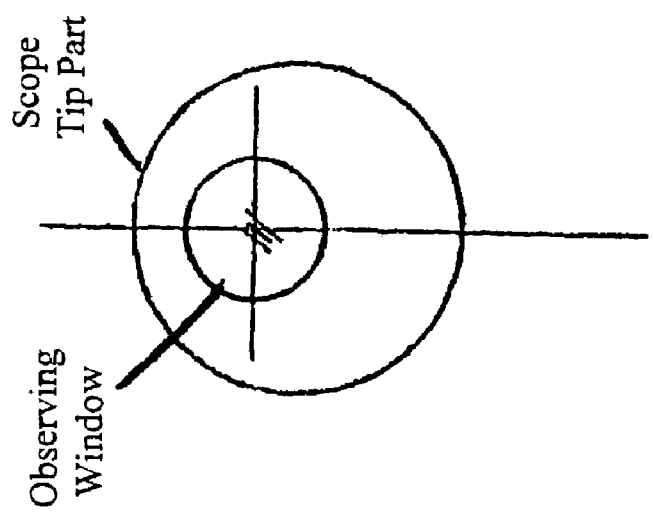

FIGS. 40(a), 40(c) and 40(e) are front views of the scope tip portions of the insertable part of endoscopes in which only the observation windows are shown, with other elements having been omitted, for convenience of illustration. FIGS. 40(b), 40(d) and 40(f) are side, sectional views of the image pickup units that may be used with the scope tip observation windows shown in FIGS. 40(a), 40(c), and 40(e), respectively. The image pickup units are formed of lenses, filters, and image pickup devices.

As shown in FIG. 40(a), the endoscope may have two observation windows arranged almost on the centerline of the tip portion of the endoscope and two image pickup units, one for each observation window.

FIG. 40(b) shows the lens layout of the objective lens systems of each of the two image pickup units used with the observation windows of FIG. 40(a). One objective lens system is a variable focal length system that is formed of, in order from the object side, a plano-concave lens 71, an optical filter array 72 that serves to eliminate undesired light, a biconvex lens 73, an aperture stop 74, a spatial frequency conversion means 62, a plano-concave lens 75 that is movable along the optical axis, and a cemented lens doublet 76 that is formed of a biconvex lens cemented to a negative meniscus lens. The image pickup device 78 is arranged at the exit side of the objective lens system. The numeral 77 indicates a cover glass for protecting the light-detecting surface of the image pickup device. The other objective lens system has a fixed focal length, and is formed of, in order from the object side, a plano-concave lens 79, a biconvex lens 80, an aperture stop 81, an optical filter array 82 that serves to eliminate undesired light, a cemented lens doublet 83 that is formed of a biconvex lens cemented to a negative meniscus lens. The image pickup device 85 is arranged at the exit side of the objective lens system. The numeral 84 indicates a cover glass for protecting the light-detecting surface of the image pickup device.

For example, one image pickup unit can be used for obtaining an ordinary color image and a fluorescent image, and the other image pickup unit can be used for obtaining an ordinary color image and an infrared image. According to the present invention, three kinds of images, namely, an ordinary color image, a fluorescent image and an infrared image can be obtained using a single endoscope. Of course, different kinds of images can be provided by substituting other filter arrays for the filter arrays 72 and 82. In the case where one image pickup unit is used for infrared observation as stated above, an optical substrate such as a glass plate coated with anti-reflection films on both surfaces may be used instead of the filter array 82.

As illustrated in FIG. 40(c), the endoscope may alternatively have two observation windows arranged on one side of the centerline of the tip portion of the endoscope, in which case the endoscope is provided with two image pickup units. FIG. 40(d) shows the lens layout of the objective lens systems, both of which are fixed focal length systems, of each of the two image pickup units for the scope tip shown in FIG. 40(c). One objective lens system is formed of, in order from the object side, a plane parallel glass plate 86, a plano-concave lens 87, a piano-convex lens 88, an optical filter array 89 that serves to eliminate undesired light, an aperture stop 90, a spatial frequency conversion means 62, an optical filter array 91 that serves to eliminate undesired light, and a plano-convex lens 92. The other objective lens is formed of, in order from the object side, a plano-concave lens 95, a biconvex lens 96, an aperture stop 97, a spatial frequency conversion means 62, an optical filter array 98 that serves to eliminate undesired light, and a cemented lens doublet 99 that is formed of a biconvex lens cemented to a negative meniscus lens.

As shown in FIG. 40(d), a single image pickup device 94 is arranged at a common image plane of the two objective lens systems so that light is received from each of the objective lens systems. The numeral 93 indicates a cover glass for protecting the light-detecting surface of the image pickup device 94. In this example, in the case where the image pickup unit is used for infrared observation, an optical substrate, such as a glass plate, is coated with anti-reflection films on both surfaces and is used instead of the filter array 98. This type of image pickup unit is small in size because only one image pickup device is used in common for the two objective lens systems, and this allows the tip end of the insertion portion to be made smaller.

As shown in FIG. 40(e), the endoscope may alternatively have one observation window and one image pickup unit. FIG. 40(f) shows the lens layout of an objective lens system of the image pickup unit having a fixed focal length which may be used. The objective lens system is formed of, in order from the object side, a plano-concave lens 100, a biconvex lens 101, an aperture stop 102, a spatial frequency conversion means 62, an optical filter array 103 that serves to eliminate undesired light, and a cemented lens doublet 104 that is formed of a biconvex lens that is cemented to a negative meniscus lens.

An image pickup device 106 is arranged at the image surface of the objective lens system. The numeral 105 indicates a cover glass for protecting the light-detecting surface of the image pickup device 106.

This type of image pickup unit is small in size because only one image pickup unit is used and this allows the tip end of the insertion portion to be thin. The filter array can be composed of one or a plurality of filters.

By using the endoscope apparatus and endoscope diagnosing method of the present invention, and by combining ordinary color image observations and multiple special light observations, the task of correctly diagnosing and treating lesions can be performed efficiently.

Various examples will now be given concerning how the light amount adjusting means of the present invention may be implemented.

EXAMPLE 1

As a first example of a light amount adjusting means that may used in conjunction with the present invention, a DMD may be used as disclosed in U.S. Pat. No. 6,464,633,the subject matter of which is hereby incorporated by reference.

EXAMPLE 2

Figure 41A:
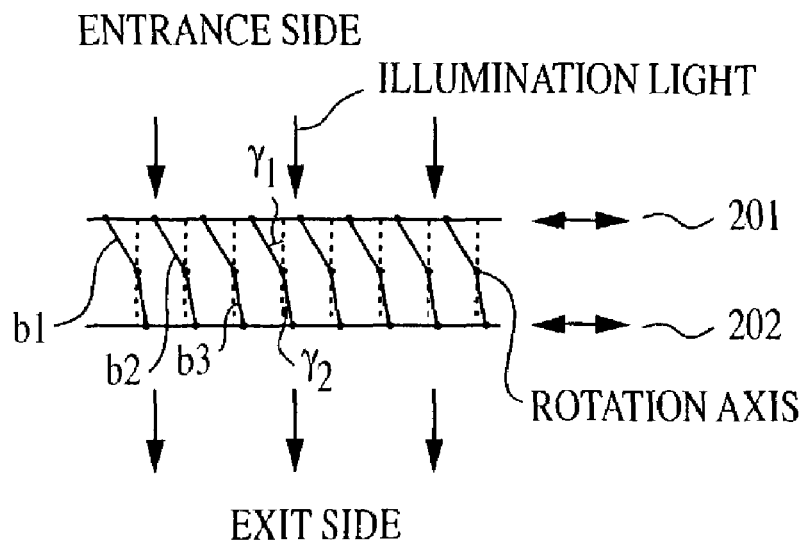
FIGS. 41(*a*) and 41(*b*) are top and side views, respectively, of an example of a light amount adjusting means that may be used in conjunction with the present invention.
Figure 41B:
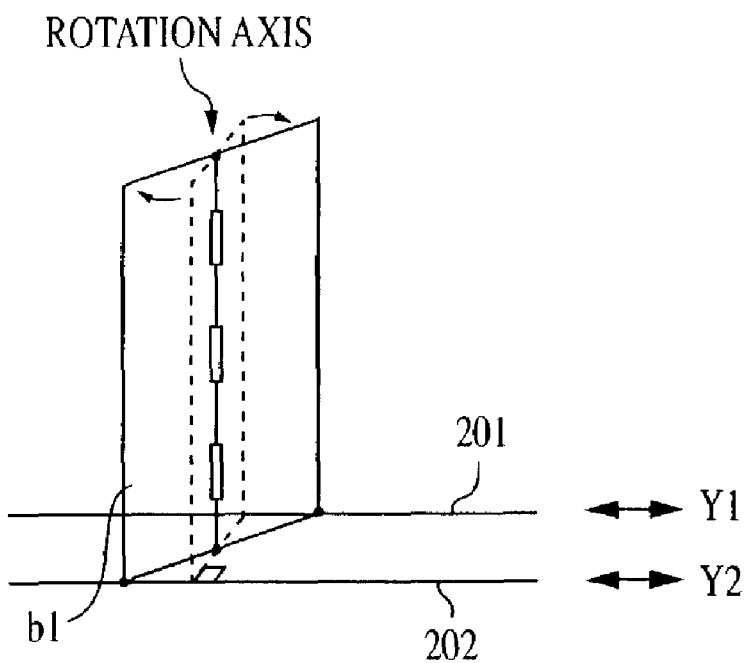

FIG. 41(a) is a top view, and FIG. 41(b) is an oblique view of a light amount adjusting means of Example 2.

The blades b1, b2, etc., have rotation axes and each blade is supported by an upper side support member and a lower side support member (not shown) at its top end and bottom end, respectively. As shown in FIG. 41(b), first and second driving members 201 and 202 are provided, with the right bottom corner of each blade fixed to the first driving member 201 and the left bottom corner of each blade fixed to the second driving member 202. The first and second driving members are slidable along parallel axes as shown by the double-headed arrows Y1 and Y2.

The light amount adjusting means is positioned in the light path of the illumination light from the light source such that a plane that is parallel to the rotation axes as well as the direction of motion of the first and second driving members is substantially perpendicular to the central axis of the illumination light flux.

In this structure, when the blades b1, b2, etc., are positioned so as to be parallel to the central axis of the light flux, illumination light passes freely between interstices of the blades so that a maximum amount of light passes through the light amount adjusting means. This position of the blades is shown by the dotted lines in FIG. 41(a). The length of each blade is large enough to cover the cross section of the illumination light flux.

When the first driving member 201 moves toward the left a distance and the second driving member 202 moves toward the right an equal distance, each of the blades inclines by the same angle from the original position, and the cross-sections of the interstices between the blades, when viewed in a direction parallel to the central axis, decrease.

In the case where the blades b1, b2, etc., are made of flexible material such as a thin metal or plastic plate, the blades may be deformed depending on the movement of the first and second driving member. In FIG. 41(a), the movement of the first driving member 201 toward the left is larger than the movement of the second driving member 202 toward the right. Therefore the blades are deformed at the rotation axis so that the top portion of each blade makes an angle γ1 from the original position and the bottom portion of each blade makes an angle γ2 from the original position, as illustrated. In either case, the illumination light amount may be readily controlled by the light amount adjusting means.

EXAMPLE 3

Figure 42:
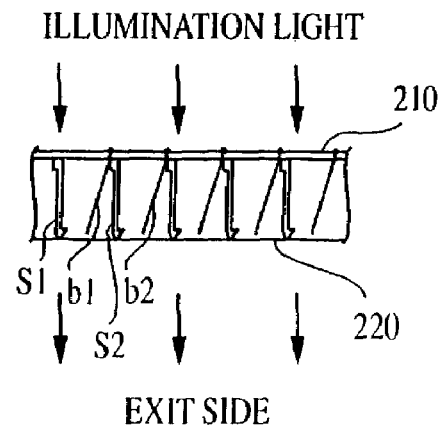
FIG. 42 is a top view of another example of a light amount adjusting means that may be used with the present invention.

FIG. 42 is a top view of a light adjusting means according to Example 3, and FIGS. 43(a)-43(e) are partial, top views for explaining the function of this example.

The light adjusting means of this example is provided with a first support frame 210 and a second support frame 220. The blades b1, b2, etc., each has a rotation axis on the side nearest the illumination, and these rotation axes are supported by the first support frame 210. The blades b1, b2, etc., are made of electrically conductive material and connected to circuitry (not shown in FIG. 42) via the rotation axes. The blades b1, b2, etc., are always charged with negative charges.

Figure 43A:
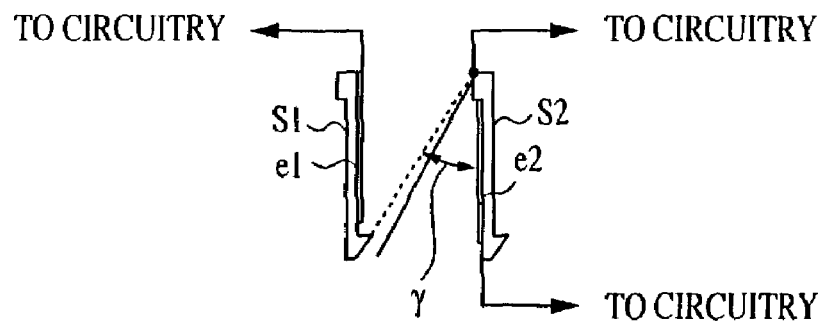
FIGS. 43(*a*)-43(*e*) are partial top views for explaining the function of the light amount adjusting means shown in FIG. 42.
Figure 43B:
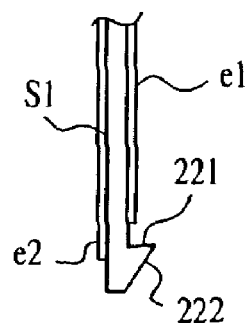

Electric insulator plates S1, S2, etc., are supported at their four corners by the first and second support frames 210 and 220 and positioned parallel with each other so as to be aligned with the illumination light (i.e., perpendicular to the support frames 210 and 220). Each of the electric insulator plates S1, S2, etc., is made of a material having a high heat conductivity and has a respective electrode e1, e2 attached thereto, as indicated in FIG. 43(a). As shown best in FIGS. 43(b) and 43(c), each insulator plate also has a protrusion 221, 230 at its lower and upper end, respectively. The top surface of the upper protrusion 230 is formed as a plane that is perpendicular to the side surfaces of the insulator plate and thus parallel to the support frame 210. The top surface 221 of the lower protrusion is also formed as a plane that is parallel to the top surface of the upper protrusion, but the side surface 222 of the lower protrusion is inclined to the side surface of the of the insulator plates, as shown in FIG. 43(b). The electrodes e1 and e2 are connected to circuitry for supplying a charge of a specified polarity and strength.

Figure 43C:
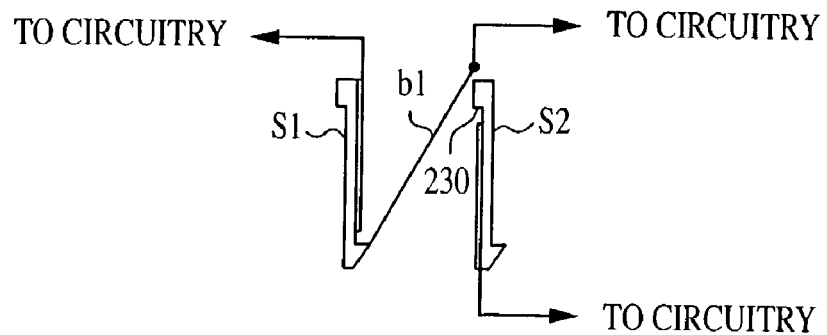
Figure 43D:
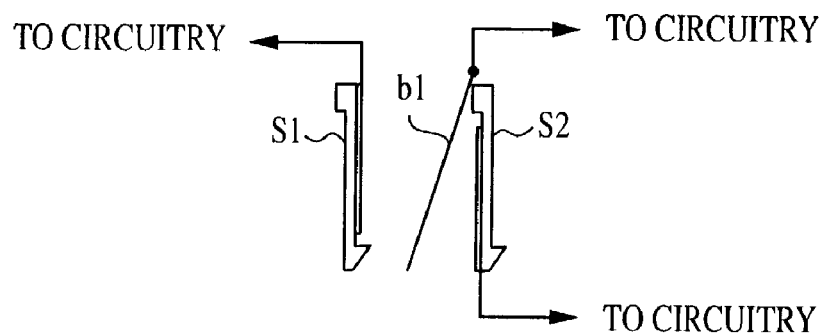
Figure 43E:
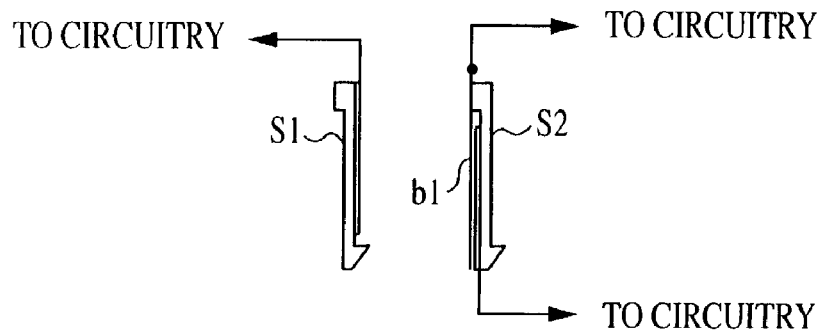

Referring to FIG. 43(e), when the electric circuitry applies a negative electric charge to the electrode e1, the blade b1 moves toward the electrode e2 by the repulsive force between the blade b1 and the electrode e1, and stops in a position parallel to the insulator plate S2 by contacting a surface of the upper protrusion 230. In this position, illumination light passes the fully open interstices between the insulator plates S1 and S2 so that a maximum amount of light passes through the light amount adjusting means.

On the other hand, as illustrated in FIGS. 43(b) and 43(c), when the circuitry applies a negative charge to the electrode e2, the blade b1 moves so as to abut the slanted surface 222 of the protrusion 221. In this position, the illumination light is fully shielded by the blade b1 and the amount of light passing through the light amount adjusting means becomes a minimum (near zero).

As shown in FIGS. 43(b) and 43(d), when the electric circuitry applies negative electric charges to both the electrodes e1 and e2, the blade b1 rotates to a position intermediate between the electrodes e1 and e2. The intermediate position depends on a balance in the amount of electric charge applied to the electrodes e1 and e2. By changing the balance amount of electric charge on the electrodes e1 and e2, the amount of light passing through the light amount adjusting means may be controlled.

When the light amount adjusting means is placed near a light source, heat radiation from the light source is applied to the blades, causing them to be heated to a high temperature. However, by contacting a protrusion formed on the insulator plate that is made of a material having a high heat conductivity, heat is able to escape from the blade through such contact. This serves to prevent overheating. In this example as well as in Example 2, the blades and insulator plates can be made by a known etching process that is used in manufacturing semiconductor devices.

The invention being thus described, it will be obvious that the same may be varied in many ways. For example, as mentioned above, the transmittance bandpass ranges of the filters and the transmittance property of the light amount adjusting means that are used may be changed when necessary for obtaining desired observation images. Also, the light amount adjusting means can be combined with filters on the turret. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An endoscope illumination apparatus comprising:
    a light source for emitting illumination light along an optical axis of an optical path;
    a condensing lens system; and
    means which provides selection of each illumination mode of the following four different illumination modes:
        illumination mode 1—a mode that sequentially transmits excitation light for obtaining fluorescence from living body tissue and light having wavelength components different from the excitation light so as to obtain information from living body tissue other than by using fluorescence,
        illumination mode 2—a mode that sequentially transmits red, green, and blue wavelength ranges of light for obtaining color images of living body tissue,
        illumination mode 3—a mode which sequentially transmits very narrow wavelength ranges of at least two different wavelength regions within the visible spectrum, said wavelength ranges being more narrow than used in illumination mode 2, for enhancing the resolution of blood vessel structures at selected depths from the surface of living body tissue, one of said at least two different wavelength regions being light having wavelengths shorter than 440 nm, and
        illumination mode 4—a mode which sequentially transmits infrared region light having at least two different wavelength ranges for obtaining infrared images of living body tissue; wherein
    said means comprises a turret which is equipped with at least three optical filters having different spectral transmittance;
    a rotary filter wheel which is equipped with at least one set of optical filters arranged on the rotary filter wheel in a concentric pattern;

at least one optical filter of the turret transmits light in at least two wavelength ranges;

at least one optical filter of the rotary filter wheel transmits light in at least two wavelength ranges; and another of said at least two different wavelength regions of illumination mode 3 being the green region, the intensity of illumination light in the green region for illumination mode 3 being less than the intensity of said illumination light for illumination mode 3 having wavelengths shorter than 440 nm.

2. The endoscope illumination apparatus as set forth in claim 1, wherein the intensity of illumination light in the green region is about one-fifth the intensity of said illumination light for illumination mode 3 having wavelengths shorter than 440 nm.

3. An endoscope illumination apparatus comprising:

a light source for emitting illumination light along an optical axis of an optical path;

a condensing lens system; and means which provides selection of each illumination mode of the following four different illumination modes;

illumination mode 1—a mode that sequentially transmits excitation light for obtaining fluorescence from living body tissue and light having wavelength components different from the excitation light so as to obtain information from living body tissue other than by using fluorescence, illumination mode 2—a mode that sequentially transmits red, green, and blue wavelength ranges of light for obtaining color images of living body tissue, illumination mode 3—a mode which sequentially transmits very narrow wavelength ranges of at least two different wavelength regions within the visible spectrum, said wavelength ranges being more narrow than used in illumination mode 2, for enhancing the resolution of blood vessel structures at selected depths from the surface of living body tissue, one of said at least two different wavelength regions being light having wavelengths shorter than 440 nm, and illumination mode 4—a mode which sequentially transmits infrared region light having at least two different wavelength ranges for obtaining infrared images of living body tissue; wherein said means comprises a turret which is equipped with at least two optical filters having different spectral transmittance;

a rotary filter wheel which is equipped with two sets of optical filters arranged on the rotary filter wheel in concentric patterns and which is translatable into the optical path so that one of the two sets of optical filters can be sequentially rotated into the illumination light by rotating the rotary filter wheel;

at least one optical filter of the turret transmits light in at least two wavelength ranges;

at least one optical filter of the rotary filter wheel transmits light in at least two wavelength ranges; and another of said at least two different wavelength regions of illumination mode 3 being the green region, the intensity of illumination light in the green region for illumination mode 3 being less than the intensity of said illumination light for illumination mode 3 having wavelengths shorter than 440 nm.

4. The endoscope illumination apparatus as set forth in claim 3, wherein the intensity of illumination light in the green region is about one-fifth the intensity of said illumination light for illumination mode 3 having wavelengths shorter than 440 nm.

* * * * *